(12) United States Patent
Peri et al.

(10) Patent No.: US 12,274,503 B1
(45) Date of Patent: Apr. 15, 2025

(54) MYOPIA OCULAR PREDICTIVE TECHNOLOGY AND INTEGRATED CHARACTERIZATION SYSTEM

(71) Applicant: COGNITIVECARE INC., Milpitas, CA (US)

(72) Inventors: Venkata Narasimham Peri, Plano, TX (US); Naresh Nelaturi, Guntur (IN); Jagannadha Ganti, Hyderabad (IN); Suresh Venkata Satya Attili, Hyderabad (IN); Manoj Ramesh Teltumbade, Pittsburgh, PA (US); Sheena Gill, Centreville, VA (US); Errol R. Norwitz, Auburndale, MA (US); Chetan Chavan, Pune (IN); Prashant Garg, Hyderabad (IN); Pavan Verkicharla, Hyderabad (IN)

(73) Assignee: COGNITIVECARE INC., Milpitas, CA (US)

( * ) Notice: Subject to any disclaimer, the term of this patent is extended or adjusted under 35 U.S.C. 154(b) by 0 days.

(21) Appl. No.: 18/778,027

(22) Filed: Jul. 19, 2024

(51) Int. Cl.
*A61B 3/14* (2006.01)
*G06T 7/00* (2017.01)
(Continued)

(52) U.S. Cl.
CPC .............. *A61B 3/14* (2013.01); *G06T 7/0012* (2013.01); *G16H 20/00* (2018.01); *G16H 30/40* (2018.01);
(Continued)

(58) Field of Classification Search
CPC .......... A61B 3/14; G16H 50/30; G16H 50/20; G16H 20/00; G16H 30/40; G06T 7/0012
(Continued)

(56) References Cited

U.S. PATENT DOCUMENTS 10,667,680 B2 6/2020 Gupta et al.
10,722,180 B2 7/2020 Zhang et al.
(Continued)

FOREIGN PATENT DOCUMENTS

CN 111243742 A * 6/2020 ............. G02C 11/10
WO WO-2020200087 A1 * 10/2020 ............... A61B 3/00
(Continued)

*Primary Examiner* — James R Greece
(74) *Attorney, Agent, or Firm* — Davé Law Group, LLC; Raj S. Dave

(57) ABSTRACT

According to an embodiment, disclosed is a system comprising a processor wherein the processor is configured to receive an input data comprising an image of an ocular region of a user, clinical data of the user, and external factors; extract, using an image processing module comprising adaptive filtering techniques, ocular characteristics, combine, using a multimodal fusion module, the input data to determine a holistic health embedding; detect, based on a machine learning model and the holistic health embedding, a first output comprising likelihood of myopia, and severity of myopia; predict, based on the machine learning model and the holistic health embedding, a second output comprising an onset of myopia and a progression of myopia in the user; and wherein the machine learning model is a pre-trained model; and wherein the system is configured for myopia prognosis powered by multimodal data.

20 Claims, 33 Drawing Sheets

(51) Int. Cl.
  *G16H 20/00* (2018.01)
  *G16H 30/40* (2018.01)
  *G16H 50/20* (2018.01)
  *G16H 50/30* (2018.01)
(52) U.S. Cl.
  CPC ............ *G16H 50/20* (2018.01); *G16H 50/30* (2018.01); *G06T 2207/20081* (2013.01); *G06T 2207/20084* (2013.01); *G06T 2207/30041* (2013.01)
(58) Field of Classification Search
  USPC .................................................. 351/206, 246
  See application file for complete search history.

(56) References Cited

U.S. PATENT DOCUMENTS

| | | | |
|---|---|---|---|
| 2017/0020461 A1* | 1/2017 | Quinn | A61B 5/18 |
| 2021/0375460 A1 | 12/2021 | Li et al. | |
| 2022/0165418 A1 | 5/2022 | Li et al. | |
| 2022/0248955 A1* | 8/2022 | Tran | G16H 30/40 |

FOREIGN PATENT DOCUMENTS

| | | | | |
|---|---|---|---|---|
| WO | WO-2021211886 A1 * | 10/2021 | ............ | A61B 3/024 |
| WO | 2023079019 A1 | 5/2023 | | |
| WO | 2023079062 A1 | 5/2023 | | |
| WO | 2023195919 A3 | 10/2023 | | |

\* cited by examiner

| FEATURES NAMES | CHARACTERISTICS |
|---|---|
| GENDER | THE BIOLOGICAL SEX OF THE PATIENT ASSIGNED AT BIRTH. |
| AGE | THE AGE OF THE PATIENT AT THE TIME OF DIAGNOSIS. |
| PATIENT CATEGORY | A PATIENT CLASSIFICATION BASED ON CERTAIN CRITERIA, WHICH COULD INCLUDE THE TYPE OF PATIENT CARE (E.G., OUTPATIENT, INPATIENT), RISK CATEGORY, OR ANY OTHER RELEVANT CATEGORIZATION. |
| CHIEF COMPLAINTS | THE CHIEF COMPLAINTS OF THE PATIENT AS RECORDED IN THE CLINICAL OCULAR EXAMINATION AS PER SPECIFIC OCULAR EXAMINATION SYSTEM OR PROTOCOL. |
| PRESENT HISTORY | THE CURRENT OR PRESENT MEDICAL AND OCULAR HISTORY OF THE PATIENT. |
| DISTANCE VISUAL ACUITY OF THE EYE UNAIDED | THIS MEASURES HOW WELL THE PATIENT CAN SEE AT A DISTANCE WITHOUT CORRECTIVE LENSES. |
| TRP FR CORR SPH | THE SPHERICAL COMPONENT OF THE PRESCRIPTION FOR THE RIGHT EYE (OD) THAT CORRECTS FOR REFRACTIVE ERROR; IT INDICATES THE DEGREE OF MYOPIA OR HYPEROPIA. |
| TRP FR CORR CYL | THE CYLINDRICAL COMPONENT OF THE PRESCRIPTION FOR THE RIGHT EYE (OD), CORRECTING FOR ASTIGMATISM, WHICH IS MEASURED IN DIOPTERS AND INDICATES THE SHAPE OF THE CORRECTIVE LENS NEEDED. |
| TRP FR CORR AXIS | THE AXIS FOR THE CYLINDRICAL CORRECTION OF THE RIGHT EYE (OD), INDICATING THE ORIENTATION OF ASTIGMATISM IN DEGREES. |
| RETINO_SPHERICAL | THE SPHERICAL MEASUREMENT FROM RETINOSCOPY OF THE EYE, INDICATING THE DEGREE OF REFRACTIVE ERROR MEASURED DURING THE RETINOSCOPY PROCEDURE. |
| RETINO_CYLINDRICAL | THE CYLINDRICAL MEASUREMENT FROM RETINOSCOPY OF THE EYE, INDICATING THE DEGREE OF ASTIGMATISM MEASURED DURING THE RETINOSCOPY PROCEDURE. |
| FUNDUS | EXAMINATION FINDINGS OF THE FUNDUS (THE INTERIOR SURFACE OF THE EYE) OF THE EYE, WHICH COULD INCLUDE INFORMATION ON THE HEALTH OF THE RETINA, OPTIC DISC, AND BLOOD VESSELS. |
| TRP FR CORR BCVA | THE NUMERICAL VALUE OF THE BEST-CORRECTED VISUAL ACUITY FOR THE RIGHT EYE (OD), REPRESENTING THE BEST VISION THE PATIENT CAN ACHIEVE WITH THE CORRECT PRESCRIPTION LENS. |

FIG. 2A

| DATA ELEMENT | DATA ELEMENT VARIABLE | TYPE | HIGH FREQUENCY VALUES |
|---|---|---|---|
| GENDER ASSIGNED AT BIRTH | gender | Categorical | Female, Male |
| ALLERGIES | tocs_allergies | Categorical | Pollen, Dust, other |
| CURRENT TREATMENT | tocs_current_treatment | Categorical | Medication, None, using drops |
| CHIEF COMPLAINTS | tocs_chief_complaints | Categorical | Blurred Vision, Headache, opinion/test, distant vision |
| PRESENT HISTORY | tocs_present_history | Categorical | Blurred Vision, pain, redness, swelling |
| PAST MEDICAL HISTORY | tocs_past_history | Categorical | Acidity, anaemia, gastritis, Nil, thyroid, fits |
| OPTIC DISC SIZE | dgvst_optic_disc_size_od | Categorical | Medium, Large, Small |
| CUP DISC | dgvst_optic_disc_od | Categorical | Normal, Abnormal |
| FUNDUS | dgvst_fundus_od | Categorical | Normal, Abnormal, laser, lattice, lesions |
| OCULAR ALIGNMENT | ocular_alignment | Categorical | Normal, Orthotropic, HBT: Central, Esotropia, Exotropia |
| AGE | age | Numerical | 5 - 70 |
| CUP DISC RATIO | dgvst_cup_disc_ratio_od | Numerical | 0 - 1 |
|  | dgvst_od_cup_disk_ratio_mst_val | Numerical | 0 - 1 |
| IOP | dgvst_iop_od | Numerical | 0.5-34 |
| SPH | 1yr_od_retino_sph | Numerical | -50 to 9.5 |
|  | dgvst_od_retino_sph | Numerical | -50 to 11.5 |
|  | bcva | Numerical | 0.3 to 1.5 |
| AXIS | tor_fr_corr_axis | Numerical | -6 to 180 |
| CYL | cyl | Numerical | -50 to 4.5 |

FIG. 2B

| TRACK 1 (10 FEATURES) | TRACK 2 (12 FEATURES) |
|---|---|
| • GENDER ASSIGNED AT BIRTH, AGE<br>• CHIEF COMPLAINTS, PRESENT HISTORY,<br>• TOR VA UNAIDED,<br>• FUNDUS, BCVA<br>• SPH, CYL, TOR FR CORR AXIS | • GENDER ASSIGNED AT BIRTH, AGE<br>• PAST MEDICAL HISTORY, CURRENT TREATMENT, PRESENT CLINICAL HISTORY, CHIEF COMPLAINTS<br>• OPTIC DISC SIZE, CUP DISC RATIO, OPTIC DISC<br>• FUNDUS, IOP, OCULAR ALIGNMENT |
| OUTCOMES | OUTCOMES |
| • RISK OF PROGRESSION: PREDICT THE RISK OF PROGRESSION TOWARDS MYOPIA<br>• RISK OF DEVELOPMENT: PREDICT THE RISK OF DEVELOPMENT TOWARDS MYOPIA | • SCREENING: IDENTIFY THE PATIENTS WHO ARE LIKELY TO HAVE MYOPIA<br>• MYOPIA ASSESSMENT: ESTIMATE SEVERITY/MAGNITUDE – OF VISION DEGRADATION<br>• RISK OF PROGRESSION: PREDICT THE RISK OF PROGRESSION TOWARDS MYOPIA |

FIG. 4

| Iteration 1 | Iteration 2 | Iteration 3 | Iteration 4 | Iteration 5 |
|---|---|---|---|---|
| # features: 34 | # features: 28 | # features: 18 | # features: 14 | # features: 10 |
| 'dgvst_tot_vn_os_unaided', 'dgvst_trp_fr_corr_os_sph', 'dgvst_trp_fr_corr_os_axis', 'dgvst_optic_disc_size_os', 'dgvst_cup_disc_ratio_os', 'dgvst_os_cup_disk_ratio_mst_val', 'dgvst_optic_disc_os', 'dgvst_ocular_position', 'dgvst_eyelids_os', 'dgvst_cornea_os', 'dgvst_lens_os', 'dgvst_pvd_os', 'dgvst_macula_os', 'dgvst_fundus_os', 'dgvst_iop_os', 'dgvst_lens_od', 'tocs_nutritional_status', 'dgvst_number_of_visits', 'diag_age_category', 'dgvst_days_diff_first_last', 'diag_date', 'tocs_allergies', 'tocs_chief_complaints', 'tocs_current_treatment', 'diag_age', 'tocs_past_history', 'dgvst_ocular_alignment', 'gender', 'tocs_present_history', 'center_short_code', 'district', 'tocs_surgeries_lasers', 'patient_category' | 'dgvst_optic_disc_size_od', 'dgvst_cup_disc_ratio_od', 'dgvst_od_cup_disk_ratio_mst_val', 'dgvst_optic_disc_od', 'dgvst_eyelids_od', 'dgvst_cornea_od', 'dgvst_pvd_od', 'dgvst_macula_od', 'dgvst_fundus_od', 'dgvst_iop_od', 'dgvst_lens_od', 'dgvst_number_of_visits', 'diag_age_category', 'dgvst_days_diff_first_last', 'diag_date', 'tocs_allergies', 'tocs_chief_complaints', 'tocs_current_treatment', 'diag_age', 'tocs_past_history', 'dgvst_ocular_alignment', 'gender', 'tocs_present_history', 'center_short_code', 'district', 'nutritional_status', 'tocs_surgeries_lasers', 'patient_category' | 'dgvst_optic_disc_size_od', 'dgvst_cup_disc_ratio_od', 'dgvst_od_cup_disk_ratio_mst_val', 'dgvst_optic_disc_od', 'dgvst_fundus_od', 'dgvst_iop_od', 'dgvst_days_diff_first_last', 'tocs_allergies', 'tocs_chief_complaints', 'tocs_current_treatment', 'diag_age', 'tocs_past_history', 'dgvst_ocular_alignment', 'gender', 'tocs_present_history', 'center_short_code', 'district', 'patient_category' | 'dgvst_optic_disc_size_od', 'dgvst_cup_disc_ratio_od', 'dgvst_od_cup_disk_ratio_mst_val', 'dgvst_optic_disc_od', 'dgvst_fundus_od', 'dgvst_iop_od', 'dgvst_days_diff_first_last', 'tocs_chief_complaints', 'tocs_current_treatment', 'diag_age', 'tocs_past_history', 'dgvst_ocular_alignment', 'gender', 'tocs_present_history' | 'dgvst_optic_disc_size_od', 'dgvst_cup_disc_ratio_od', 'dgvst_od_cup_disk_ratio_mst_val', 'dgvst_optic_disc_od', 'dgvst_fundus_od', 'dgvst_iop_od', 'diag_age', 'dgvst_ocular_alignment', 'gender', 'tocs_present_history' |
| Model Performance: Accuracy 65% Decision Tree | Model Performance: Before encoding Accuracy 65% (Decision Tree) Post encoding Accuracy 65% (Decision Tree) | Model Performance: Accuracy 85% Decision Tree | Model Performance: Accuracy 86% Decision Tree | Model Performance: Accuracy 86% Decision Tree |

FIG. 5

| Column | Data type | Unique values | Missing values |
|---|---|---|---|
| gender | float64 | 2 | 0 |
| diag_age | float64 | 40 | 0 |
| patient_category | float64 | 4 | 0 |
| tocs_chief_complaints | float64 | 11 | 0 |
| tocs_present_history | float64 | 77 | 0 |
| dgvst_tor_va_od_unaided | object | 23 | 0 |
| dgvst_trp_fr_corr_od_sph | float64 | 83 | 0 |
| dgvst_trp_fr_corr_od_cyl | float64 | 27 | 0 |
| dgvst_trp_fr_corr_od_axis | int64 | 37 | 0 |
| dgvst_od_retino_sph | float64 | 85 | 0 |
| dgvst_od_retino_cyl | float64 | 30 | 0 |
| dgvst_fundus_od | float64 | 13 | 0 |
| num_trp_fr_corr_od_bcva | float64 | 21 | 0 |

FIG. 6

| dgyst_od_retino_sph | | | | | | 1yr_od_retino_sph | | | | | | sph_difference | | | | | |
|---|---|---|---|---|---|---|---|---|---|---|---|---|---|---|---|---|---|
| Pandas dtype | Valid | Uniques | | Missing values | | Pandas dtype | Valid | Uniques | | Missing values | | Pandas dtype | Valid | Uniques | | Missing values | |
| float64 | 11199 | 93 | | 0 | | float64 | 11199 | 111 | | 0 | | float64 | 11199 | 103 | | 0 | |
| Top 10 values of column | Count | % | Cum. count | | Cum. % | Top 10 values of column | Count | % | Cum. count | | Cum. % | Top 10 values of column | Count | % | Cum. count | | Cum. % |
| -0.500000 | 2190 | 19.6 | 2190 | | 19.6 | -0.500000 | 1573 | 14 | 1573 | | 14.0 | 0.000000 | 4012 | 35.8 | 4012 | | 35.8 |
| -1.000000 | 1038 | 9.3 | 3228 | | 28.8 | -1.000000 | 899 | 8 | 2472 | | 22.1 | 0.500000 | 1282 | 11.4 | 5294 | | 47.3 |
| -0.750000 | 1005 | 9 | 4233 | | 37.8 | -0.750000 | 853 | 7.6 | 3325 | | 29.7 | -0.500000 | 1158 | 10.3 | 6452 | | 57.6 |
| -1.500000 | 830 | 7.4 | 5063 | | 45.2 | -1.500000 | 764 | 6.8 | 4089 | | 36.5 | -0.250000 | 1144 | 10.2 | 7596 | | 67.8 |
| -2.000000 | 712 | 6.4 | 5775 | | 51.6 | -2.000000 | 695 | 6.2 | 4784 | | 42.7 | 0.250000 | 1137 | 10.2 | 8733 | | 78.0 |
| -2.500000 | 505 | 4.5 | 6280 | | 56.1 | -2.500000 | 538 | 4.8 | 5322 | | 47.5 | -1.000000 | 418 | 3.7 | 9151 | | 81.7 |
| -3.000000 | 498 | 4.4 | 6778 | | 60.5 | -3.000000 | 473 | 4.2 | 5795 | | 51.7 | 1.000000 | 407 | 3.6 | 9558 | | 85.3 |
| -1.250000 | 402 | 3.6 | 7180 | | 64.1 | 0.000000 | 424 | 3.8 | 6219 | | 55.5 | 0.750000 | 289 | 2.6 | 9847 | | 87.9 |
| -3.500000 | 340 | 3 | 7520 | | 67.1 | -1.250000 | 381 | 3.4 | 6600 | | 58.9 | -0.750000 | 266 | 2.4 | 10113 | | 90.3 |
| -4.000000 | 311 | 2.8 | 7831 | | 69.9 | -3.500000 | 345 | 3.1 | 6945 | | 62.0 | 1.500000 | 145 | 1.3 | 10258 | | 91.6 |

FIG. 7

"target"

| Pandas dtype | Valid | Uniques | Missing values |
|---|---|---|---|
| int64 | 11199 | 2 | 0 |

| 'target' value | Count | % |
|---|---|---|
| 0 | 8702 | 77.703366 |
| 1 | 2497 | 22.296634 |

FIG. 8

| AI Algorithm | Accuracy Train | Accuracy Validation | Accuracy Test | Confusion Matrix Test set # records : | Precision | | Recall | |
|---|---|---|---|---|---|---|---|---|
| | | | | | Label: Yes | Label: No | Label: Yes | Label: No |
| Linear SVC | 0.88 | 0.88 | 0.88 | Tn: 1450 Fp: 60 Fn: 168 Tp: 332 | 0.85 | 0.90 | 0.66 | 0.96 |
| Gaussian NB | 0.79 | 0.79 | 0.79 | Tn: 1462 Fp: 48 Fn: 362 Tp: 138 | 0.74 | 0.80 | 0.28 | 0.97 |
| Kneighbors Classifier | 0.81 | 0.80 | 0.80 | Tn: 1478 FP: 32 Fn: 359 Tp: 141 | 0.80 | 0.82 | 0.28 | 0.98 |
| Logistic Regression | 0.92 | 0.90 | 0.92 | Tn: 1421 FP: 89 Fn: 70 Tp: 430 | 0.83 | 0.95 | 0.86 | 0.94 |
| Decision Tree Classifier | 0.86 | 0.84 | 0.86 | Tn: 1402 Fp: 108 Fn: 75 Tp: 425 | 0.80 | 0.95 | 0.85 | 0.93 |
| SGD Classifier | 0.77 | 0.76 | 0.76 | Tn: 1505 Fp: 5 Fn: 459 Tp: 41 | 0.89 | 0.77 | 0.08 | 1.0 |
| Bagging Classifier | 0.99 | 0.93 | 0.98 | Tn: 1502 Fp: 8 Fn: 15 Tp: 485 | 0.98 | 0.99 | 0.99 | 0.97 |
| Extra Trees Classifier | 0.99 | 0.92 | 0.98 | Tn: 1498 Fp: 12 Fn: 20 Tp: 480 | 0.98 | 0.99 | 0.96 | 0.99 |
| Random Forest Classifier | 0.95 | 0.93 | 0.95 | Tn: 1500 Fp: 10 Fn: 71 Tp: 429 | 0.98 | 0.95 | 0.86 | 0.99 |
| XGB | 0.97 | 0.94 | 0.94 | Tn: 1484 FP: 26 Fn: 86 Tp: 414 | 0.94 | 0.95 | 0.83 | 0.98 |

FIG. 9

"target"

| Pandas dtype | Valid | Uniques | Missing values |
|---|---|---|---|
| int32 | 4360 | 2 | 0 |

| 'target' value | Count | % |
|---|---|---|
| 0 | 3288 | 75.412844 |
| 1 | 1072 | 24.587156 |

FIG. 10

| AI Algorithm | Accuracy Train | Accuracy Validation | Accuracy Test | Confusion Matrix Test set # records : | Precision | | Recall | |
|---|---|---|---|---|---|---|---|---|
| | | | | | Label: Yes | Label: No | Label: Yes | Label: No |
| Linear SVC | 0.67 | 0.67 | 0.67 | Tn: 420 Fp: 238 Fn: 43 Tp: 171 | 0.42 | 0.91 | 0.80 | 0.64 |
| Gaussian NB | 0.76 | 0.78 | 0.76 | Tn: 623 Fp: 35 Fn: 173 Tp: 41 | 0.54 | 0.78 | 0.19 | 0.95 |
| Kneighbors Classifier | 0.87 | 0.76 | 0.85 | Tn: 656 FP: 2 Fn: 124 Tp: 90 | 0.98 | 0.84 | 0.42 | 1.0 |
| Logistic Regression | 0.85 | 0.84 | 0.85 | Tn: 574 FP: 84 Fn: 40 Tp: 174 | 0.67 | 0.93 | 0.81 | 0.87 |
| Decision Tree Classifier | 0.98 | 0.85 | 0.96 | Tn: 647 Fp: 11 Fn: 18 Tp: 196 | 0.95 | 0.97 | 0.92 | 0.98 |
| SGD Classifier | 0.77 | 0.75 | 0.76 | Tn: 653 Fp: 5 Fn: 197 Tp: 17 | 0.77 | 0.77 | 0.08 | 0.99 |
| Bagging Classifier | 0.98 | 0.88 | 0.96 | Tn: 653 Fp: 5 Fn: 22 Tp: 192 | 0.97 | 0.97 | 0.90 | 0.99 |
| Extra Trees Classifier | 0.98 | 0.88 | 0.98 | Tn: 649 Fp: 9 Fn: 7 Tp: 207 | 0.96 | 0.99 | 0.97 | 0.99 |
| Random Forest Classifier | 0.92 | 0.90 | 0.92 | Tn: 648 Fp: 10 Fn: 53 Tp: 161 | 0.94 | 0.92 | 0.75 | 0.98 |
| SVC | 0.87 | 0.83 | 0.87 | Tn: 593 FP: 65 Fn: 44 Tp: 170 | 0.72 | 0.93 | 0.72 | 0.90 |

FIG. 11

|  | Baseline Dataset | | Curated Dataset (Post cleansing and imputation) | |
| --- | --- | --- | --- | --- |
| Total Columns & Records (for 35 centers) | 328,077 records / 120 columns | | 328,077 records / 120 columns | |
| Exclusion of 38 columns with > 50% missing values | 328,077 records / 82 columns | | 328,077 records / 82 columns | |
| Cleansing of missing values in Retino Sphere (retino_sph) columns | 326,984 records / 82 columns | | 326,984 records / 82 columns | |
| Cleansing of missing values in Retino Cylinder (retino_cyl) columns | 88,775 records / 84 columns | | 326,984 records / 84 columns | |
| Age Distribution | 0 – 10 years | 9220 | 0 – 10 years | 26880 |
|  | 11 – 20 years | 24196 | 11 – 20 years | 86520 |
|  | 21 – 30 years | 27944 | 21 – 30 years | 107142 |
|  | 31 – 40 years | 18703 | 31 – 40 years | 73876 |
|  | 41 – 50 years | 7298 | 41 – 50 years | 26451 |
|  | 51 – 60 years | 1661 | 51 – 60 years | 5651 |
| Exclusion of Age > 40 | 79,850 records / 84 columns | | 294,418 records / 84 columns | |
| Exclusion of high-correlation and redundant columns | 79,850 records / 73 columns | | 294,418 records / 73 columns | |
| Cleansing of Cornea labels | 77,444 records / 73 columns | | 280,166 records / 73 columns | |

FIG. 12

|  | Baseline | | 1st Year | 2nd Year | 3rd Year | 4th Year | 5th Year | 6th Year |
|---|---|---|---|---|---|---|---|---|
|  | Total | Curated | Total | Total | Total | Total | Total | Total |
| Baseline | 328,077 | 280,166 | 39,639 | 17,169 | 11,174 | 8,828 | 5,822 | 3,517 |
| 1st Year | 40,185 | 39,639 | 39,639 | 6039 |  |  |  |  |
| 2nd Year | 17,169 |  |  | 11,130 | 1991 |  |  |  |
| 3rd Year | 11,174 |  |  |  | 9,183 | 811 |  |  |
| 4th Year | 8,828 |  |  |  |  | 8,017 | 310 |  |
| 5th Year | 5,822 |  |  |  |  |  | 5,512 | 131 |
| 6th Year | 3,517 |  |  |  |  |  |  | 3,386 |

FIG. 13

| Variable Name | Data Type | Count | Missing Value - % |
|---|---|---|---|
| uid | object | 165,816 | 428 - 0.2% |
| tp_mrno | object | 244,085 | 418 - 0.2% |
| Noeye_Ocular_Diagnosis_visit | object | 280 | 235,926 - 96.4% |
| Noeye_Ocular_Diagnosis_all | object | 352 | 235,173 - 96.1% |
| SystemicDiagnosis_all | object | 3,460 | 235,157 - 96.1% |
| SystemicDiseases_all | object | 1,534 | 241,702 - 98.8% |
| dgvst_tr_review_notes | object | 12 | 244,700 - 100.0% |
| dgvst_tor_pgp_od_cyl | object | 136 | 226,190 - 92.4% |
| dgvst_tor_pgp_od_axis | object | 205 | 226,487 - 92.5% |
| dgvst_tor_pgp_os_cyl | object | 149 | 225,921 - 92.3% |
| dgvst_tor_pgp_os_axis | object | 208 | 226,195 - 92.4% |
| dgvst_tor_pgp_remarks | object | 4,565 | 228,634 - 93.4% |
| dgvst_Lens_Capsule_OD | object | 5 | 244,638 - 100.0% |
| dgvst_Anterior_Vitreous_OD | object | 130 | 229,794 - 93.9% |
| dgvst_Lens_Capsule_OS | object | 4 | 244,663 - 100.0% |
| dgvst_Anterior_Vitreous_OS | object | 128 | 229,895 - 93.9% |
| dgvst_tooc_fe_notes | object | 610 | 242,758 - 99.2% |
| dgvst_ascan_done_any_vst | object | 2 | 242,198 - 99.0% |
| dgvst_ascan_inv_any_vst | object | 4 | 242,198 - 99.0% |
| dgvst_fundus_photo_any_vst | object | 2 | 243,113 - 99.3% |
| dgvst_fundus_photo_inv_any_vst | object | 2 | 243,113 - 99.3% |
| dgvst_any_oct_any_vst | object | 2 | 241,984 - 98.9% |
| dgvst_any_oct_inv_any_vst | object | 32 | 241,984 - 98.9% |
| dgvst_myopic_clinic_vst | object | 2 | 244,693 - 100.0% |
| all_Advised_invest_OD | object | 174 | 242,016 - 98.9% |
| all_Done_invest_OD | object | 83 | 242,675 - 99.2% |
| all_Advised_invest_OS | object | 153 | 242,047 - 98.9% |
| all_Done_invest_OS | object | 67 | 242,687 - 99.2% |
| all_Advised_invest_OU | object | 718 | 233,376 - 95.4% |
| all_Done_invest_OU | object | 572 | 235,452 - 96.2% |

FIG. 14

| DATA STREAM I (10 FEATURES) |
|---|
| 1. GENDER |
| 2. AGE |
| 3. CHIEF COMPLAINTS |
| 4. PRESENT HISTORY |
| 5. TOR VA UNAIDED |
| 6. FUNDUS |
| 7. BCVA |
| 8. SPH (SPHERICAL BASELINE) |
| 9. CYL (CYLINDRICAL BASELINE) |
| 10. TOR FR CORR AXIS (AXIS) |
| OUTCOMES |
| 1. RISK OF PROGRESSION: PREDICT THE RISK OF PROGRESSION TOWARDS MYOPIA (SUB MODEL I) |
| 2. RISK OF DEVELOPMENT: PREDICT THE RISK OF DEVELOPMENT OF MYOPIA (SUB MODEL II) |

FIG. 15

| DATA STREAM II (12 FEATURES) |
|---|
| 1. GENDER |
| 2. AGE |
| 3. PAST MEDICAL HISTORY |
| 4. CURRENT TREATMENT |
| 5. PRESENT CLINICAL HISTORY |
| 6. CHIEF COMPLAINTS |
| 7. OPTIC DISC SIZE |
| 8. CUP DISC RATIO |
| 9. OPTIC DISC |
| 10. FUNDUS |
| 11. IOP |
| 12. OCULAR ALIGNMENT |
| OUTCOMES |
| 1. SCREENING: IDENTIFY THE PATIENTS WHO ARE LIKELY TO HAVE MYOPIA (SUB MODEL I) |
| 2. MYOPIA ASSESSMENT: ESTIMATE SEVERITY/MAGNITUDE OF VISION DEGRADATION (SUB MODEL II) |
| 3. RISK OF PROGRESSION: PREDICT THE RISK OF PROGRESSION TOWARDS MYOPIA (SUB MODEL III) |

FIG. 23

| AI Algorithm | Accuracy Train / Validation / Test | | | Confusion Matrix | Precision | Recall | Comments |
|---|---|---|---|---|---|---|---|
| Decision Tree Classifier | 0.88 | 0.86 | 0.87 | Tn: 25875 Fp: 1877 Fn: 5040 Tp: 23242 | 0.90 | 0.81 | Used baseline data of 280000 patients to train, validate and test. |

FIG. 24

MYOPIA      159605
EmmetropiA  133383
Hyperopia    11487
Name: od_retina_sph,

FIG. 25

| AI Algorithm | Accuracy Train / Validation / Test | | | Confusion Matrix | Precision | Recall | Comments |
|---|---|---|---|---|---|---|---|
| Decision Tree Classifier | 0.91 | 0.90 | 0.91 | [27313 33 65 513]<br>[907 31 16 1780]<br>[53 2 1 708]<br>[3307 44 20 8778] | 0.70 | 0.73 | Used baseline data of 220000 patients to train, validate and test.<br><br>Risk Score is translated to Severity levels of Emmetropia or Simple Myopia or Moderate Myopia or High Myopia. |

FIG. 26

| All value counts of column | Count |
|---|---|
| emmetropia | 143975 |
| simple myopia | 61349 |
| high myopia | 13605 |
| moderate myopia | 3924 |

FIG. 27

| AI Algorithm | Testing Accuracy | Comments |
|---|---|---|
| Computation | 0.83 | This model is created with a combination of Sub Model I and Sub Model II to estimate myopia progression in 12 months<br><br>Used 1-year follow up (approx. 12 months after baseline) visit data to evaluate |

RECEIVING, AN INPUT DATA COMPRISING AN IMAGE OF AN OCULAR REGION OF A USER, CLINICAL DATA OF THE USER, AND EXTERNAL FACTORS 3102

EXTRACTING, USING AN IMAGE PROCESSING MODULE COMPRISING ADAPTIVE FILTERING TECHNIQUES, OCULAR CHARACTERISTICS 3104

COMBINING, USING A MULTIMODAL FUSION MODULE, THE INPUT DATA TO DETERMINE A HOLISTIC HEALTH EMBEDDING 3106

DETECTING, BASED ON A MACHINE LEARNING MODEL AND THE HOLISTIC HEALTH EMBEDDING, A FIRST OUTPUT, WHEREIN THE FIRST OUTPUT COMPRISES LIKELIHOOD OF MYOPIA, AND SEVERITY OF MYOPIA 3108

PREDICTING, BASED ON THE MACHINE LEARNING MODEL AND THE HOLISTIC HEALTH EMBEDDING, A SECOND OUTPUT, WHEREIN THE SECOND OUTPUT COMPRISES AN ONSET OF MYOPIA AND A PROGRESSION OF MYOPIA 3110

STRATIFYING, RISK CATEGORY OF MYOPIA OF THE USER 3112

DISPLAYING, ON A USER INTERFACE, ONE OR MORE OF THE FIRST OUTPUT AND THE SECOND OUTPUT 3114

RECEIVING, A FIRST FEEDBACK OF THE FIRST OUTPUT AND THE SECOND OUTPUT, TO DYNAMICALLY ADJUST AN ACCURACY OF THE FIRST OUTPUT AND THE SECOND OUTPUT FROM THE MACHINE LEARNING MODEL 3116

RECEIVING, A SECOND FEEDBACK FROM A PHYSICIAN, TO DYNAMICALLY ADJUST THE ACCURACY OF THE FIRST OUTPUT AND THE SECOND OUTPUT FROM THE MACHINE LEARNING MODEL 3118

MYOPIA OCULAR PREDICTIVE TECHNOLOGY AND INTEGRATED CHARACTERIZATION SYSTEM

FIELD OF INVENTION

The present disclosure relates broadly to eye health prediction and more specifically to systems and methods for myopia prognosis powered by multimodal data for detecting myopia in an individual and its progression over time or risk of developing myopia in case the individual docs not currently have myopia at the time of eye test.

BACKGROUND

In this section Prior Art is quoted.

"Many ophthalmic diseases and disorders are diagnosed based on medical imaging, such as for example retinal imaging. Medical imaging has traditionally relied upon human experts to analyze images individually. As the number of medical imaging procedures increase, demand for efficient and accurate image analysis is outstripping the supply of experts capable of performing this function." [US Patent Publication Number U.S. Pat. No. 10,722,180B2 titled, "Deep learning-based diagnosis and referral of ophthalmic diseases and disorders"]

"Part of general health is eye health. From time to time, for example, once a year, an eye patient can visit an eye practitioner (e.g., an optometrist or ophthalmologist) for an cyc examination. The eye practitioner can measure various eye characteristics and perform various eye tests to determine general eye health. Eye characteristics can change over time, especially with age. Thus, eye patients can return to an eye practitioner on an ongoing basis to check for changes in eye characteristics." [US Patent Publication Number U.S. Pat. No. 10,667,680B2 titled, "Forecasting eye condition progression for eye patients"]

"These types of irregular or redundant eye practitioner visits are especially problematic in pediatric settings. Parents of a child are typically very eager to know not just the current condition of their child's eyes but also a treatment plan for any corrections and when those corrections may occur. Unfortunately, it is difficult to take the current eye condition as an input and determine a timed treatment plan with desired outcomes." [US Patent Publication Number U.S. Pat. No. 10,667,680B2 titled, "Forecasting eye condition progression for eye patients"]

"Despite advances in medical and surgical interventions, the burden of visual impairment remains globally high. Out of a worldwide population of 7.3 billion, an estimated 441.11 million individuals experienced some form of visual impairment in 2015, with more than 70% of cases attributed to a handful of eye conditions and 82% of cases classified as potentially avoidable. Retinal diseases, and the manifestations they carry, not only impact sight but impose serious personal and financial burdens on the patient. Visual impairment has been linked with reduced economic productivity, reduced quality of life, and increased mortality." [US Patent Application Publication Number US20220165418A1 titled, "Image-based detection of ophthalmic and systemic diseases"].

Therefore, there is a need for a system and method that can detect not only the current cyc condition but also predict future eye condition and progress of the eye condition along with suggested treatment options.

SUMMARY

The following presents a summary to provide a basic understanding of one or more embodiments described herein. This summary is not intended to identify key or critical elements or delineate any scope of the different embodiments and/or any scope of the claims. The sole purpose of the summary is to present some concepts in a simplified form as a prelude to the more detailed description presented herein.

According to an embodiment, disclosed is a system comprising a processor storing instructions in non-transitory memory that, when executed, cause the processor to receive, via an input module, an input data, wherein the input data comprises an image of an ocular region of a user, clinical data of the user, and external factors; extract, using an image processing module comprising adaptive filtering techniques, ocular characteristics, wherein the ocular characteristics comprise one or more of Optic Disc Size, Cup Disc Ratio, Optic Disc, Fundus, Intraocular Pressure (IOP), Ocular Alignment, Toric Cylinder Axis unaided (Tor CA unaided), Best Corrected Visual Acuity (BCVA), Spherical Power (SPH), Cylindrical (CYL), Toric Front Corrected Axis (Tor fr corr axis); combine, using a multimodal fusion module, the input data to determine a holistic health embedding; detect, based on a machine learning model and the holistic health embedding, a first output, wherein the first output comprises the likelihood of myopia, and severity of myopia; predict, based on the machine learning model and the holistic health embedding, a second output, wherein the second output comprises an onset of myopia and a progression of myopia in the user; stratify, risk category of myopia of the user; display, on a user interface, one or more of the first output and the second output; receive, a first feedback of the first output and the second output from the machine learning model to dynamically adjust an accuracy of the first output and the second output from the machine learning model; receive, a second feedback from a physician to dynamically adjust the accuracy of the first output and the second output from the machine learning model; and wherein the machine learning model is a pre-trained model with a data set comprising the input data from plurality of patients to recognize one or more patterns using the holistic health embedding.

According to an embodiment of the system, the system is further configured to extract and analyze the ocular characteristics from digital images utilizing deep learning techniques, comprising preprocessing the digital images to enhance ocular region visibility; and employing a convolutional neural network (CNN) tailored for ocular region detection and feature extraction.

According to an embodiment of the system, the system is configured for comprehensive ocular health assessment.

According to an embodiment of the system, the system further comprises a multimodal fusion module designed to combine the ocular characteristics with the external factors using the machine learning model to generate the holistic health embedding.

According to an embodiment of the system, the system has generative artificial intelligence module to preprocess and enhance the quality of multimodal data inputs for the detection and prognosis of myopia.

According to an embodiment of the system, a dynamic embedding adjustment mechanism is configured to update the holistic health embedding based on real-time environmental and behavioral data inputs of the user, wherein the dynamic embedding adjustment is continuous, and allows adaptive modification of vector representations of data, in response to new information or changes in underlying data distribution.

According to an embodiment of the system, the dynamic embedding adjustment mechanism is further capable of learning from the second feedback of the physician and integrating clinical adjustments into the machine learning model.

According to an embodiment of the system, the machine learning model comprises an Artificial Intelligence (AI) based predictive framework for the onset and progression of myopia, wherein the AI based predictive framework comprises a dual-pathway AI model employing separate but interconnected neural networks for predicting the onset and progression of myopia, based on non-spherical ocular embeddings, with one pathway dedicated to binary myopia onset prediction and a second pathway to continuous progression rate estimation.

According to an embodiment of the system, the system further comprises a learning adaptation module that dynamically adjusts the AI based predictive framework based on a longitudinal patient data, configured to enhance prediction accuracy over time, wherein the longitudinal patient data is a data that is collected over a period of time from the user.

According to an embodiment of the system, the system further includes an external factors impact assessment module that quantifies the influence of individual external factors on the first output and the second output.

According to an embodiment of the system, the external factors comprise one or more of device screen exposure time, outdoor activity metrics, and social determinants of health on myopia risk.

According to an embodiment of the system, the pre-trained model is calibrated and selected from one or more AI models for myopia assessment using genetic algorithms by evaluating AI model candidates against a set of performance criteria.

According to an embodiment of the system, the set of performance criteria comprise prediction accuracy, computational efficiency, and adaptability to diverse patient data.

According to an embodiment of the system, the system is further configured to use patient outcome data to refine parameters of the genetic algorithm.

According to an embodiment of the system, the adaptive filtering techniques are performed to compensate for variations in image quality due to lighting conditions.

According to an embodiment of the system, the user interface is configured for healthcare providers to visualize the first output and the second output alongside the input that is contributing to the first output and the second output, facilitating a holistic approach to patient counselling and treatment management.

According to an embodiment of the system, the system is further configured to collect data from a wearable device for real-time data capture of latent characteristics influencing myopia comprising blink rate, gaze direction, and ambient light exposure.

According to an embodiment of the system, the machine learning model comprises one or more of logistic regressions, support vector machines (SVM), K-nearest neighbors, decision trees, and ensemble models.

According to an embodiment of the system, the ensemble model comprises one or more of random forests, extra trees, and bagging.

According to an embodiment of the system, the clinical data comprises one or more of clinical observations made by healthcare, diagnostic test results, and treatment information, health monitoring data, behavioral and lifestyle information.

According to an embodiment of the system, the clinical data further comprises patient reported outcomes.

According to an embodiment of the system, the first output further comprises a prediction of progress rate.

According to an embodiment of the system, the holistic health embedding is a multidimensional representation of a health profile of the user.

According to an embodiment of the system, the system may further provide a third output comprising one or more of treatment strategies, treatment options, appointment schedule generation.

According to an embodiment of the system, the machine learning model is configured to learn using labelled data using a supervised learning, wherein the supervised learning comprises logic using at least one of a decision tree, a logistic regression, a support vector machine, a k-nearest neighbors, a Naïve Bayes, a random forest, a linear regression, and a polynomial regression.

According to an embodiment of the system, the system further comprises artificial intelligence driven models for generating explanatory narratives and dynamic visual representations based on the first output and the second output.

According to an embodiment of the system, the machine learning model is configured to learn from real-time data using an unsupervised learning, wherein the unsupervised learning comprises logic using at least one of a k-means clustering, a hierarchical clustering, a hidden Markov model, and an apriori algorithm.

According to an embodiment of the system, the machine learning model has a feedback loop, wherein the first output and the second output from a previous step is fed back to the model in real-time to improve performance and accuracy of the output of a next step.

According to an embodiment of the system, the machine learning model comprises a recurrent neural network model.

According to an embodiment of the system, the machine learning model has a feedback loop, wherein learning is further reinforced with a reward for each true positive of the output of the system.

According to an embodiment, disclosed is a method comprising, receiving, via an input module, an input data, wherein the input data comprises an image of an ocular region of a user, clinical data of the user, and external factors; extracting, using an image processing module comprising adaptive filtering techniques, ocular characteristics, wherein the ocular characteristics comprise one or more of Optic Disc Size, Cup Disc Ratio, Optic Disc, Fundus, IOP, Ocular Alignment, Tor CA unaided, BCVA, SPH, Cyl, Tor fr corr axis; combining, using a multimodal fusion module, the input data to determine a holistic health embedding; detecting, based on a machine learning model and the holistic health embedding, a first output, wherein the first output comprises the likelihood of myopia, and severity of myopia; predicting, based on the machine learning model and the holistic health embedding, a second output, wherein the second output comprises an onset of myopia and a progression of myopia in the user; stratifying, risk category of myopia of the user; displaying, on a user interface, one or more of the first output and the second output; receiving, a first feedback of the first output and the second output from the machine learning model to dynamically adjust an accuracy of the first output and the second output from the machine learning model; receiving, a second feedback from a physician to dynamically adjust the accuracy of the first output and the second output from the machine learning model; and wherein the machine learning model is a pre-trained model with a data set comprising the input data from plurality of patients to recognize one or more patterns using the holistic health embedding.

According to an embodiment of the method, the external factors comprise one or more of device screen exposure time, outdoor activity metrics, and social determinants of health.

According to an embodiment of the method, the user interface is configured for healthcare providers to visualize the first output and the second output alongside the input that is contributing to the first output and the second output, facilitating a holistic approach to patient counselling and treatment management.

According to an embodiment of the method, the machine learning model comprises one or more of logistic regressions, support vector machines (SVM), K-nearest neighbors, decision trees, and ensemble models.

According to an embodiment of the method, the ensemble model comprises one or more of random forests, extra trees, and bagging.

According to an embodiment, disclosed is a non-transitory computer-readable medium having stored thereon instructions executable by a computer system to perform operations comprising receiving, via an input module, an input data, wherein the input data comprises an image of an ocular region of a user, clinical data of the user, and external factors, wherein the external factors comprise one or more of device screen exposure time, outdoor activity metrics, and social determinants of health; extracting, using an image processing module comprising adaptive filtering techniques, ocular characteristics, wherein the ocular characteristics comprise one or more of Optic Disc Size, Cup Disc Ratio, Optic Disc, Fundus, IOP, Ocular Alignment, Tor CA unaided, BCVA, SPH, Cyl, Tor fr corr axis; combining, using a multimodal fusion module, the input data to determine a holistic health embedding; detecting, based on a machine learning model and the holistic health embedding, a first output, wherein the first output comprises the likelihood of myopia, and severity of myopia; predicting, based on the machine learning model and the holistic health embedding, a second output, wherein the second output comprises an onset of myopia and a progression of myopia in the user; stratifying, risk category of myopia of the user; displaying, on a user interface, one or more of the first output and the second output; receiving, a first feedback of the first output and the second output from the machine learning model, to dynamically adjust an accuracy of the first output and the second output from the machine learning model; receiving, a second feedback from a physician to dynamically adjust the accuracy of the first output and the second output from the machine learning model; and wherein the machine learning model is a pre-trained model with a data set comprising the input data from plurality of patients to recognize one or more patterns using the holistic health embedding.

According to an embodiment of the non-transitory computer-readable medium, the external factors comprise one or more of device screen exposure time, outdoor activity metrics, and social determinants of health.

According to an embodiment, disclosed is a method comprising, receiving, via an input module, an input data, wherein the input data comprises an image of an ocular region of a user, clinical data of the user, and external factors; extracting, using an image processing module comprising adaptive filtering techniques, ocular characteristics, wherein the ocular characteristics comprise one or more of Optic Disc Size, Cup Disc Ratio, Optic Disc, Fundus, IOP, Ocular Alignment, Tor CA unaided, BCVA, SPH, Cyl, Tor fr corr axis; combining, using a multimodal fusion module, the input data to determine a holistic health embedding; detecting, based on a machine learning model and the holistic health embedding, a first output, wherein the first output comprises likelihood of myopia, and severity of myopia; predicting, based on the machine learning model and the holistic health embedding, a second output, wherein the second output comprises an onset of myopia and a progression of myopia in the user; stratifying, risk category of myopia of the user; displaying, on a user interface, one or more of the first output and the second output; interfacing, the user interface with generative artificial intelligence to produce dynamic visualizations and narrative summaries that explain model predictions in an intuitive manner configured to aid clinicians in interpreting complex data sets for making informed decisions; receiving, a first feedback of the first output and the second output from the machine learning model, to dynamically adjust an accuracy of the first output and the second output from the machine learning model; and receiving, a second feedback from a physician, to dynamically adjust the accuracy of the first output and the second output from the machine learning model; and wherein the machine learning model is a pre-trained model with a data set comprising the input data from plurality of patients to recognize one or more patterns using the holistic health embedding; and wherein the system is configured for myopia prognosis powered by multimodal data.

BRIEF DESCRIPTION OF THE FIGURES

These and other aspects of the present invention will now be described in more detail, with reference to the appended drawings showing exemplary embodiments of the present invention, in which:

FIG. 2A shows patient data comprising ocular features according to an embodiment.

FIG. 2B shows different types of data and elements present in the data according to an embodiment.

FIG. 4 shows input features and feature engineering according to an embodiment.

FIG. 5 shows multiple iterations for selection of features based on a performance metric according to an embodiment.

FIG. 6 shows a selected list of features for building an AI model on predicting the progression of myopia according to an embodiment.

FIG. 7 shows a target variable and its derivation for building an AI model on predicting the progression of myopia according to an embodiment.

FIG. 8 shows the stratification of progression using the target variable according to an embodiment.

FIG. 9 shows training and evaluation of Myopia Progression Models according to an embodiment.

FIG. 10 shows the stratification of progression using the target variable according to an embodiment.

FIG. 11 shows training and evaluation of Myopia Progression Models according to an embodiment.

FIG. 12 shows high level data summary used for Myopia Informed Artificial Intelligence System development according to an embodiment.

FIG. 13 shows longitudinal patient data summary for Myopia Informed Artificial Intelligence System according to an embodiment.

FIG. 14 shows features that are least important in the myopia prediction according to an embodiment.

FIG. 15 shows Data stream I used for training Model I according to an embodiment.

FIG. 23 shows Data stream II for development of Model II according to an embodiment.

FIG. 24 shows Model II, Sub-Model I performance analysis according to an embodiment.

FIG. 25 shows Model II, Sub-Model I, performance analysis according to an embodiment.

FIG. 26 shows Model II, Sub-Model II, performance analysis according to an embodiment.

FIG. 27 shows Model II, Sub-Model II, performance analysis according to an embodiment.

FIG. 28 shows Model II, Sub-Model III, performance analysis according to an embodiment.

FIG. 31 shows a block diagram of the method implemented by the Myopia Informed Artificial Intelligence System according to an embodiment.

FIG. 32 shows a graphical user interphase for myopia progression models of Myopia Informed Artificial Intelligence System.

FIG. 33 shows a graphical user interphase for myopia risk prediction models of Myopia Informed Artificial Intelligence System.

DETAILED DESCRIPTION

Definitions and General Techniques

Figure 1A:
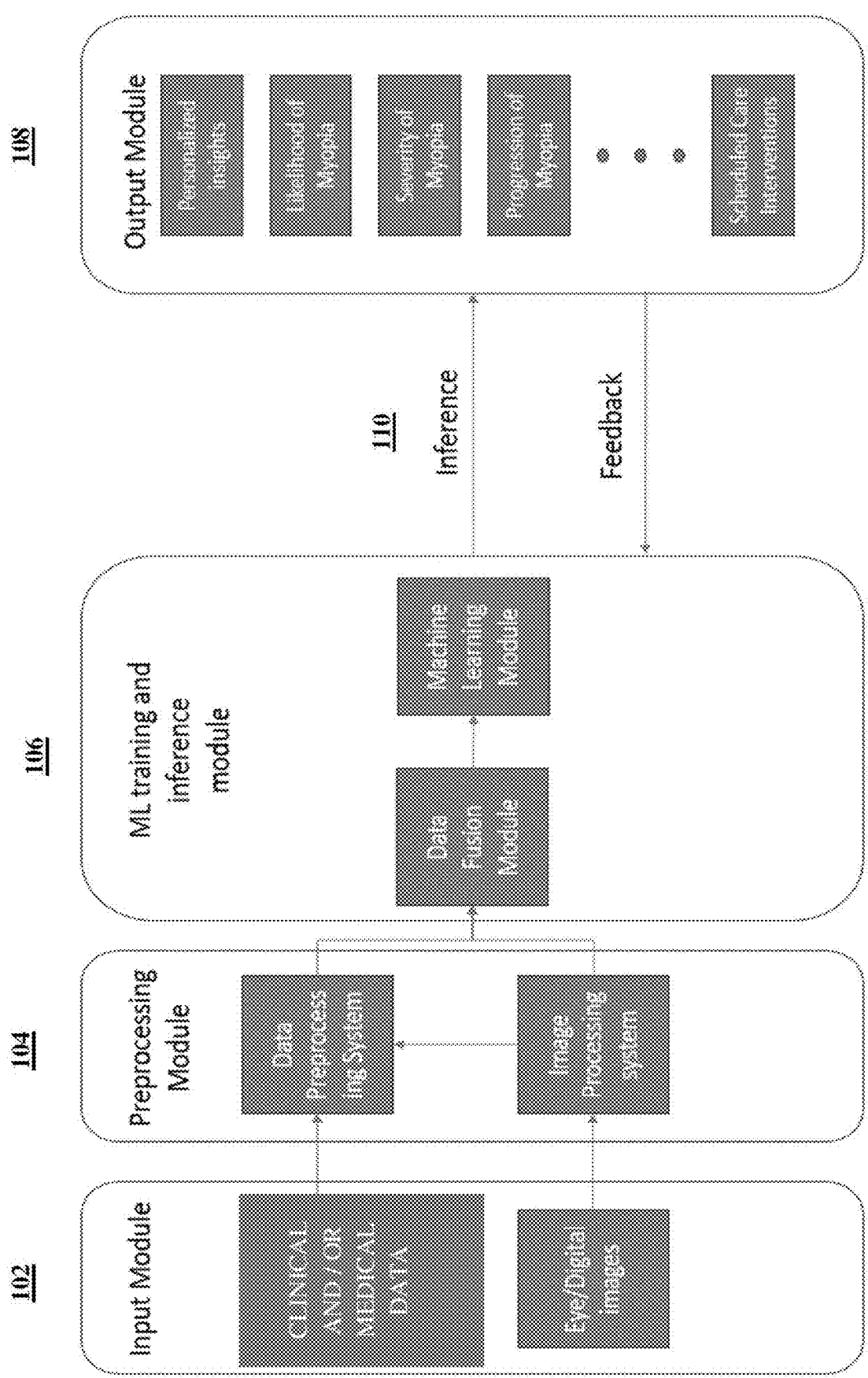
FIG. 1A shows the Myopia Informed Artificial Intelligence System comprising a dual module framework according to an embodiment.

For simplicity and clarity of illustration, the drawing figures illustrate the general manner of construction, and descriptions and details of well-known features and techniques may be omitted to avoid unnecessarily obscuring the present disclosure. Additionally, elements in the drawing figures are not necessarily drawn to scale. For example, the dimensions of some of the elements in the figures may be exaggerated relative to other elements to help improve understanding of embodiments of the present disclosure. The same reference numerals in different figures denote the same elements.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Furthermore, the terms "include," and "have," and any variations thereof, are intended to cover a non-exclusive inclusion, such that a process, method, system, article, device, or apparatus that comprises a list of elements is not necessarily limited to those elements but may include other elements not expressly listed or inherent to such process, method, system, article, device, or apparatus.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments of the apparatus, methods, and/or articles of manufacture described herein are, for example, capable of operation in other orientations than those illustrated or otherwise described herein.

No element, act, or instruction used herein should be construed as critical or essential unless explicitly described as such. Also, as used herein, the articles "a" and "an" are intended to include items and may be used interchangeably with "one or more." Furthermore, as used herein, the term "set" is intended to include items (e.g., related items, unrelated items, a combination of related items, and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

The terms "couple," "coupled," "couples," "coupling," and the like should be broadly understood and refer to connecting two or more elements mechanically and/or otherwise. Two or more electrical elements may be electrically coupled together, but not be mechanically or otherwise coupled together. Coupling may be for any length of time, e.g., permanent or semi-permanent or only for an instant. "Electrical coupling" and the like should be broadly understood and include electrical coupling of all types. The absence of the word "removably," "removable," and the like near the word "coupled," and the like does not mean that the coupling, etc. in question is or is not removable.

As defined herein, two or more elements are "integral" if they are comprised of the same piece of material. As defined herein, two or more elements are "non-integral" if each is comprised of a different piece of material.

As defined herein, "real-time" can, in some embodiments, be defined with respect to operations carried out as soon as practically possible upon occurrence of a triggering event. A triggering event can include receipt of data necessary to execute a task or to otherwise process information. Because of delays inherent in transmission and/or in computing speeds, the term "real-time" encompasses operations that occur in "near" real-time or somewhat delayed from a triggering event. In a number of embodiments, "real-time" can mean real-time less a time delay for processing (e.g., determining) and/or transmitting data. The particular time delay can vary depending on the type and/or amount of the data, the processing speeds of the hardware, the transmission capability of the communication hardware, the transmission distance, etc. However, in many embodiments, the time delay can be less than approximately one second, two seconds, five seconds, or ten seconds.

The present disclosure may be embodied in other specific forms without departing from its spirit or characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

As defined herein, "approximately" can, in some embodiments, mean within plus or minus ten percent of the stated value. In other embodiments, "approximately" can mean within plus or minus five percent of the stated value. In further embodiments, "approximately" can mean within plus or minus three percent of the stated value. In yet other embodiments, "approximately" can mean within plus or minus one percent of the stated value.

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. Generally, nomenclatures used in connection with, and techniques of, health monitoring described herein are those well-known and commonly used in the art.

Digital electronic circuitry, or computer software, firmware, or hardware, including the structures disclosed in this specification and their structural equivalents, or in combinations of one or more of them may realize the implementations and all of the functional operations described in this specification. Implementations may be as one or more computer program products i.e., one or more modules of computer program instructions encoded on a computer-readable medium for execution by, or to control the operation of, data processing apparatus. The computer-readable medium may be a machine-readable storage device, a machine-readable storage substrate, a memory device, a composition of matter affecting a machine-readable propagated signal, or a combination of one or more of them. The term "computing system" encompasses all apparatus, devices, and machines for processing data, including by way of example, a programmable processor, a computer, or multiple processors or computers. The apparatus may include, in addition to hardware, code that creates an execution environment for the computer program in question, e.g., code that constitutes processor firmware, a protocol stack, a database management system, an operating system, or a combination of one or more of them. A propagated signal is an artificially generated signal (e.g., a machine-generated electrical, optical, or electromagnetic signal) that encodes information for transmission to a suitable receiver apparatus.

The actual specialized control hardware or software code used to implement these systems and/or methods is not limiting to the implementations. Thus, any software and any hardware can implement the systems and/or methods based on the description herein without reference to specific software code.

A computer program (also known as a program, software, software application, script, or code) is written in any appropriate form of programming language, including compiled or interpreted languages. Any appropriate form, including a standalone program or a module, component, subroutine, or other unit suitable for use in a computing environment may deploy it. A computer program does not necessarily correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may execute on one computer or on multiple computers that are located at one site or distributed across multiple sites and interconnected by a communication network.

One or more programmable processors, executing one or more computer programs to perform functions by operating on input data and generating output, perform the processes and logic flows described in this specification. The processes and logic flows may also be performed by, and apparatus may also be implemented as, special purpose logic circuitry, for example, without limitation, a Field Programmable Gate Array (FPGA), an Application Specific Integrated Circuit (ASIC), Application Specific Standard Products (ASSPs), System-On-a-Chip (SOC) systems, Complex Programmable Logic Devices (CPLDs), etc.

Processors suitable for the execution of a computer program include, by way of example, both general and special purpose microprocessors, and any one or more processors of any appropriate kind of digital computer. A processor will receive instructions and data from a read-only memory or a random-access memory or both. Elements of a computer can include a processor for performing instructions and one or more memory devices for storing instructions and data. A computer will also include, or is operatively coupled to receive data, transfer data or both, to/from one or more mass storage devices for storing data e.g., magnetic disks, magneto optical disks, optical disks, or solid-state disks. However, a computer need not have such devices. Moreover, another device, e.g., a mobile telephone, a personal digital assistant (PDA), a mobile audio player, a Global Positioning System (GPS) receiver, etc. may embed a computer. Computer-readable media suitable for storing computer program instructions and data include all forms of non-volatile memory, media and memory devices, including, by way of example, semiconductor memory devices (e.g., Erasable Programmable Read-Only Memory (EPROM), Electronically Erasable Programmable Read-Only Memory (EEPROM), and flash memory devices), magnetic disks (e.g., internal hard disks or removable disks), magneto optical disks (e.g. Compact Disc Read-Only Memory (CD ROM) disks, Digital Versatile Disk-Read-Only Memory (DVD-ROM) disks) and solid-state disks. Special purpose logic circuitry may supplement or incorporate the processor and the memory.

To provide for interaction with a user, a computer may have a display device, e.g., a Cathode Ray Tube (CRT) or Liquid Crystal Display (LCD) monitor, for displaying information to the user, and a keyboard and a pointing device, e.g., a mouse or a trackball, by which the user may provide input to the computer. Other kinds of devices provide for interaction with a user as well. For example, feedback to the user may be any appropriate form of sensory feedback, e.g., visual feedback, auditory feedback, or tactile feedback; and a computer may receive input from the user in any appropriate form, including acoustic, speech, or tactile input.

A computing system that includes a back-end component, e.g., a data server, or that includes a middleware component, e.g., an application server, or that includes a front-end component, e.g., a client computer having a graphical user interface or a Web browser through which a user may interact with an implementation, or any appropriate combination of one or more such back-end, middleware, or front-end components, may realize implementations described herein. Any appropriate form or medium of digital data communication, e.g., a communication network may interconnect the components of the system. Examples of communication networks include a Local Area Network (LAN) and a Wide Area Network (WAN), e.g., Intranet and Internet.

The computing system may include clients and servers. A client and server are remote from each other and typically interact through a communication network. The relationship of the client and server arises by virtue of computer programs running on the respective computers and having a client-server relationship with each other.

Embodiments of the present invention may comprise or utilize a special purpose or general purpose computer including computer hardware. Embodiments within the scope of the present invention may also include physical and other computer-readable media for carrying or storing computer-executable instructions and/or data structures. Such computer-readable media can be any media accessible by a general purpose or special purpose computer system. Computer-readable media that store computer-executable instructions are physical storage media. Computer-readable media that carry computer-executable instructions are transmission media. Thus, by way of example and not limitation, embodiments of the invention can comprise at least two distinct kinds of computer-readable media: physical computer-readable storage media and transmission computer-readable media.

Although the present embodiments described herein are with reference to specific example embodiments it will be evident that various modifications and changes may be made to these embodiments without departing from the broader spirit and scope of the various embodiments. For example, hardware circuitry (e.g., Complementary Metal Oxide Semiconductor (CMOS) based logic circuitry), firmware, software (e.g., embodied in a non-transitory machine-readable medium), or any combination of hardware, firmware, and software may enable and operate the various devices, units, and modules described herein. For example, transistors, logic gates, and electrical circuits (e.g., Application Specific Integrated Circuit (ASIC) and/or Digital Signal Processor (DSP) circuit) may embody the various electrical structures and methods.

In addition, a non-transitory machine-readable medium and/or a system may embody the various operations, processes, and methods disclosed herein. Accordingly, the specification and drawings are illustrative rather than restrictive.

Physical computer-readable storage media includes RAM, ROM, EEPROM, CD-ROM or other optical disk storage (such as CDs, DVDs, etc.), magnetic disk storage or other magnetic storage devices, solid-state disks or any other medium. They store desired program code in the form of computer-executable instructions or data structures which can be accessed by a general purpose or special purpose computer.

As used herein, the term "network" refers to one or more data links that enable the transport of electronic data between computer systems and/or modules and/or other electronic devices. When a network or another communications connection (either hardwired, wireless, or a combination of hardwired or wireless) transfers or provides information to a computer, the computer properly views the connection as a transmission medium. A general purpose or special purpose computer access transmission media that can include a network and/or data links which carry desired program code in the form of computer-executable instructions or data structures. The scope of computer-readable media includes combinations of the above, that enable the transport of electronic data between computer systems and/or modules and/or other electronic devices. The term network may include the Internet, a local area network, a wide area network, or combinations thereof. The network may include one or more networks or communication systems, such as the Internet, the telephone system, satellite networks, cable television networks, and various other private and public networks. In addition, the connections may include wired connections (such as wires, cables, fiber optic lines, etc.), wireless connections, or combinations thereof. Furthermore, although not shown, other computers, systems, devices, and networks may also be connected to the network. Network refers to any set of devices or subsystems connected by links joining (directly or indirectly) a set of terminal nodes sharing resources located on or provided by network nodes. The computers use common communication protocols over digital interconnections to communicate with each other. For example, subsystems may comprise the cloud. Cloud refers to servers that are accessed over the Internet, and the software and databases that run on those servers.

Further, upon reaching various computer system components, program code in the form of computer-executable instructions or data structures can be transferred automatically from transmission computer-readable media to physical computer-readable storage media (or vice versa). For example, computer-executable instructions or data structures received over a network or data link can be buffered in RAM within a Network Interface Module (NIC), and then eventually transferred to computer system RAM and/or to less volatile computer-readable physical storage media at a computer system. Thus, computer system components that also (or even primarily) utilize transmission media may include computer-readable physical storage media.

Computer-executable instructions comprise, for example, instructions and data which cause a general purpose computer, special purpose computer, or special purpose processing device to perform a certain function or group of functions. The computer-executable instructions may be, for example, binary, intermediate format instructions such as assembly language, or even source code. Although the subject matter herein described is in a language specific to structural features and/or methodological acts, the described features or acts described do not limit the subject matter defined in the claims. Rather, the herein described features and acts are example forms of implementing the claims.

While this specification contains many specifics, these do not construe as limitations on the scope of the disclosure or of the claims, but as descriptions of features specific to particular implementations. A single implementation may implement certain features described in this specification in the context of separate implementations. Conversely, multiple implementations separately or in any suitable subcombination may implement various features described herein in the context of a single implementation. Moreover, although features described herein as acting in certain combinations and even initially claimed as such, one or more features from a claimed combination may in some cases be excised from the combination, and the claimed combination may be directed to a sub-combination or variation of a sub-combination.

Similarly, while operations depicted herein in the drawings in a particular order to achieve desired results, this should not be understood as requiring that such operations be performed in the particular order shown or in sequential order or that all illustrated operations be performed, to achieve desirable results. In certain circumstances, multitasking and parallel processing may be advantageous. Moreover, the separation of various system components in the implementations should not be understood as requiring such separation in all implementations, and it should be understood that the described program components and systems may be integrated together in a single software product or packaged into multiple software products.

Even though particular combinations of features are recited in the claims and/or disclosed in the specification, these combinations are not intended to limit the disclosure of possible implementations. Other implementations are within the scope of the claims. For example, the actions recited in the claims may be performed in a different order and still achieve desirable results. In fact, many of these features may be combined in ways not specifically recited in the claims and/or disclosed in the specification. Although each dependent claim may directly depend on only one claim, the disclosure of possible implementations includes each dependent claim in combination with every other claim in the claim set.

Further, a computer system including one or more processors and computer-readable media such as computer memory may practice the methods. In particular, one or more processors execute computer-executable instructions, stored in the computer memory, to perform various functions such as the acts recited in the embodiments.

Those skilled in the art will appreciate that the invention may be practiced in network computing environments with many types of computer system configurations including personal computers, desktop computers, laptop computers, message processors, hand-held devices, multi-processor systems, microprocessor-based or programmable consumer electronics, network PCs, minicomputers, mainframe computers, mobile telephones, PDAs, pagers, routers, switches, etc. Distributed system environments where local and remote computer systems, which are linked (either by hardwired data links, wireless data links, or by a combination of hardwired and wireless data links) through a network, both perform tasks may also practice the invention. In a distributed system environment, program modules may be located in both local and remote memory storage devices.

As used herein "Machine learning" refers to algorithms that give a computer the ability to learn without explicit programming, including algorithms that learn from and make predictions about data. Machine learning techniques include, but are not limited to, support vector machine, artificial neural network (ANN) (also referred to herein as a "neural net"), deep learning neural network, logistic regression, discriminant analysis, random forest, linear regression, rules-based machine learning, Naive Bayes, nearest neighbor, decision tree, decision tree learning, and hidden Markov, etc. For the purposes of clarity, part of a machine learning process can use algorithms such as linear regression or logistic regression. However, using linear regression or another algorithm as part of a machine learning process is distinct from performing a statistical analysis such as regression with a spreadsheet program. The machine learning process can continually learn and adjust the classifier as new data becomes available and does not rely on explicit or rules-based programming. The ANN may be featured with a feedback loop to adjust the system output dynamically as it learns from the new data as it becomes available. In machine learning, backpropagation and feedback loops are used to train the Artificial Intelligence/Machine Learning (AI/ML) model improving the model's accuracy and performance over time. Statistical modeling relies on finding relationships between variables (e.g., mathematical equations) to predict an outcome.

As used herein, the term "Data mining" is a process used to turn raw data into useful information. It is the process of analyzing large datasets to uncover hidden patterns, relationships, and insights that can be useful for decision-making and prediction.

As used herein, the term "Data acquisition" is the process of sampling signals that measure real world physical conditions and converting the resulting samples into digital numeric values that a computer manipulates. Data acquisition systems typically convert analog waveforms into digital values for processing. The components of data acquisition systems include sensors to convert physical parameters to electrical signals, signal conditioning circuitry to convert sensor signals into a form that can be converted to digital values, and analog-to-digital converters to convert conditioned sensor signals to digital values. Stand-alone data acquisition systems are often called data loggers.

As used herein, the term "Dashboard" is a type of interface that visualizes particular Key Performance Indicators (KPIs) for a specific goal or process. It is based on data visualization and infographics.

As used herein, a "Database" is a collection of organized information so that it can be easily accessed, managed, and updated. Computer databases typically contain aggregations of data records or files.

As used herein, the term "Data set" (or "Dataset") is a collection of data. In the case of tabular data, a data set corresponds to one or more database tables, where every column of a table represents a particular variable, and each row corresponds to a given record of the data set in question. The data set lists values for each of the variables, such as height and weight of an object, for each member of the data set. Each value is known as a datum. Data sets can also consist of a collection of documents or files.

The terms "non-transitory computer-readable medium" and "computer-readable medium" include a single medium or multiple media such as a centralized or distributed database, and/or associated caches and servers that store one or more sets of instructions. Further, the terms "non-transitory computer-readable medium" and "computer-readable medium" include any tangible medium that is capable of storing, encoding, or carrying a set of instructions for execution by a processor that, for example, when executed, cause a system to perform any one or more of the methods or operations disclosed herein. As used herein, the term "computer-readable medium" is expressly defined to include any type of computer-readable storage device and/or storage disk and to exclude propagating signals.

The term "application server" refers to a server that hosts applications or software that delivers a business application through a communication protocol. An application server framework is a service layer model. It includes software components available to a software developer through an application programming interface. It is system software that resides between the operating system (OS) on one side, the external resources such as a database management system (DBMS), communications and Internet services on another side, and the users' applications on the third side.

The term "cyber security" as used herein refers to application of technologies, processes, and controls to protect systems, networks, programs, devices, and data from cyber-attacks.

The term "cyber security module" as used herein refers to a module comprising application of technologies, processes, and controls to protect systems, networks, programs, devices and data from cyber-attacks and threats. It aims to reduce the risk of cyber-attacks and protect against the unauthorized exploitation of systems, networks, and technologies. It includes, but is not limited to, critical infrastructure security, application security, network security, cloud security, Internet of Things (IoT) security.

The term "encrypt" used herein refers to securing digital data using one or more mathematical techniques, along with a password or "key" used to decrypt the information. It refers to converting information or data into a code, especially to prevent unauthorized access. It may also refer to concealing information or data by converting it into a code. It may also be referred to as cipher, code, encipher, encode. A simple example is representing alphabets with numbers-say, 'A' is '01', 'B' is '02', and so on. For example, a message like "HELLO" will be encrypted as "0805121215," and this value will be transmitted over the network to the recipient(s).

The term "decrypt" used herein refers to the process of converting an encrypted message back to its original format. It is generally a reverse process of encryption. It decodes the encrypted information so that only an authorized user can decrypt the data because decryption requires a secret key or password. This term could be used to describe a method of unencrypting the data manually or unencrypting the data using the proper codes or keys.

The term "cyber security threat" used herein refers to any possible malicious attack that seeks to unlawfully access data, disrupt digital operations, or damage information. A malicious act includes but is not limited to damaging data, stealing data, or disrupting digital life in general. Cyber threats include, but are not limited to, malware, spyware, phishing attacks, ransomware, zero-day exploits, trojans, advanced persistent threats, wiper attacks, data manipulation, data destruction, rogue software, malvertising, unpatched software, computer viruses, man-in-the-middle attacks, data breaches, Denial of Service (DOS) attacks, and other attack vectors.

The term "hash value" used herein can be thought of as fingerprints for files. The contents of a file are processed through a cryptographic algorithm, and a unique numerical value, the hash value, is produced that identifies the contents of the file. If the contents are modified in any way, the value of the hash will also change significantly. Example algorithms used to produce hash values: the Message Digest-5 (MD5) algorithm and Secure Hash Algorithm-1 (SHA1).

The term "integrity check" as used herein refers to the checking for accuracy and consistency of system related files, data, etc. It may be performed using checking tools that can detect whether any critical system files have been changed, thus enabling the system administrator to look for unauthorized alteration of the system. For example, data integrity corresponds to the quality of data in the databases and to the level by which users examine data quality, integrity, and reliability. Data integrity checks verify that the data in the database is accurate, and functions as expected within a given application.

The term "alarm" as used herein refers to a trigger when a component in a system or the system fails or does not perform as expected. The system may enter an alarm state when a certain event occurs. An alarm indication signal is a visual signal to indicate the alarm state. For example, when a cyber security threat is detected, a system administrator may be alerted via sound alarm, a message, a glowing LED, a pop-up window, etc. Alarm indication signal may be reported downstream from a detecting device, to prevent adverse situations or cascading effects.

As used herein, the term "cryptographic protocol" is also known as security protocol or encryption protocol. It is an abstract or concrete protocol that performs a security-related function and applies cryptographic methods often as sequences of cryptographic primitives. A protocol describes how the algorithms should be used. A sufficiently detailed protocol includes details about data structures and representations, at which point it can be used to implement multiple, interoperable versions of a program. Cryptographic protocols are widely used for secure application-level data transport. A cryptographic protocol usually incorporates at least some of these aspects: key agreement or establishment, entity authentication, symmetric encryption, and message authentication material construction, secured application-level data transport, non-repudiation methods, secret sharing methods, and secure multi-party computation. Hashing algorithms may be used to verify the integrity of data. Secure Socket Layer (SSL) and Transport Layer Security (TLS), the successor to SSL, are cryptographic protocols that may be used by networking switches to secure data communications over a network.

The embodiments described herein can be directed to one or more of a system, a method, an apparatus, and/or a computer program product at any possible technical detail level of integration. The computer program product can include a computer-readable storage medium (or media) having computer-readable program instructions thereon for causing a processor to carry out aspects of the one or more embodiments described herein.

The flowcharts and block diagrams in the figures illustrate the architecture, functionality and/or operation of possible implementations of systems, computer-implementable methods and/or computer program products according to one or more embodiments described herein. In this regard, each block in the flowchart or block diagrams can represent a module, segment and/or portion of instructions, which comprises one or more executable instructions for implementing the specified logical function(s). In one or more alternative implementations, the functions noted in the blocks can occur out of the order noted in the Figures. For example, two blocks shown in succession can be executed substantially concurrently, and/or the blocks can sometimes be executed in the reverse order, depending upon the functionality involved. It will also be noted that each block of the block diagrams and/or flowchart illustration, and/or combinations of blocks in the block diagrams and/or flowchart illustration, can be implemented by special purpose hardware-based systems that can perform the specified functions and/or acts and/or carry out one or more combinations of special purpose hardware and/or computer instructions.

As used in this application, the terms "component," "system," "platform," "interface," and/or the like, can refer to and/or can include a computer-related entity or an entity related to an operational machine with one or more specific functionalities. The entities described herein can be either hardware, a combination of hardware and software, software, or software in execution. For example, a component can be, but is not limited to being, a process running on a processor, a processor, an object, an executable, a thread of execution, a program and/or a computer. By way of illustration, both an application running on a server and the server can be a component. One or more components can reside within a process and/or thread of execution and a component can be localized on one computer and/or distributed between two or more computers. In another example, respective components can execute from various computer-readable media having various data structures stored thereon. The components can communicate via local and/or remote processes such as in accordance with a signal having one or more data packets (e.g., data from one component interacting with another component in a local system, distributed system and/or across a network such as the Internet with other systems via the signal). As another example, a component can be an apparatus with specific functionality provided by mechanical parts operated by electric or electronic circuitry, which is operated by a software and/or firmware application executed by a processor. In such a case, the processor can be internal and/or external to the apparatus and can execute at least a part of the software and/or firmware application. As yet another example, a component can be an apparatus that provides specific functionality through electronic components without mechanical parts, where the electronic components can include a processor and/or other means to execute software and/or firmware that confers at least in part the functionality of the electronic components. In an aspect, a component can emulate an electronic component via a virtual machine, e.g., within a cloud computing system.

The embodiments described herein include mere examples of systems and computer-implemented methods. It is, of course, not possible to describe every conceivable combination of components and/or computer-implemented methods for purposes of describing the one or more embodiments, but one of ordinary skill in the art can recognize that many further combinations and/or permutations of the one or more embodiments are possible. Furthermore, to the extent that the terms "includes," "has," "possesses," and the like are used in the detailed description, claims, appendices and/or drawings such terms are intended to be inclusive in a manner similar to the term "comprising" as "comprising" is interpreted when employed as a transitional word in a claim.

The methods and techniques of the present disclosure are generally performed according to conventional methods well known in the art and as described in various general and more specific references that are cited and discussed throughout the present specification unless otherwise indicated. The nomenclatures used in connection with, and the procedures and techniques of embodiments herein, and other related fields described herein are those well-known and commonly used in the art.

The following terms and phrases, unless otherwise indicated, shall be understood to have the following meanings.

As used herein, the term "myopia", refers to a very common vision disorder or condition where distant objects appear blurry while close objects can be seen clearly. Myopia is also known as near-sightedness. The name originates from the Greek term "muopia," which means "close to the eyes."

As used herein, the term "ocular region" refers to the anatomical area encompassing the eyes and surrounding structures, which are vital for vision. This region may include the eyeball, or globe, with its various components such as the cornea, the transparent front layer covering the iris, pupil, and anterior chamber; the sclera, the white, opaque outer layer providing protection and form; and the iris, the colored part that controls the size of the pupil to regulate light entry. The pupil is the central opening in the iris, allowing light to reach the retina, while the lens, situated behind the pupil, focuses light onto the retina. The retina is the light-sensitive layer at the back of the eye, converting light into electrical signals sent to the brain via the optic nerve. Additionally, the ocular region may also include the choroid, a vascular layer between the retina and sclera, that supplies oxygen and nutrients to the eye. The ocular region may also include adnexa, or accessory structures, such as the eyelids, which protect the eyes and help spread tears over their surface, and the conjunctiva, a thin, transparent membrane covering the sclera and lining the inside of the eyelids. The lacrimal apparatus, comprising the lacrimal glands, ducts, sac, and nasolacrimal duct, is responsible for tear production and drainage. Furthermore, the lacrimal apparatus may include the extraocular muscles that play a crucial role in eye movement. These extraocular muscles include the superior rectus, which moves the eye upward; the inferior rectus, moving the eye downward; the medial rectus, moving the eye inward toward the nose; and the lateral rectus, moving the eye outward away from the nose. The superior oblique and inferior oblique muscles rotate the eye downward and outward, and upward and outward, respectively. The ocular region may also include the optic nerve, which is another component, transmitting visual information from the retina to the brain.

As used herein, the term "optic disc" refers to the optic nerve head, where nerve fibers from the retina converge and exit the eye.

As used herein, the term "optic disc size" refers to the diameter of the optic disc, which is the area where the optic nerve exits the eye. It is essential for assessing eye health.

As used herein, the term "Cup Disc Ratio (CDR)" refers to the proportion of the optic cup (the central depression within the optic disc) to the entire optic disc. A higher CDR may indicate glaucoma risk.

As used herein, the term "fundus" refers to the interior surface of the eye, including the retina, macula, blood vessels, and optic disc.

As used herein, the term "Intraocular Pressure (IOP)" refers to the pressure inside the eye. Elevated IOP can be a sign of glaucoma.

As used herein, the term "ocular alignment" refers to how well the eyes work together (binocular vision).

As used herein, the term "Best Corrected Visual Acuity (BCVA)" refers to the best vision a person can achieve with corrective lenses.

As used herein, the term "Spherical Power (SPH)" refers to the lens power needed to correct nearsightedness or farsightedness.

As used herein, the term "clinical data" refers to information related to the health status of patients and the care they receive within healthcare settings. This data encompasses a wide range of information collected during routine clinical care and is used for diagnosing, treating, and monitoring patients. Clinical data may include patient demographics, detailed medical history records, family medical history, known allergies. Clinical data may further include clinical observations made by healthcare, diagnostic test results, and treatment information, health monitoring data, behavioral and lifestyle information, and patient-reported outcomes. Clinical data may further include administrative data, including appointment schedules, billing information, insurance details, and patient referrals, and supports the efficient delivery of healthcare services.

As used herein, the term "medical data", may refer to data that include all that is included in clinical data and further include administrative data comprising insurance information, billing and insurance claims data, appointment and scheduling information, patient surveys, patient-reported outcomes and satisfaction.

As used herein, the term "Social determinants of health (SDOH)" refers to the conditions in which people are born, grow, live, work, and age that affect a wide range of health, functioning, and quality-of-life outcomes and risks. SDOH includes a broad range of factors, such as Economic Stability factors, Education factors, Social and Community Context factors, Health and Healthcare factors, and Neighborhood and Built Environment factors.

As used herein, the term "holistic health embedding" refers to a multidimensional representation of a user's health profile created by an AI model, enabling more accurate and personalized health predictions and interventions.

As used herein, the term "holistic health assessment" refers to a comprehensive evaluation approach that considers the individual as a whole, recognizing the interconnectedness of various factors that influence health, in this case eye health or holistic eye assessment. This approach often involves gathering detailed information about lifestyle, personal relationships, emotional health, and life satisfaction, alongside clinical data. By integrating these diverse elements, a holistic health assessment particular to eye health aims to provide a more complete picture of an individual's eye health, guiding personalized and more effective care strategies.

As used herein, the term "likelihood of myopia" also referred to as likelihood of nearsightedness, refers to the probability or chance that a person will develop myopia based on various factors.

As used herein, the term "degenerative myopia", also known as pathological or malignant myopia, refers to a severe form of nearsightedness (myopia) characterized by a progressive elongation of the eyeball that continues to worsen over time. This condition often leads to significant and potentially blinding complications due to the excessive stretching and thinning of the eye's structures.

As used herein, the term "systemic and environmental health data" refers to information that encompasses both the internal, biological aspects of health (systemic) and the external factors that can influence health (environmental). This type of data provides a comprehensive view of an individual's health by considering multiple dimensions that affect well-being.

As used herein, the term "curated dataset" is a collection of data that has been meticulously organized, cleaned, and verified for quality and relevance. This process involves data collection, data cleaning, data transformation, data integration, data validation, data annotation, data reduction, to ensure the dataset is accurate, consistent, and useful for analysis or modeling. The result of the curation process is a high-quality dataset that is ready for analysis, modeling, or other applications. Curated datasets are valuable because they reduce the noise and errors present in raw data, making it easier to derive meaningful insights and build reliable models.

As used here, the term "feature vector/s" are numerical representations of data used to capture the essential characteristics or attributes of input data in a format that algorithms can process. Each element in a feature vector represents a specific feature (or attribute) of the data, quantified in a way that is meaningful for analysis.

As used herein, "dynamic embedding adjustment" refers to the continuous and adaptive modification of embeddings, which are vector representations of data, in response to new information or changes in the underlying data distribution. This process allows the model to update its understanding and representation of input features dynamically, ensuring that the embeddings remain relevant and accurate over time.

As used herein, "longitudinal data"/"longitudinal patient data", refers to data that is collected over a period of time from the same subjects or entities. This type of data allows researchers to track changes and developments in the subjects' characteristics, behaviors, or conditions over time. Longitudinal data is particularly valuable for understanding trends, patterns, and causal relationships, as it provides insights into how variables evolve and interact over time.

As used herein, "chief complaints" refer to the primary concerns or symptoms that prompt a patient to seek medical attention from an ophthalmologist. These can include issues like blurred vision, eye pain, redness, double vision, floaters, headaches, light sensitivity, or difficulty seeing at night.

As used herein "present history" refers to the detailed account of a patient's current symptoms, duration, and any recent medical events or treatments relevant to their current visit, and progression of their condition leading up to the visit.

As used herein "past medical history" "refers to a comprehensive record of a person's medical conditions, illnesses, surgeries, treatments, and any significant medical events or procedures that have occurred throughout their lifetime up until the present time. It typically includes details such as chronic conditions (e.g., diabetes, hypertension), past surgeries, hospitalizations, allergies, immunizations, and medications taken in the past. Healthcare providers need this information to understand a patient's health status, make informed decisions about current medical care, and anticipate potential health risks or complications based on previous medical experiences.

As used herein "present clinical history" refers to the current and most recent medical information about a patient's health status and conditions. It includes details such as the symptoms the patient is currently experiencing, the duration and severity of these symptoms, any recent medical events or treatments, medications currently being taken, and any relevant changes in the patient's health since their last medical evaluation.

As used herein "eye care" refers to a range of medical and health services aimed at preserving and enhancing the health of the eyes and vision. It includes preventive measures such as regular eye exams to detect vision problems or eye diseases early, as well as treatments for various eye conditions and disorders.

As used herein "eye test compliance data" refers to the collection and analysis of information regarding how well patients adhere to recommended schedules for eye examinations and tests. This data includes metrics on whether patients attend their scheduled eye appointments, follow through with specific tests, and maintain the advised frequency of visits based on their individual eye health needs. It also encompasses factors influencing adherence, such as accessibility to eye care services, patient education, and socioeconomic conditions.

As used herein, "Non-Spherical Ocular Embeddings" refer to abnormalities in the shape of the eye's structural components, such as the cornea or lens, where these components deviate from a perfectly spherical shape. This irregularity can affect how light is focused onto the retina, leading to various visual distortions. These embeddings are critical in understanding and diagnosing refractive errors and other ocular conditions.

As used herein, "gender" refers to gender assigned at birth.

As used herein, "columns", when used in relation to data table or data analysis of patient records refers to feature or a characteristic.

As used herein, "feature engineering" with reference to artificial intelligence refers to the process of using domain knowledge to create input variables, or features, that make machine learning algorithms work more effectively. This process involves selecting, modifying, or creating new features from raw data to improve the performance and accuracy of predictive models. Effective feature engineering may significantly enhance the ability of machine learning models to identify patterns and make accurate predictions by providing them with the most relevant and informative variables.

As used herein, the term "dual pathway AI model" or "dual module framework" refers to an AI architecture that enables multimodal models encompassing vision, auditory, and language understanding simultaneously. It provides insights into complex processes by considering distinct pathways within a system.

As used herein, the term "multimodal fusion" refers to the process of combining information from multiple modalities (such as vision, language, and audio) to enhance understanding or analysis of a certain phenomenon or problem. It's a key component in multimodal learning, where different types of information are integrated.

As used herein, "multimodal data", refers to information that is derived from multiple sources or modalities, encompassing various forms of data such as text, images, audio, video, and sensor readings. This type of data integrates different types of information to provide a comprehensive and enriched representation of the underlying phenomena or entities being studied. In artificial intelligence and machine learning, multimodal data is utilized to improve the robustness and accuracy of models by leveraging the complementary strengths of different data types, enabling more nuanced and informed decision-making.

As used herein, "interconnected models" means that the outputs of one model are used as inputs or influence the processing of another model, creating a composite system where the models work together to achieve a more complex or refined task. This interconnection can enhance the overall system's performance by leveraging the strengths of each model, enabling the combination of different methodologies or perspectives. For example, in a multi-stage pipeline, one model may be responsible for preprocessing or feature extraction, while another model uses this processed data for final prediction or classification. The interconnection allows for more sophisticated and accurate results compared to using the models independently.

As used herein, "ground truth" refers to the accurate and objective data or information that serves as a benchmark for training, validating, and testing models. It represents the real-world facts or outcomes that the model aims to predict or classify. Ground truth is essential for evaluating the model's performance, as it provides a standard against which the model's predictions can be compared. High-quality ground truth data is crucial for developing robust and reliable AI models, as it ensures that the model learns and is assessed based on correct and relevant information.

As used herein, an "auxiliary target" refers to an additional objective or task that is integrated into the training process alongside the main task or primary target. This auxiliary target is often used to enhance the learning process of the model by providing supplementary information or regularization constraints. The primary goal of including auxiliary targets is to improve the overall performance, robustness, or generalization capabilities of the model. For example, in a multi-task learning scenario, where a model is trained to perform multiple related tasks simultaneously, each task can be considered an auxiliary target if they are not equally prioritized. The model learns to optimize both the main task and the auxiliary targets, leveraging shared representations and learning dependencies that can lead to better performance on all tasks. Auxiliary targets can also serve as regularization mechanisms, helping to prevent overfitting by guiding the learning process towards more generalizable solutions.

As used herein, "hyperparameters" refer to the external configurations that govern the learning process and structural composition of the model/model architecture, which are not derived from the training data itself. These hyperparameters are predetermined prior to the commencement of the training phase and are instrumental in shaping the model's performance and operational efficiency. Examples of hyperparameters include, but are not limited to, the learning rate, batch size, number of epochs, number of hidden layers, number of neurons per layer, dropout rates, and regularization parameters. Hyperparameters are distinct from model parameters, which are optimized during the training procedure to minimize a specified loss function. The tuning of hyperparameters is typically conducted using techniques such as grid search, random search, or more advanced optimization methods like Bayesian optimization. The meticulous selection and adjustment of hyperparameters is performed while developing AI models that effectively learn from the data and generalize well to novel, unseen instances.

As used herein, "calculated features" refer to new variables or attributes that are derived from the original raw data through mathematical, statistical, or logical transformations. These features are created to enhance the model's ability to learn patterns and make accurate predictions by providing more informative and relevant inputs. Calculated features can be the result of operations such as aggregation, normalization, scaling, encoding categorical variables, generating interaction terms, applying domain-specific functions, or utilizing other data preprocessing techniques. For instance, if the raw data includes timestamps, calculated features could include extracting the hour of the day, day of the week, or time intervals between events. By transforming the raw data into more meaningful and structured forms, calculated features help improve the performance, accuracy, and interpretability of AI models.

As used herein, "supplementary data" refers to additional data that is used to complement the primary dataset in order to enhance the performance, accuracy, and robustness of a model or analysis. This data may provide extra context, insights, or relevant information that is not captured in the primary dataset. Supplementary data can come from various sources and may include secondary datasets, external databases, metadata, or any other relevant information that aids in the understanding and processing of the primary data. For example, in a machine learning task to predict the likelihood of developing myopia (nearsightedness), supplementary data could include information such as genetic predisposition, time spent on near work activities (e.g., reading or screen time), outdoor activity levels, socioeconomic status, and environmental factors like urbanization and access to green spaces. By integrating such supplementary data, models can gain a more comprehensive understanding of the factors influencing the development of myopia, leading to better generalization and predictive performance.

As used herein, "generative AI" or generative artificial intelligence refers to Generative AI refers to a class of artificial intelligence models designed to generate new content, such as text, images, music, or even complex designs, that mimics human-like creativity. These models are capable of producing original outputs by learning from large datasets of existing content. The core technology behind generative AI often includes machine learning algorithms like Generative Adversarial Networks (GANs) and Variational Autoencoders (VAEs), as well as transformer-based models such as GPT (Generative Pre-trained Transformer). Generative AI, for example us used in creating realistic images and videos to generating natural language text. It leverages patterns and structures found in training data to create new, coherent, and contextually relevant outputs.

As used herein "user" of the system broadly refers to patients whose data is input in the system and/or clinicians who use the system to produce diagnosis or further analysis. When it is specified data of the user, it is referring to patient data.

Myopia has become a major public health concern due to its increased incidence across the globe. Almost half of the world's population is projected to be myopic by the year 2050 unless myopia control strategies are implemented. Occurrence of myopia is believed to be a combination of genetic, environmental, lifestyle factors, and refractive error changes. Further, visual stress, caused by spending too much time doing up-close activities, such as reading or doing computer work, may also be a contributing factor to myopia.

Myopia, also known as nearsightedness, is a common vision condition where distant objects appear blurry while close objects can be seen clearly. This may occur when the eye is elongated or the cornea is too curved, causing light entering the eye to focus in front of the retina rather than directly on it. Myopia is characterized by the inability to focus on distant objects, resulting from either elongated eyeballs or abnormal corneal curvature. Myopia in many cases may be corrected with eyeglasses, contact lenses, or surgery. But in rare cases, a progressive type called Degenerative Myopia develops that can be very serious and is a leading cause of blindness and affects about 2% of the population.

There is a significant number of myopia cases in children, with high severity primarily due to increased screen time, exposure to screen colors, and reduced outdoor activity. This trend is observed in both children and adults.

Business Problem: There is a high demand for early intervention and personalized treatment strategies for the prevention of nearsightedness by eye care professionals. Doctors may not have much time to listen and clearly understand various aspects of the health condition of each patient in a short interaction. Moreover, many patients may not be clear in informing about past health conditions clearly at the time of consultation with doctors. Most of the hospitals/primary health centers have inadequate infrastructure, with no proper mechanism for screening and monitoring the condition of the eye. Early screening and diagnosis of Myopia is essential in management of the health condition of the eyes. Further tracking of myopia progression is essential for retaining vision.

Business Solution: The current state of myopia detection at a doctor's office typically involves a series of standard eye exams and procedures conducted by eye care professionals, such as optometrists and ophthalmologists. The process begins with gathering information about the patient's vision problems, overall health, family history of myopia, and lifestyle. This is followed by a visual acuity test using an eye chart (Snellen chart) to measure the sharpness of vision at various distances. A refraction test is then conducted using a phoropter or autorefractor to measure the degree of refractive error and determine the appropriate lens prescription. Retinoscopy involves shining a light into the patient's eye and observing the reflection off the retina to estimate refractive error. A slit-lamp examination uses a microscope with a bright light to examine the structures of the eye, including the cornea, lens, and retina, for any abnormalities. Ophthalmoscopy is used to examine the back of the eye (fundus) to check the retina, optic disc, and blood vessels for signs of myopia or other conditions. Cycloplegic refraction, where eye drops are administered to temporarily paralyze the ciliary muscle and prevent accommodation, allows for a more accurate measurement of refractive error, especially in children. Corneal topography maps the surface curvature of the cornea to detect any irregularities that may contribute to myopia, and biometry measures the axial length of the eye using ultrasound or optical coherence biometry to assess the risk of myopia progression. Despite these thorough examinations, the current approach has limitations, such as time constraints due to high patient volumes, infrastructure limitations with many clinics lacking advanced diagnostic tools, and the subjectivity of some tests that rely on patient responses and examiner interpretation.

To address these limitations, the technological solution, i.e., integrating advanced technologies, such as artificial intelligence (AI) and machine learning models either as stand-alone or as an integrated part of one or more test equipment, to enhance the accuracy, efficiency, and personalization of myopia detection and management in clinical practice.

To determine a patient's risk of myopia effectively, hospitals need to be equipped with systems that utilize cutting-edge technology devices and tools with Artificial Intelligence (AI) based models. This technological advancement will facilitate early detection, personalized treatment plans, and continuous monitoring of myopia progression, ultimately enhancing patient care and outcomes in eye health management. The devices and tools would be equipped with the technological solution, i.e., the methods, models, and the systems that the current application is disclosing may help the doctors not only to detect the current myopia conditions, but also its severity and its future progress. If the current patient does not have myopia, then the system can predict a likelihood of myopia in future time periods. These things are currently not possible with the existing devices.

The business solution involves creating a suite of AI-driven tools that can be used by healthcare providers to identify individuals at risk of developing myopia and those at risk of myopia progression. These tools aim to facilitate early intervention, personalized treatment plans, and continuous monitoring to mitigate the adverse effects of myopia.

Technical Problem

Contribution of various genetic, environmental, and lifestyle factors to myopia, makes prediction of myopia complex and challenging. It is essential to identify patterns between ocular data, medical history, genetic factors, environmental factors, lifestyle factors and refractive errors to understand what factors are contributing to myopia and the progress in the magnitude of myopia. Detecting and predicting myopia presents several challenges that impact both patients and healthcare providers.

Firstly, early detection is crucial but often difficult with current technologies because the initial stages of myopia can be subtle and asymptomatic. Many children, who are most susceptible to developing myopia, may not realize they have vision problems and thus do not report symptoms. This can delay diagnosis and timely intervention.

Secondly, the accuracy of detection relies heavily on the skills and experience of eye care professionals. Variability in the quality of care and diagnostic equipment between different clinics can lead to inconsistent results.

Another challenge is the need for detailed patient history and various eye examinations, which can be time-consuming. Doctors often have limited time with each patient, making it difficult to conduct thorough assessments and gather all necessary information.

Monitoring the progression of myopia is also challenging. Myopia can progress at different rates in different individuals, and regular follow-up appointments are necessary to track changes in refractive error and axial length. This requires a consistent and long-term commitment from patients and their families, which can be difficult to maintain. Current regular follow-ups are time based, for example, every 3 months or every six months, irrespective of the rate of the progress in each individual. With the current technological solution, an automated schedule can be output by the system based on the individual's progress in myopia thus customizing follow-up appointments based on the individual's requirement.

Lastly, there is a need for more personalized treatment strategies. Myopia is influenced by a combination of genetic, lifestyle, and environmental factors, and effective management requires a tailored approach.

Current diagnostic methods do not fully capture the complexity of these factors, making it difficult to predict and manage myopia progression accurately. In order to improve myopia detection and management, it involves addressing these challenges through enhanced diagnostic techniques with the integration of advanced technologies like AI to support eye care professionals in making more accurate and personalized decisions.

Developing accurate and reliable AI models to detect the current eye condition and severity and predict the onset and progression of myopia involves handling large, complex datasets, integrating various clinical features, and ensuring the models' robustness and generalizability across diverse patient populations.

Technical Solution

Artificial Intelligence and Machine Learning (AI/ML) techniques are leveraged to analyze eye characteristics and predict myopia that can provide valuable insights for proactive eye care. In an embodiment, Myopia Informed Artificial Intelligence System, comprising detection and predictive models, are created that can identify users who are at risk of myopia. In an embodiment, machine learning models are utilized for early detection and prevention of myopia-related visual impairments. AI/ML models are built using various features that are contributing to myopia detection and progression, comprising the features extracted from the left and/or right eyes of the patient/user.

By analyzing and understanding features in the patient data and determining various patterns using various AI/ML methods and models, it is important to identify patients who already have myopia and are at risk of its progression, enabling timely and targeted interventions to manage and mitigate the condition effectively. Additionally, the AI/ML methods also assess their further progression in the future. Further, with the AI/ML systems, methods and models, help eye care professionals identify patients at risk of developing myopia in the future, even if they do not have the condition at the time of the test but show a likelihood of developing it.

The technical solution includes developing machine learning models using clinical data such as gender, age, chief complaints, present history, visual acuity (unaided and corrected), fundus examination results, and baseline spherical and cylindrical refraction measurements. These models leverage logistic regression, support vector machines (SVM), K-nearest neighbors, decision trees, and ensemble methods like random forests, extra trees, and bagging to predict myopia development and progression.

Technical challenges: AI/ML models rely on patient data available in patient records for training. Data captured and preserved at primary health centers in digital records has issues with completeness, consistency, data formats, ranges of values, integrity issues with other factors and treatments. The escalating need for early intervention and personalized treatment strategies in the management of nearsightedness (myopia) underscores a significant challenge in eye care. Traditional diagnostic methods often fail to integrate and analyze complex interactions between ocular data and patient medical histories comprehensively. This limitation hinders the precision in early detection, risk assessment, and management of myopia, and impacts patient care outcomes.

Developing models that accurately predict future myopia risk while also detecting current myopia involves solving significant technical challenges, including data quality, feature selection, model training, and validation.

Technical Result

The effectiveness of the Myopia Informed Artificial Intelligence System has been validated clinically against patient records over follow-up visits, showing significant promise in the early detection of myopia. This not only aids in better management but also in strategic planning for potential surgical interventions, all tailored to individual patient needs based on comprehensive data analysis.

The technical result further comprises deployment of predictive models that can identify patients at risk of myopia development and progression with a predefined accuracy. The models provide scores indicating the likelihood of myopia progression and development, helping clinicians make informed decisions about preventive and corrective measures.

The effectiveness of the Myopia Informed Artificial Intelligence System has been validated against patients' records having 1-year follow up visits with ophthalmologists' assessment regarding myopia and AI/ML models show promising performance in early detection of myopia, prediction of likelihood of myopia and progress of myopia.

Significant benefits arise from the risk scores generated by myopia-informed AI models, providing guidance for the schedule management of patients who are at risk of myopia. This scheduled management, which considers the magnitude of myopia and socio-economic conditions of the patient, enables efficient eye care, including medication plans and plans for potential surgeries. The outcomes of the Myopia informed AI system, when combined with the professional judgment of ophthalmologists, enhance clinical decision-making and eye care management, ultimately leading to improved patient outcomes.

Technical Details Specific to the Technical Solution

In an embodiment, Myopia Informed Artificial Intelligence System addresses these challenges through a dual module framework, utilizing advanced AI-driven analysis for a comprehensive ocular health assessment.

The Myopia Informed Artificial Intelligence System comprises a dual-pathway AI model or a dual module framework employing separate but interconnected neural networks in the two modules: Module 1, focuses on future risk of myopia and progression assessment of myopia; and Module 2 is tailored for ongoing risk evaluation as in detecting current myopia, its severity and progression rate along with the development of personalized treatment and management strategies. The system employs machine learning and deep learning techniques to analyze eye images, either digital or physical images, and patient data, enhancing the accuracy of myopia detection and progression predictions.

According to an embodiment, it is a Myopia Informed Artificial Intelligence System comprising a dual module framework.

FIG. 1A shows the Myopia Informed Artificial Intelligence System comprising a dual module framework according to an embodiment. The figure illustrates a framework for utilizing artificial intelligence (AI)/Machine Learning (ML) to predict and manage myopia by integrating various types of data through several processing modules. The process can be broken down into four main modules: Input Module 102, Preprocessing Module 104, Machine Learning (ML) Training and Inference Module 106, Output Module 108, and Inference and Feedback Loop 110.

Input Module 102: This module is responsible for collecting the raw data required for the analysis. It comprises two primary data sources:

Clinical and Medical Data: This includes clinical and medical records of patients, such as their medical history, genetic information, and other relevant health data.

Eye Images/Digital Images: This involves capturing digital images of the eye, including retinal scans and other ocular imaging data.

In an embodiment, it may also comprise other social and economic factors that influence the health of a patient. In an embodiment, it comprises lifestyle and work related parameters or external factors comprising screen exposure time, screen distance from eyes, screen brightness settings usually used by the patients, screen size used, screen size variations within a day etc. Screen size variations comprise whether the patient uses smartphone, tablet, laptop, big screen, or all of them etc., and for how long and how frequent, outdoor activity time, etc.

Preprocessing Module 104: This module prepares the raw data for analysis by performing necessary preprocessing tasks. It comprises of two parallel systems:

Data Preprocessing System: This system cleans and organizes the clinical and medical data, ensuring consistency and accuracy. It handles tasks such as data normalization, standardization, and dealing with missing values.

Image Processing System: This system processes the images of the eye, extracting important features and ensuring the images are in a suitable format for analysis. It might involve image enhancement, segmentation, and feature extraction.

ML Training and Inference Module 106: This module is where the machine learning models are trained and applied to make predictions. It comprises:

Data Fusion Module: This module combines the preprocessed clinical, medical, and imaging data into a unified dataset that is used for training and inference. The integration of different data types ensures a comprehensive analysis.

Machine Learning Module: This module comprises one or more AI and machine learning models that analyze the fused data. These models are trained on datasets to identify patterns and make predictions regarding myopia. Such trained models may be referred to as pre-trained models or trained models.

Output Module 108: The results from the machine learning models are used to provide actionable insights. This module includes:

Personalized Insights: Customized information on myopia for each patient based on their unique data.

Likelihood of Myopia: Predictions about the probability of developing myopia.

Severity of Myopia: Assessments of the current severity of myopia in patients.

Progression of Myopia: Predictions about how the condition might progress over time.

Scheduled Care Interventions: Recommendations for personalized care interventions, which could include treatment plans, lifestyle changes, and follow-up schedules based on the predictions and insights.

Inference and Feedback Loop 110: The figure indicates an inference pathway where predictions and insights are generated and fed back into the system for further refinement and improvement of the AI models. This feedback loop helps in continuously improving the accuracy and reliability of the predictions by learning from new data and outcomes.

Representation Learning: Performance of the prediction model depends upon the quality of data pooled for training the model. Deep neural network models are trained to learn data representation for the data considered as the input. To improve the performance of the prediction model, vector representation can be adopted to denote the content in the medical records. Furthermore, information extracted from clinical notes and eye scans are also combined with the other characteristics of the data and are represented as vectors.

Learning and Extracting from Text Data: The AI suite of the Myopia Informed Artificial Intelligence System has neural network models of type recurrent neural networks to perform the task of extracting information from the unstructured data such as lab reports, Clinician's notes etc. Models can be trained to identify the clinical concepts in text and map them to the standard clinical approaches. Thereby trained models enable transformation of unstructured text to information represented in vectors. Using Natural Language Processing (NLP) techniques to analyze the data from present history, past medical history, chief complaints to offer a robust solution for extracting key medical information. This approach supports clinical decision-making by transforming unstructured text into actionable insights, thereby enhancing patient care and operational efficiency. In an embodiment, doctors' notes, patients question and answers inputs regarding the screen time exposure, lifestyle etc., may also be part of present history.

Learning & Extracting from Image Data: The AI suite of the Myopia Informed Artificial Intelligence System comprises deep neural network models of type convolutional neural networks to perform the extraction of information from different types of images of eye scans such as Fundus Photography, Optical Coherence Tomography (OCT), Fluorescein Angiography, Indocyanine Green Angiography (ICG), Ultrasound Imaging, Anterior Segment Photography, Corneal Topography, Confocal Microscopy, Retinal Tomography, Autofluorescence Imaging, Specular Microscopy, Electroretinography (ERG) Imaging etc. Networks are trained to learn object segmentation from the scanned images. Once trained, the model has the ability to detect objects from the knowledge it has gained about image features. Upon extraction of the object from the scanned image, information about the properties of the object are represented in vectors.

Learning to Predict the Myopia Informed Artificial Intelligence System Eye Condition Risk Score Information extracted from the above deep neural networks can then be passed to the stacked neural networks with deep hidden layers. These layers have a large number of nodes with non-linear activation functions and thus have the ability to capture the non-linear association with the various data characteristics of the patient. Projection of a patient's characteristics to the higher dimension will enhance the opportunity to better understand the association between different characteristics. Training of the model is done in the context of supervised learning. Consequently, the model's ability to identify and extract patterns from the patient's characteristics pertaining to an eye condition (myopia) risk can be reliable with statistical significance. Further, training of the entire stacked deep network can be repeated to identify optimal values of epochs and batch size.

Techniques such as dropout and regularization can be utilized to reduce the bias in the model's prediction and increase its capability to generalize knowledge from the various characteristics to predict a risk. Further, the model's hyper parameters such as depth of the network, dimensions, learning rate and momentum can be fine-tuned to improve their power of predictability of risk by leveraging the optimization techniques including, but not limited to, gradient descent, stochastic gradient descent and their flavors.

Each model in the Myopia Informed Artificial Intelligence System computes a risk score for risk of developing myopia, risk of progression of myopia, severity of myopia, risk of likelihood of myopia in future, progression of myopia, to provide a measure that comprehensively summarizes the eye health score. The Myopia Informed Artificial Intelligence System, in various embodiments of the claimed invention can then compute the overall eye health score using statistical techniques that derive the score from each of the above models.

Risk Stratification and Insight Delivery: To increase the viability of score interpretation, the prediction results can be stratified into Low, Medium and High. This is done by the Myopia Informed Artificial Intelligence System by employing one or more statistical techniques to perform operations such as normalization, standardization of predicted values and identification of thresholds to classify a risk score as low, medium and high. Such a classification of risk score, in various embodiments of the claimed invention, can help in easy and consistent assessment and interpretation of eye health by all the stake holders of the healthcare system.

Feed-back layer: In addition, the Myopia Informed Artificial Intelligence System also provides its algorithms with the self-learning capabilities to learn continuously from the data provided. Such an ability in various embodiments of the claimed invention can be potentially useful in identifying and designing optimal intervention/treatment strategies, such as lifestyle modifications, corrective lenses, or medical treatments, and/or for scheduling appointments at the right time such that the patient is continuously monitored and intervened to avoid any critical situation. Early prediction and subsequent preventive measures contribute to better long-term vision health and reduces the risk of severe myopic complications, such as retinal detachment or glaucoma. Predictive models further help in the efficient allocation of healthcare resources by focusing on high-risk individuals, thereby optimizing screening and monitoring efforts.

Figure 1B:
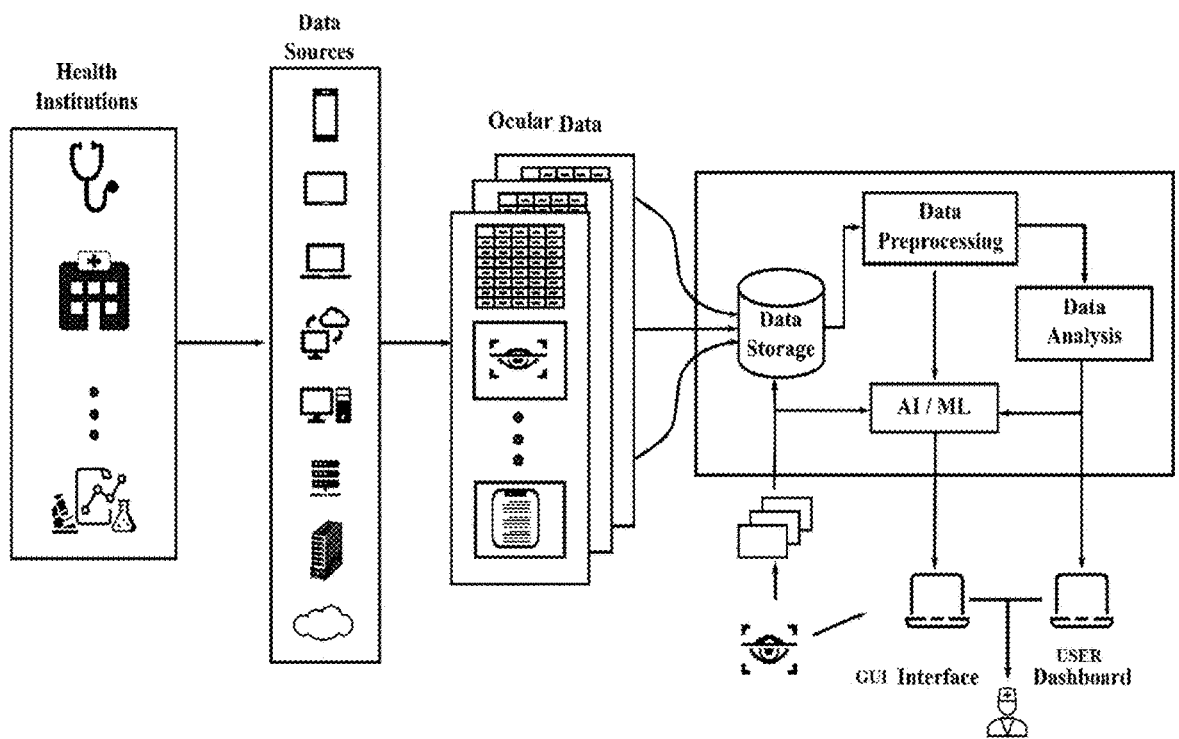
FIG. 1B shows the overview of the Myopia Informed Artificial Intelligence System according to an embodiment.

FIG. 1B shows the overview of the Myopia Informed Artificial Intelligence System according to an embodiment. Designing and developing a complex computation system for predicting risks utilizes a software ecosystem/platform with robust computational infrastructure encompassing components for:

Gathering data from multiple data sources such as health institutions, data bases, electronic health records, and ocular data from clinics, data generated or observations/notes made by Nurses, Doctors, Clinicians, Labs, Hospitals, health institutions etc.;

Using diverse technologies for collection, processing, storage and distribution of data such as Smartphones, iPad®s, Desktop/Personal Computers, Stand-alone/On-Premise/Cloud Servers etc.;

Organizing data in a data storage system and in auxiliary storage devices, wherein auxiliary storage devices include hard disk drives (HDDs), solid-state drives (SSDs), optical discs (CDs, DVDs, Blu-ray discs), Universal Serial Bus (USB) flash drives, external hard drives, memory cards (Secure Digital (SD) cards, microSD cards), network attached storage (NAS), and cloud storage.;

Data preprocessing analytics; Cleansing of data stored in databases is known to improve performance of subsequent processes (analytics and prediction) in the pipeline;

Dashboard for rendering insights from analytics;

A suite of Artificial Intelligence (AI) and Machine Learning (ML) models for learning knowledge to predict risks; and Web interface that displays eye health given the ocular data of the patient using the knowledge from AI algorithms.

Input-Data Acquisition

Myopia Informed Artificial Intelligence System acquires data from multiple sources as the patient's eye characteristics are captured and stored by different entities at various places, multiple times. In general, eye health prediction characteristics are categorized under medical, clinical, ocular, demographic, lifestyle, and genetic.

Each of these characteristics are captured in different data formats. Some of these characteristics are stored in a structured format/represented tabularly. However, information about laboratory tests and results are represented as reports while Clinicians' notes are often textual, audio, video files. Furthermore, all of the patients' medical scans are in image format. Some of the clinical characteristics can be captured and stored in a data format such as CSV/Excel/JSON/XML/PDF/TXT, but eye scans are stored in unstructured image format. Further, summarization of textual data from laboratory reports and clinical notes can be performed by applying pre-processing techniques.

The Myopia Informed Artificial Intelligence System leverages a suite of Machine/Deep Learning algorithms for exploration of factors associated with risks and subsequently computes the scores for various types of risks. The system adopts and stacks numerous techniques for performing the tasks such as pre-processing, exploratory analysis and prediction of risk score.

Figure 1C:
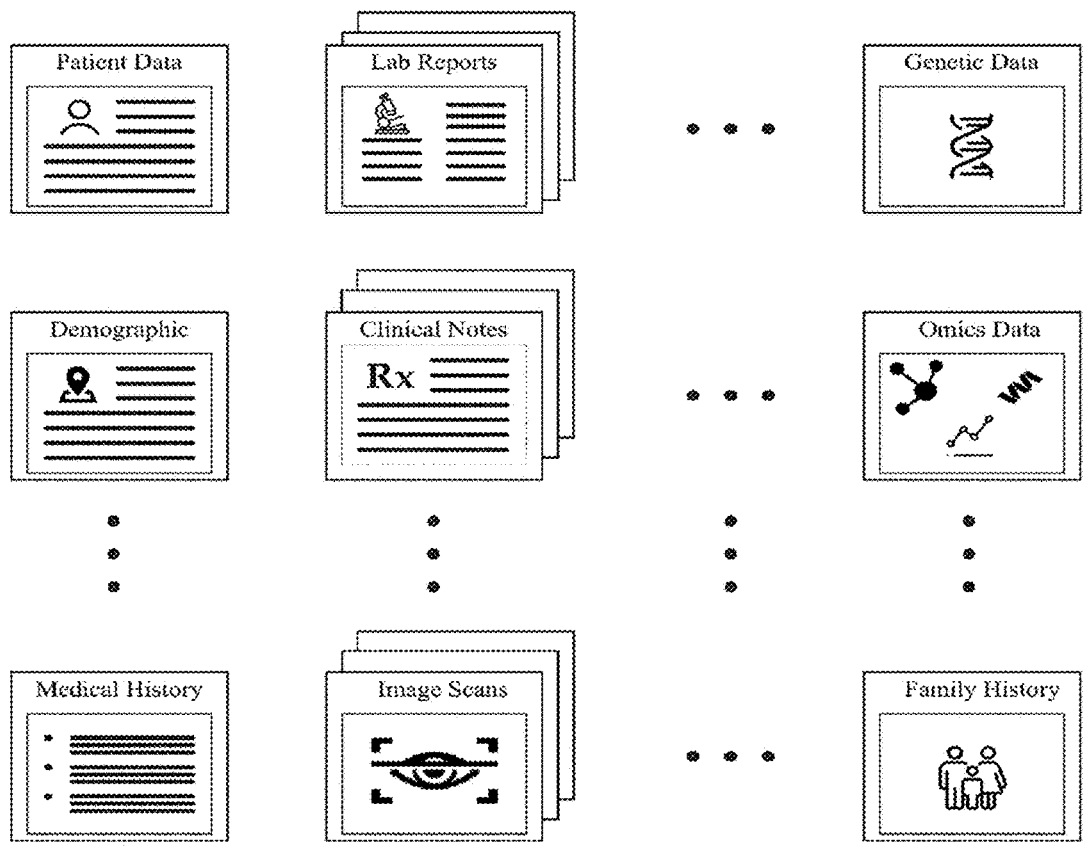
FIG. 1C shows the patient records and patient data obtained from multiple sources and according to an embodiment.

FIG. 1C shows the patient records and patient data obtained from multiple sources according to an embodiment. The data formats vary between sources depending upon how the data is stored and organized. Medical data may be inconsistent due to the nature of data acquisition processes and diversity of the nature of data. Further, data may contain noise, which refers to irrelevant, redundant, or erroneous information that can obscure meaningful insights and affect the accuracy and quality of data analysis.

Therefore, the Myopia Informed Artificial Intelligence System runs its pre-processing algorithms that deal with processing both structured and unstructured data. These algorithms pre-process the structured, unstructured, and image data and then forward the cleaned data to the subsequent modules for further processing and analysis. Some of the challenges in cleaning medical data and pre-processing approaches are:

Structured Data

Data Inaccuracy—handling the incomplete, missing values can be done using traditional techniques such as imputation with mean, normal values and also with model-based approaches such as multivariate regression and k-nearest neighbor.

Data Noise—reducing noise by removing erroneous data and outliers from the data by multivariate approaches using different similarity measures such as Mahalanobis and Cook.

Data Inconsistency—identified when data is input from various sources. During this time the source with the most inconsistent data can be identified and can be addressed using correlation analysis.

Unstructured Data

Dr. Notes/Text: For textual data the normalization can be a task for analysis of clinical notes and patient's laboratory reports. With normalization, Myopia Informed Artificial Intelligence System handles some of the challenges in text processing such as:

Format/Code Conversion—data from multiple sources in various formats/codes can be collected and converted to simple format. Myopia Informed Artificial Intelligence System incorporates Scripts for converting files in different formats to one standard format.

Eliminating Stop Words/Punctuations/Non-ASCII characters—Myopia Informed Artificial Intelligence System incorporates regular expression scripts to eliminate the stop words, punctuations and non-ascii characters.

Identifying Stem Words—reducing each word in the text to base or root will improve the analysis of textual data. Myopia Informed Artificial Intelligence System comprises modules for performing stemming on clinical and laboratory notes.

Lemmatization—as used herein can refer to reducing words to base form by considering the context along with the content. This is known as lemmatization and can be useful in identifying clinical, biological entities in notes or reports. Alternatively, lemmatization of words helps to tag the text.

Medical Scans/Images

For processing medical images, the Myopia Informed Artificial Intelligence System can provide modules to perform the following tasks:

Image Resize & Normalization—Images of different patients collected from different sources usually have different dimensions that are to be resized. According to various embodiments the Myopia Informed Artificial Intelligence System encompasses methods such as nearest neighbor and neural networks to perform up-scaling and down-scaling of images and also methods for transformation.

Noise Reduction—Noise in the medical images occurs due to variations in capturing and can be undesirable for image analysis. Therefore, the Myopia Informed Artificial Intelligence System comprises techniques that support reduction of various types of noises including, but not limited to, Pepper, Gaussian and Poisson. According to various embodiments the Myopia Informed Artificial Intelligence System comprises Neural networks-based modules to suppress the noise in scanned images.

Blur—Along with noise the other major distorter for quality of an image is blur which results in affecting the accuracy of the prediction models. According to an embodiment the Myopia Informed Artificial Intelligence System comprises Kernel filters such as gaussian blur, deep neural networks, to sharpen and blur the images during the training of the prediction model. Consequently, during real time prediction, the model will have acquired resistance to blurring in the medical images.

EDA—Exploratory Data Analysis: Myopia Informed Artificial Intelligence System also considers the synthesized results pertaining to the factors associated with myopia and progression of myopia. These results can show the incidence and prevalence of the factors for risks besides providing deep insights into understanding the behavior of risk factors for different cohorts. Clinicians can use such an exploratory analysis in designing the prevention and intervention strategies. Results can be rendered by rich graphical presentations through a dashboard that enables easy interpretation and assessment of risk indicators. Some of the visualizations rendered in the dashboard include, but are not limited to:

Visualization of indicators for myopia and/or its degradation may particularly show factors such as Genetic Factors, Environmental Factors, Lifestyle Factors, Educational Demands, Optical Factors, Biological Factors, Systemic Health. These are usually depicted using speedometers, gauge meter, and horizontal bar charts or any relevant chart that can depict the information clear and concise. Prevalence of certain risk factors by demographic, genetic, and lifestyle factors of patients can be illustrated using distribution charts, box plots, violin plots, pie and bar charts; these are not shown in the figures but are in the knowledge of a person of ordinary skill in the art.

The Myopia Informed Artificial Intelligence System is designed to enhance the prediction and management of users' myopia data through the integration of diverse data sources and advanced machine learning techniques.

FIG. 2A shows patient data comprising ocular features according to an embodiment. Myopia Informed Artificial Intelligence System is designed to process diverse data sets comprising one or more of ocular characteristics/ocular data, systemic data, environmental health data, behavioral data, clinical data, medical data, social determinants of health, and patient-reported information.

The ocular data or features related to eye health and vision assessment used for diagnosing and managing various ocular conditions along with their definitions are:

Optic Disc Size: The optic disc, or optic nerve head, is the point in the eye where the optic nerve fibers exit the retina. The optic disc size refers to the diameter of this structure, which can vary among individuals and is measured during eye examinations.

Cup-Disc Ratio: This ratio compares the diameter of the optic cup (the central depression within the optic disc) to the diameter of the entire optic disc. It is a measurement performed in assessing glaucoma; a higher ratio may indicate glaucomatous damage.

Optic Disc: The optic disc is the visible part of the optic nerve located at the back of the eye. It is the point where the nerve fibers, from the retina, converge to form the optic nerve, which transmits visual information to the brain.

Fundus: The fundus of the eye is the interior surface opposite the lens, including the retina, optic disc, macula, fovea, and posterior pole. It is examined during an eye examination using ophthalmoscopy to check for retinal health and diagnose various conditions.

Intraocular Pressure (IOP): IOP refers to the fluid pressure inside the eye. It is a measurement performed in diagnosing and managing glaucoma. Elevated IOP can lead to optic nerve damage and vision loss.

Ocular Alignment: This term describes the positioning of the eyes in relation to each other. Proper ocular alignment ensures that both eyes are directed at the same point. Misalignment can result in conditions such as strabismus.

Tor CA Unaided: This likely refers to "Toric Cylinder Axis unaided," which describes the orientation of astigmatism (measured in degrees) without corrective lenses.

Best Corrected Visual Acuity (BCVA): BCVA is the sharpest vision a person can achieve with the help of corrective lenses (glasses or contact lenses). It is a measure used in determining the effectiveness of visual correction.

Spherical (SPH): SPH indicates the degree of nearsightedness or farsightedness in an eye prescription. A negative value indicates myopia (nearsightedness), while a positive value indicates hyperopia (farsightedness).

Cylindrical (CYL): CYL refers to the degree of astigmatism in an eye prescription, which is caused by an irregularly shaped cornea or lens. It measures the amount of lens power needed to correct the astigmatism.

Tor FR Corr Axis: This refers to "Toric Front Corrected Axis," which describes the orientation of the cylindrical correction for astigmatism on the front surface of a corrective lens.

Systemic health data pertains to the internal functioning of the body and includes information about various systems and processes. Examples include:

Biological Markers: Blood pressure, cholesterol levels, glucose levels, hormone levels.

Medical History: Past and current illnesses, surgeries, family medical history.

Genetic Information: DNA sequences, genetic mutations or predispositions.

Physiological Measurements: Heart rate, respiratory rate, body temperature.

Chronic Conditions: Presence of diseases like diabetes, hypertension, asthma.

Environmental health data/Environmental data focuses on external factors that can affect an individual's health. Examples include:

Air Quality: Levels of pollutants like Particulate Matter (PM) 2.5, PM10, ozone, carbon monoxide.

Water Quality: Presence of contaminants, pH levels, mineral content.

Exposure to Toxins: Pesticides, heavy metals, radiation.

Living Conditions: Housing quality, neighborhood safety, access to clean water and sanitation.

Climate Factors: Temperature, humidity, Ultra Violet (UV) exposure, bright light exposure, extreme weather events.

Socioeconomic Factors: Income level, education, employment status, access to healthcare.

Lifestyle Factors: Diet, physical activity, screen time exposure, sitting posture, smoking, alcohol consumption.

Behavioral data comprises personal habits and lifestyle choices that directly impact health. Examples include:

Diet: Nutritional intake, balanced diet, choices of diet etc.

Physical Activity: Regular exercise, maintaining a healthy weight, Body Mass Index (BMI) etc.

Sleep Patterns: sleep quality, insufficient sleep, quality of sleep.

Screen Time: Excessive screen time, poor posture, sedentary lifestyle etc.

Smoking and Alcohol Consumption: amount of consumption of alcoholic material and quantity consumed etc.

Clinical and medical data: Clinical data is a subset of medical data, where clinical data focuses specifically on patient care and clinical encounters, and medical data includes a wider array of health-related information. Both types of data are essential for comprehensive healthcare delivery, research, and the development of health interventions. Clinical data is essential for healthcare providers to make informed decisions about patient care, develop personalized treatment plans, and monitor the effectiveness of interventions. Additionally, clinical data may help to identify trends, improve healthcare practices, and advance medical knowledge. Clinical data management may involve the use of systems designed to ensure accuracy, maintain privacy, and enhance security. In an embodiment, clinical data and medical data may be used interchangeably.

Clinical data encompasses a wide range of information collected during routine clinical care and is used for diagnosing, treating, and monitoring patients. Clinical data may include patient demographics, such as age, gender, ethnicity, and contact details, medical history records that document past illnesses, surgeries, chronic conditions, family medical history, and known allergies. Clinical data may further include clinical observations made by healthcare providers during patient visits, including symptoms, physical examination findings, and vital signs like blood pressure, heart rate, temperature, and respiratory rate. Clinical data may further include diagnostic test results, including outcomes from laboratory tests, imaging studies, and other diagnostic procedures, providing essential information for diagnosis and treatment planning. Clinical data may further include treatment information, detailing medications prescribed, dosages, duration of treatment, surgical procedures performed, and other therapeutic interventions. Clinical data may further include health monitoring data, collected continuously or periodically from patient monitoring devices such as blood glucose monitors, blood pressure cuffs, and wearable devices tracking physical activity and other health metrics, and offers ongoing insights into a patient's health status. Clinical data may further include behavioral and lifestyle information, including data on diet, exercise habits, smoking status, and alcohol consumption, and contributes to a comprehensive understanding of a patient's health. Patient-reported outcomes, which provide information directly from patients about their health status, symptoms, quality of life, and satisfaction with care. Clinical data may further include administrative data, including appointment schedules, billing information, insurance details, and patient referrals to support the efficient delivery of healthcare services.

Medical data may refer to all the data that is included in clinical data such as Patient Demographics data comprising age, gender, ethnicity, contact information; medical history data comprising previous diagnoses, surgical history, family medical history, allergies; clinical data comprising, symptoms, physical examination findings, vital signs (e.g., blood pressure, heart rate), clinical notes from healthcare providers; diagnostic data comprising laboratory test results (e.g., blood tests, urinalysis), imaging studies (e.g., X-rays, Magnetic Resonance Imaging (MRIs), Computed Tomography (CT) scans), biopsy results, genetic testing, treatment data comprising medications prescribed and administered, treatment plans, therapy and rehabilitation records, surgical procedures performed; health monitoring data comprising data from wearable devices (e.g., heart rate monitors, fitness trackers), home health monitoring (e.g., blood glucose levels, blood pressure readings), telehealth consultations; behavioral data comprising lifestyle information (e.g., diet, exercise habits), substance use (e.g., smoking, alcohol consumption); administrative data comprising insurance information, billing and claims data, appointment and scheduling information; outcome data comprising treatment outcomes, recovery progress, patient-reported outcomes and satisfaction.

Social determinants of health (SDOH) are the conditions in which people are born, grow, live, work, and age that affect a wide range of health, functioning, and quality-of-life outcomes and risks. SDOH includes a broad range of factors, such as economic stability factors comprising employment status, income level, financial security, poverty levels; education factors comprising access to quality education, educational attainment, literacy and language proficiency, early childhood education and development; social and community context factors comprising social cohesion and support networks, discrimination and social exclusion, civic participation, community safety and trust; health and healthcare factors comprising access to healthcare services, quality of healthcare services, health literacy, availability of health insurance; neighborhood and built environment factors comprising quality of housing and living conditions, access to healthy foods, environmental conditions (pollution, green spaces), transportation options and infrastructure, neighborhood crime and violence rates.

Myopia is influenced by a complex interplay of genetic and environmental factors. Genetically, numerous elements contribute to the development and progression of myopia. Several specific genes, such as Paired Box 6 (PAX6), Zinc Finger E-box Binding Homeobox 1B (ZFHX1B), and Membrane Frizzled-Related Protein (MFRP), have been identified as playing crucial roles in eye development and growth. These genes, along with numerous single nucleotide polymorphisms (SNPs) revealed through genome-wide association studies (GWAS), underscore the genetic basis of myopia. For instance, variants in genes like Gap Junction Protein Delta 2 (GJD2) and Retinol Dehydrogenase 5 (RDH5) have been strongly associated with higher risks of developing myopia. Heritability studies further highlight the genetic influence, with a significantly increased likelihood of developing myopia if one or both parents are myopic. Twin studies bolster this understanding, demonstrating a higher concordance of myopia among identical twins compared to fraternal twins. Genes regulating the structure and function of the eye, such as those involved in eye growth regulation and the remodeling of the retina and sclera, are studied and contribute to genetic data. Abnormalities in these genes can lead to the elongation of the eyeball, a key characteristic of myopia. Moreover, genes related to collagen synthesis and the extracellular matrix, such as Collagen Type II Alpha 1 Chain (COL2A1) and Lysyl Oxidase Like 1 (LOXL1), play a significant role in maintaining the structural integrity of the eye, and their mutations can contribute to abnormal eye growth. Additionally, specific chromosomal regions, or loci, have been linked to myopia, with loci on chromosomes 2, 4, 8, 11, 12, 18, and 22 being particularly significant. The function of photoreceptors and the eye's response to light, influenced by genes like Retinal G Protein-Coupled Receptor (RGR) and Glutamate Metabotropic Receptor 6 (GRM6), also play a role in how the eye grows and focuses. Circadian rhythm genes, such as Circadian Locomotor Output Cycles Kaput (CLOCK) and Aryl Hydrocarbon Receptor Nuclear Translocator Like (ARNTL), which regulate the body's response to light and darkness, are similarly implicated in myopia development. The ability of the eye to focus and refract light is governed by genes involved in accommodation; and the shape of the lens and cornea, such as Crystallin Alpha A (CRYAA) and Zinc Finger CCCH-Type Containing 11B (ZC3H11B), is another crucial aspect of myopia's genetic foundation. Moreover, signaling pathways and growth factors, particularly those related to Transforming Growth Factor Beta (TGF-β) and Insulin-like Growth Factor 1 (IGF-1), play important roles in the development and remodeling of ocular tissues and are integral to understanding the genetic underpinnings of myopia. Such genetic factors as described and those which are not described but known will be provided as an input for eye prediction assessments.

FIG. 2B shows different types of data and elements present in the data according to an embodiment. The data elements are as shown in the table provided in the figure.

Figure 3:
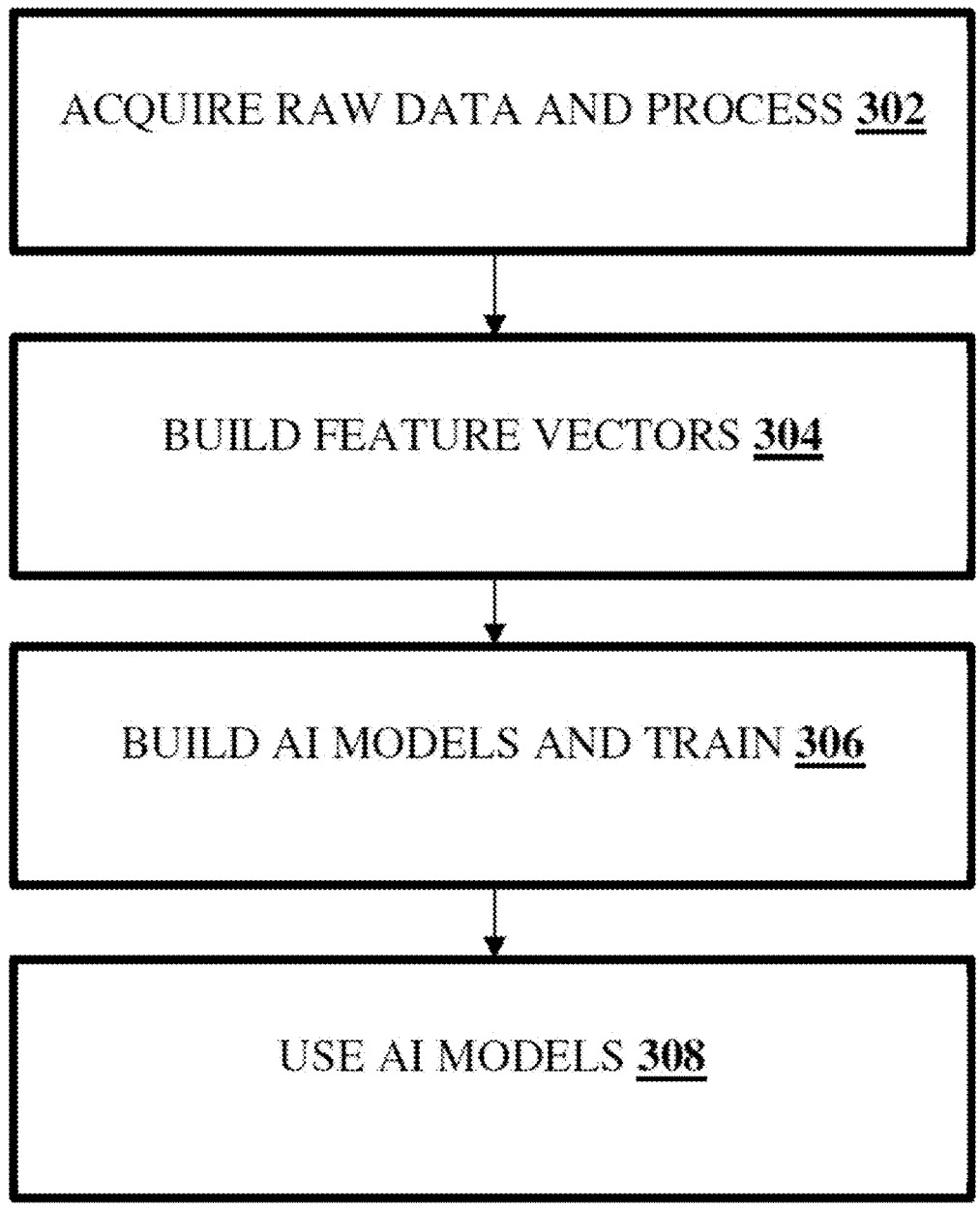
FIG. 3 shows a high-level flowchart outlining the main steps involved in developing and utilizing AI models according to an embodiment.

FIG. 3 shows a high-level flowchart outlining the main steps involved in developing and utilizing AI models according to an embodiment. The process shown broadly comprises four steps: Acquire Raw Data and Process 302, Build Feature Vectors 304, Build AI Model(s) and train 306, Use AI models 308.

Acquire Raw Data and Process 302:

The first step involves collecting the raw data necessary for analysis. This data can come from various sources and is typically unprocessed. It includes all the initial information required for the subsequent steps, such as clinical records, imaging data, sensor readings, or any other relevant data.

Dataset: A comprehensive dataset comprising various patient data along with the attributes of the left eye (OS) and right eye (OD) characteristics is collected and curated. In an embodiment, a dataset comprises a range of information such as axial length, corneal curvature, refractive error measurements, family history of myopia, age, ethnicity, and potentially other relevant ocular features including tor VA unaided, fundus, BCVA, optic disc size, cup disc ratio, optic disc, IOP, ocular alignment.

Comprehensive datasets comprising Ocular and/or Clinical data from approximately 260,000 patient records were used in the analysis and modelling for myopia presence and magnitude. 16,000 patient records having follow-up visits are used for developing models which can predict likelihood of myopia development and progression of myopia at various time periods in their future.

Processing the Data: Processing of data that is used for training the ML model is a step in the data analysis and machine learning framework, transforming raw data into a clean and usable format. This process involves several tasks, including data cleaning, normalization, transformation, and feature extraction. Data cleaning addresses missing values, duplicates, and inconsistencies within the dataset, ensuring the integrity and accuracy of the data. Normalization and scaling adjust the range and distribution of numerical features, which helps improve the performance and convergence of many machine learning algorithms. Transformation involves converting data into suitable formats, such as encoding categorical variables into numerical values or creating new features through techniques like polynomial expansion. Feature extractions, pertaining to myopia, aim to reduce the dimensionality of the data while preserving its most important characteristics, facilitating more efficient and effective model training. Preprocessing enhances the quality of the data, leading to more reliable and accurate analytical outcomes.

The primary challenges in data preprocessing include inconsistencies in data formats within key columns/features, as well as the presence of duplicate and incomplete data caused by unexpected field delimiters, symbols, and characters. Additionally, some features exhibit low variance, and the data density is particularly low for follow-up data.

To ensure data integrity, validated data columns capture only anticipated values, discarding records with mis-mapped or misrepresented assignments, such as unanticipated text values in coded fields. Identify and retain potential columns while discarding those with low variance or excessive missing values, prioritizing features with substantial information, for example, features having low information. Retain columns (features/characteristics) that have at least 50% of data, discarding those columns (features/characteristics) with more than 50% missing values. Clean, process, transform, and impute data to its lowest granularity to maximize record retention. Address inconsistent data representation and remove unanticipated or ambiguous values, for example, measured axis length has multiple representations of the same label 20/20, 6/6, 20/20p, 20/20 p, 6/6 p; 'OP' has multiple representations of same label 'dig n', 'normal','n','dig@n','ok'; 'Fundus' has multiple representations of same label 'normal','wnl','healthy'. Reduce redundancy and multicollinearity by discarding columns that can predict values of other columns, for example, Patient Category Status→'Patient Category', age→Age and Category or age at diagnosis. Identify and clean columns that aid in filtering the population for study, such as surgery types or cornea data. Specifically, validate and filter columns with potential information related to myopia, like fundus measurements for both eyes (OD & OS) and optic disc measurements. Finally, compute and transform the data to generate meaningful and interpretable labels.

Data Fusion: A multimodal approach combines ocular, medical, and environmental data to provide a holistic health assessment. In an embodiment, the process involves capturing data for the task of predicting myopia with minimal features from multiple settings, for example, Social Determinants of Health (SDOH), measured clinical values, and medical conditions.

For better data quality the following are incorporated while patient and diagnostics data is captured and stored:

Completeness Check: Verifying that all the required data fields are present for each patient or record. Identifying and handling missing data appropriately, either by imputing values or excluding incomplete records in a master database.

Consistency Check: Checking for inconsistencies in the data, such as presence of contradictory values for the same variable or illogical combinations of data points.

Accuracy Check: Validating the accuracy of the data by comparing it with known or expected values.

Outlier Detection: Identifying and examining any extreme values that deviate significantly from the anticipated range for each of the columns.

Data Integrity Check: Ensuring that the relationships between different data fields are consistent, for example, (Tests→Diagnosis→Treatment plan→Medication)

Validity Check: Checking whether data entries conform to the defined data formats and ranges. Invalid values are flagged and corrected. Maintaining and updating data dictionaries for each of the data features/columns regularly.

Data Imbalance: Checking and monitoring for imbalances in the distributions data fields of stored records.

Longitudinal Data Checks: For longitudinal studies, verify the consistency of data over time for each patient and ensure that follow-up visits and measurements align correctly.

External Validation: Validating the data against other sites/locations or from published literature to ensure that essential features/fields of the data are captured.

Build Feature Vectors 304:

Once the raw data is acquired, the next step is to transform it into a structured format that can be used by machine learning algorithms. This involves extracting relevant features from the raw data and cleaning and organizing them into feature vectors. Feature engineering is critical here, as it involves selecting the most meaningful attributes that will help the AI models learn patterns and make accurate predictions.

In an embodiment, the process involves construction of calculated features, obtaining hyperparameters of the model along with weight of risk factors after training the models.

Conventional approaches to ocular health assessment and myopia predictions have traditionally suffered from a lack of specificity and adaptability, relying on static and siloed data sets without fully accounting for the dynamic interrelations among various ocular and systemic health indicators. This limitation has often resulted in less than optimal precision in early detection, risk assessment, and management of myopia, thereby impacting patient care and outcomes.

According to an embodiment, in a dual module framework, each module is designed to process distinct sets of input data, thus addressing different aspects of ocular health and myopia management with tailored outcomes.

In an embodiment, the system utilizes advanced AI-Driven analysis for each module in the dual framework. Utilizing machine learning and deep learning techniques, the system meticulously analyzes digital eye images and patient data, extracting key ocular characteristics with enhanced precision. This approach marks a significant evolution from traditional methodologies, ensuring deep and comprehensive analysis is tailored to each module's specific data set.

Module Specific Multimodal Data Fusion: A feature of the dual module framework is its capability to synergistically integrate diverse data streams relevant to each dual module. FIG. 4 shows input features and feature engineering according to an embodiment. Module 1 comprises a targeted set of ocular metrics and patient reported data as shown as track 1 (10 features) for outcome on risk of development and risk of progression, and Module 2 comprises ocular characteristics alongside systemic and environmental health data as shown as track 2 (13 features) facilitating a nuanced understanding of myopia risk and progression tailored to the module's focus with output on detecting the presence of myopia, severity of myopia, and risk of progression.

Each module employs a specialized AI-based predictive framework designed to assess different dimensions of myopia where Module 1 analyzes for predicting likelihood of myopia in the future and its progression over a period and developing personalized management plans, and Module 2 detects the myopia (likelihood of myopia in the current time period) in the patients, severity assessment, and progression of myopia. These frameworks benefit from continuous learning to enhance prediction accuracy over time. The dual module predictive framework has distinct pathways.

In an embodiment, the system will capture during a patient's visit ocular characteristics to determine if they will develop myopia in the future or if they already have myopia. According to an embodiment, features Optic Disc Size (Small, Medium, Large), Cup Disc Ratio (numerical), Optic Disc (Normal, Abnormal), Fundus (Normal, Abnormal, Abnormal, Diabetic Retinopathy) may be obtained from diagnostic devices. In another embodiment, they may be obtained from images produced by diagnostic devices. In another embodiment, they may also be extracted from eye images from mobile or another device cameras using deep learning models. Prior to mapping/extracting the information and corresponding values, preprocessing has to be performed to enhance image quality, remove noise and normalization.

The set of Ocular characteristics captured from devices, filtered or selected by the physicians, are shown in two tracks or two sets of features.

According to an embodiment, the method and/or system is made as a part of the diagnostic device, such that the device can directly diagnose the patient and provide the results to physician to verify and further processing. In an embodiment, the system or method may be working on a computer device that is connected to the diagnostic device which can then be used to diagnose the patient and provide the results to physician to verify and further processing.

Referring to FIG. 4, Feature set 1 or track 1, comprises a set of 10 characteristics or features to detect the presence of myopia. The set of features may be captured directly from various devices.

Three features, spherical (SPH), cylindrical (Cyl), axis (Tor fr corr axis), are used as indicators for the presence of myopia. However, the main interest is in predicting likelihood of myopia using these features and also predicting when the person is having myopia or will have myopia what is the progression of myopia. In an embodiment, the three features combined with additional features are used to predict the likelihood of development of myopia, given their values if the person is already having myopia, predict what is the progression rate.

In an embodiment, combination of ocular characteristics and external factors such as screen time exposure, outdoor exposure time, etc., are used.

Referring to FIG. 4, Feature set 2 or Track 2 does not include fundamental measurements, spherical (SPH), cylindrical (Cyl), axis (Tor fr corr axis), that indicate the presence of myopia, but Track 2 uses ocular characteristics to identify if the individual has myopia or not, and the severity of myopia and its progression rate. At the outcome levels, models for a given set of ocular characteristics and other factors will determine whether the patient is having myopia or not, severity of myopia, likelihood of having myopia in the future, and the progression rate of myopia.

In track 2, ocular characteristics such as spherical (SPH), cylindrical (Cyl), axis (Tor fr corr axis), which indicate the presence of myopia are not included but other ocular characteristics such as optic disc size, disc size ratio, fundus, alignment, IOP, etc., are included. In track 2 there is no ocular characteristics which directly indicates that myopia has previously been detected. Track 1 uses Sph, cylindrical, axis, which are the features that are used to detect the presence of myopia at the time of test. Track 1 and Track 2 features are used to identify whether the patient is currently myopic or not, severity of myopia, whether the patient will be myopic in future, and what will be the progression rate.

Track 1/Group 1: Has myopia, severity of myopia, and progression of myopia.

Track 2/Group 2: does not have myopia, the likelihood of myopia, and likelihood of development and progression of myopia.

Track 2, does not use SPH, cylindrical, axis, which are usually used to detect myopia. Additional features are used to detect myopia in the current time, severity of myopia, or will the patient be myopic in near future. Features used do not just measure the current state but help assess the likelihood of myopia in the near future. The features are not just the current state, but the future state as well.

In track 2, ocular factor, not necessarily myopic related ocular characteristics, are used to detect whether the person has myopia or not, will the person become myopic in near future, and how the myopia will progress. Track 2 patients might be assessed for a scenario where the patients are not necessarily coming for eye care or myopia but track 1 is where patients are coming for an eye test which may be specific to a myopia test. However, with the AI system is present on the device or linked to the device with all the data parameters, it can identify myopic condition in patients who are coming for any kind of eye examination.

In an embodiment, the ocular characteristics may be directly read from the device used to provide the eye test and passed on to the module providing the detection and prediction of myopia.

In an embodiment, the ocular characteristics are captured in image form and the image is passed on to the modules for determining the ocular characteristics from the image.

In an embodiment, a retinoscope is used to provide the ocular measurements. A retinoscope is a diagnostic tool used by eye care professionals to objectively measure the refractive error of the eye, helping to determine the prescription for eyeglasses or contact lenses. It provides key measurements including refractive error, which encompasses myopia (nearsightedness), hyperopia (farsightedness), and astigmatism. The retinoscope examines the retinoscopy reflex, the light reflection from the retina, to determine refractive status. It measures cylinder (Cyl) for the degree of astigmatism and axis for the orientation of astigmatism correction in degrees from 0 to 180. Additionally, it assesses the spherical (Sph) measurement for correcting nearsightedness or farsightedness. The quality of the retinal reflex observed can also offer insights into the health of the retina and other eye structures, with a bright and clear reflex indicating a healthy eye, while a dull or irregular reflex may suggest other ocular conditions.

While the retinoscope provides crucial measurements and data, it does not directly provide a diagnosis. Instead, it aids eye care professionals in making a diagnosis by offering detailed information about the eye's refractive status. Retinoscopy is often performed alongside other tests to provide a comprehensive evaluation of an individual's visual needs and eye health, enabling the professional to diagnose and recommend appropriate corrective measures.

In an embodiment, the current system is integrated with a retinoscope and takes the measurements and provides the diagnosis.

Optic disc shape and cup-to-disc ratio are assessed by examining the optic nerve head, with the cup-to-disc ratio measuring the central depression (cup) within the optic nerve head (disc). These measurements are typically obtained using a fundus camera, ophthalmoscope, or optical coherence tomography (OCT), which provide detailed images of the optic nerve head. Fundus examination, which includes evaluating the retina, optic disc, macula, and posterior pole, is performed using a fundus camera, ophthalmoscope, or OCT. Intraocular pressure (IOP), the fluid pressure inside the eye, is measured with a tonometer, such as the Goldmann applanation tonometer, non-contact (air puff) tonometer, or handheld tonometer. Ocular alignment, which assesses the positioning and movement of the eyes to detect strabismus (misalignment), is evaluated using a cover test, prism and alternate cover test, or synoptophore. Best Corrected Visual Acuity (BCVA), the sharpest vision a person can achieve with corrective lenses, is measured with a Snellen chart, LogMAR chart, or phoropter. While a retinoscope is essential for measuring refractive errors of the eyes, such as myopia, hyperopia, and astigmatism, and determining the prescription for corrective lenses, it does not measure optic disc shape, cup-to-disc ratio, fundus details, IOP, ocular alignment, or BCVA. These measurements require specialized equipment and are typically performed by an ophthalmologist or optometrist during a comprehensive eye examination.

In an embodiment, the current system is integrated with the devices used for measuring various parameters and takes the measurements as input and provides the diagnosis.

In an embodiment, all the ocular parameters obtained from various equipment about a patient are collected in the cloud and accessed after prior authorization.

In an embodiment, the system considers a digital or physical image and determines the ocular data and provides it as an input for the models.

In an embodiment, the models use ocular features comprising one or more of SPH baseline, Cyl, Tor Fundus, BCV, Tor VA unaided, Distance visual acuity of the eye unaided, Trp fr corr sph, Trp fr corr cyl, Trp fr corr axis, Trp fr corr bcva.

In an embodiment, the AI model input comprises environmental features, wherein environmental features comprise one or more of pollution level exposure, sunlight exposure, bright light exposure.

In an embodiment, the AI model input comprises refraction measurements.

In an embodiment, the AI model input comprises axial length measurements.

In an embodiment, the AI model input comprises corneal curvature measurements.

In an embodiment, the AI model input comprises fundus for OD & OS.

In an embodiment, the AI model input comprises one or more optic disc measurements Oculus Dexter & Oculus Sinister (OD & OS)/Posterior Vitreous Detachment occurring in both the right eye (OD) and the left eye (OS) (PVD for OD & OS).

In an embodiment, the AI model input comprises one or more of SPH baseline, Cyl, Tor Fundus, BCV, Tor VA unaided, Distance visual acuity of the eye unaided, Trp fr corr sph, Trp fr corr cyl, Trp fr corr axis, Trp fr corr bcva.

In an embodiment, the AI model input comprises Distance visual acuity of the eye unaided.

In an embodiment, the AI model input comprises external factors, wherein external factors comprise one or more of device screen exposure, outdoor activity metrics, environmental factors, social determinants of health (age, ethnicity, gender, geography), other medical conditions (family history of myopia, present history, chief complaints).

In an embodiment, the input data is directly considering the computed values of the input data from the eye testing devices.

In an embodiment, the input data is determined from an image generated from one or more of the eye testing devices.

FIG. 5 shows multiple iterations for selection of features to be captured based on a performance metric according to an embodiment. In an embodiment, a system is developed comprising AI model/s to predict likelihood of having Myopia progression, given a set of features indicating current state of Myopia. The patient records are filtered for training and validation of the model using columns/features: "dgvst_od_retino_sph" which refers to spherical values and "1yr_od_retino_sph" in baseline and follow-up year, which refers to spherical value at one year follow up appointment. Approximately 16,000 patient records were identified having an auxiliary target ("1yr_od_retino_sph") and an Auxiliary Target column/auxiliary feature. The records were cleaned to make the values appropriate for the analysis.

FIG. 6 shows a selected list of features for building an AI model for predicting the progression of myopia according to an embodiment. Records are filtered with criteria of minimum missing values for each of the 13 columns as shown in FIG. 6. Outliers are removed to improve performance of the model's predictability.

FIG. 7 shows a target variable and its derivation for building an AI model for predicting the progression of myopia according to an embodiment. Target column/variable was prepared by categorizing the difference of "dgvst_od_retino_sph" and "1yr_od_retino_sph" which represent spherical value and spherical value at one year follow up appointment.

Calculate the difference in SPH (Spherical) values between the first and follow-up visits which is named as "sph_difference". Summary of first visit sph is named as "dgvst_od_retino_sph". Summary of follow-up visits sph is named as "1yr_od_retino_sph". Summary of difference in the "SPH" values in visits and "1yr_od_retino_sph" is shown in FIG. 7 under "sph_difference".

FIG. 8 shows the stratification of progression using the target variable according to an embodiment. Leveraging the difference in SPH (Spherical) values between the first and follow-up visits to stratify progression. Stratification Targets labeled Yes (labeled as 1) for corresponding values of less than or equal to −0.5 and No (labeled as 0) for other cases. FIG. 8 shows the count of target labels.

FIG. 9 shows training and evaluation of Myopia Progression Models according to an embodiment. The data in the table of FIG. 9 presents a comparative analysis of various AI algorithms used for a classification task, evaluating performance metrics such as accuracy (for training, validation, and test sets), confusion matrix details, precision, and recall. The algorithms evaluated include Linear Support Vector Classifier (SVC), Gaussian Naive Bayes (NB), K-neighbors Classifier, Logistic Regression, Decision Tree Classifier, Stochastic Gradient Descent (SGD) Classifier, Bagging Classifier, Extra Trees Classifier, Random Forest Classifier, and XGB (XGBoost). Accuracy metrics demonstrate the proportion of correctly classified instances across training, validation, and test sets. The confusion matrix for the test set details true negatives (TN), false positives (FP), false negatives (FN), and true positives (TP). Precision measures the ratio of correctly predicted positive observations to the total predicted positives, while recall measures the ratio of correctly predicted positive observations to all observations in the actual class. Both metrics are provided for labels "Yes" and "No."

Key observations include the Bagging Classifier and Extra Trees Classifier achieving the highest test accuracy at 0.98. Most models demonstrate high precision and recall, indicating a good balance in correctly identifying both positive and negative instances. The Extra Trees Classifier and Random Forest Classifier particularly stand out with high precision and recall values. Logistic Regression also shows strong performance with a balance of accuracy (0.92) and relatively high precision and recall for both labels. In contrast, the SGD Classifier has the lowest recall for Label "Yes" (0.08), indicating poor performance in identifying positive instances. The table provides insights into the effectiveness of different AI algorithms for classifying the dataset, helping to identify the most suitable model/s for deployment based on comprehensive accuracy, precision, and recall metrics.

In an embodiment, more than one model may be considered with appropriate weights on each model's output as well as individual outputs and a result arrived from a weighted average of these models.

Genetic Algorithms (GAs) are a class of optimization techniques inspired by the principles of natural selection and genetics, and they can be effectively used in the selection and optimization of AI models for myopia prediction. The process begins with the initialization of a population of candidate models, each represented by a set of parameters and hyperparameters encoded as chromosomes. These initial models can be various types of algorithms, such as Logistic Regression, Support Vector Machines (SVM), K-Nearest Neighbors (KNN), Decision Trees, and ensemble methods like Random Forest and Gradient Boosting.

The genetic algorithm then iteratively evolves this population to improve model performance. Each iteration, or generation, involves several steps. First, models are evaluated based on a fitness function, which typically measures performance metrics such as accuracy, precision, recall, or Area Under the Receiver Operating Characteristic Curve (AUC-ROC) on a validation dataset. The best-performing models are selected to contribute to the next generation. Next, pairs of selected models are combined to create offspring models by exchanging segments of their chromosomes in a process known as crossover. This simulates the biological crossover process and allows new models to inherit features from multiple parent models, potentially leading to better performance. Then, random changes are introduced to the offspring models' chromosomes through mutation, maintaining genetic diversity within the population and exploring new regions of the solution space to prevent premature convergence to suboptimal solutions. Finally, the new generation of models replaces the old ones, and the process repeats until a predefined stopping criterion is met, such as a maximum number of generations or a satisfactory level of performance. FIG. 10 shows the stratification of progression using the target variable according to an embodiment. Leveraging the difference in SPH values of the first and follow-up visits to identify Patients with Myopia in follow-up visit and not in first visit to stratify progression. Stratification Targets labels Yes (labeled as 1) for corresponding values indicating developed myopia in the follow-up year but not in first visit and No (labeled as 0) for other cases. FIG. 10 shows the count of target labels.

FIG. 11 shows training and evaluation of Myopia Progression Models according to an embodiment. The table provides performance comparison of various AI algorithms based on their accuracy in training, validation, and test datasets, alongside their confusion matrix details, precision, and recall metrics. The Linear SVC algorithm shows consistent accuracy across datasets at 0.67, with moderate precision and recall values indicating a balanced but not exceptional performance. Gaussian NB, with accuracy around 0.76-0.78, demonstrates a high recall for negative instances but a significantly lower recall for positive ones, indicating a bias towards correctly classifying negative cases. The K-neighbors classifier performs well with a high test accuracy of 0.85 and excellent precision and recall for negative cases, though it is less reliable for positive cases.

Logistic Regression maintains a balanced accuracy of 0.85 and shows good precision and recall for both positive and negative instances, making it a reliable model overall. The Decision Tree Classifier, with a high test accuracy of 0.96, demonstrates strong predictive power with high precision and recall values for both labels. The SGD Classifier, however, shows moderate accuracy and extremely low recall for positive instances, indicating poor performance in identifying positive cases.

Bagging Classifier and Extra Trees Classifier both exhibit high performance, with test accuracies of 0.96 and 0.98 respectively. They show high precision and recall values for both labels, indicating robustness and reliability. The Random Forest Classifier also performs well with balanced accuracy and high precision and recall for negative instances, though it is less reliable for positive cases. Lastly, the SVC algorithm shows good overall performance with an accuracy of 0.87, balanced precision, and recall values particularly excelling in identifying negative instances.

In summary, the Extra Trees Classifier and Bagging Classifier stand out as the most effective models, showcasing high accuracy and balanced precision and recall values across both positive and negative labels, while other models like Logistic Regression and Decision Tree Classifier also demonstrate strong and reliable performance.

FIG. 12 shows a high-level data summary used for Myopia Informed Artificial Intelligence System development according to an embodiment.

The table provides a comparison between a baseline dataset and a curated dataset after cleansing and imputation processes. Both datasets initially contain 328,077 records and 120 columns from 35 centers. After excluding 38 columns with more than 50% missing values, each dataset is reduced to 82 columns while maintaining the same number of records. The cleansing of missing values in the Retino Sphere columns further refines the datasets to 326,984 records and 82 columns. However, a discrepancy occurs in the cleansing of missing values in the Retino Cylinder columns, resulting in 88,775 records and 84 columns in the baseline dataset, but the curated dataset retains 326,984 records and increases from 82 to 84 columns.

Age distribution analysis shows differences between the datasets. In the baseline dataset, the number of records decreases with increasing age, ranging from 9,220 records for ages 0-10 to 1,661 records for ages 51-60. In contrast, the curated dataset shows a higher number of records across all age groups, from 26,880 for ages 0-10 to 5,651 for ages 51-60, indicating extensive data augmentation or recovery during the data cleansing process.

Further steps include the exclusion of records for individuals over 40 years old, which reduces the baseline dataset to 79,850 records and the curated dataset to 294,418 records, both still with 84 columns. Exclusion of high-correlation and redundant columns then reduces both datasets to 73 columns, maintaining the same number of records.

Finally, cleansing the Cornea labels results in 77,444 records in the baseline dataset and 280,166 records in the curated dataset, each with 73 columns. The significant differences in record counts between the baseline and curated datasets highlight the thorough data cleansing and augmentation processes applied to the curated dataset to improve its quality and comprehensiveness for analysis.

FIG. 13 shows a longitudinal data summary for Myopia Informed Artificial Intelligence System according to an embodiment. The table presents a longitudinal dataset tracking records over six years, starting from a baseline year. The initial baseline dataset comprises 328,077 total records, with 280,166 of these records curated for the first year. In the first year, the dataset begins with 40,185 records, of which 39,639 are carried over from the previous year (curated), and an additional 6,039 records are newly introduced.

In the second year, 17,169 records were carried over from the first year, with 11,130 continuing from the previous year and 1,991 being new entries. The third year shows 11,174 records carried over, with 9,183 from the previous year and 811 new records added. For the fourth year, 8,828 records are recorded, of which 8,017 continue from the previous year and 310 are new additions.

In the fifth year, 5,822 records persist, with 5,512 from the previous year and 131 new records. The dataset concludes in the sixth year with 3,517 records, 3,386 of which are carried over from the previous year.

There is a gradual decline in the number of total records each year, indicating either dropouts, patients no longer meeting the criteria, or reduced follow-ups. The majority of records each year are carried over from the previous year, showing continuity in patient follow-up. New entries are introduced each year, though in decreasing numbers as the years progress.

This longitudinal data and its tracking provides insights into patient retention, follow-up rates, and the introduction of new patient records over a six-year period. The curated dataset for the first year forms the foundation for subsequent years, ensuring a consistent and quality data framework for longitudinal analysis.

FIG. 14 shows features that are least important in the myopia prediction according to an embodiment. The data was fitted for ten Machine Learning (ML) models to assess the predictability and comparative analysis performed to identify the best fitting model to predict the progression of myopia.

The following are the Challenges that have been addressed with the dataset:

Columns are validated to ensure only anticipated values are captured, discarding incorrectly mapped/represented records.

Identified and retained potential columns and discarded columns with low information (low variance/missing values).

Retained columns having at least 50% of data, selectively discarding columns with >50% missing values.

Data cleansing/processing/transforming/imputing the columns to lowest granularity to retain maximum records (handling inconsistent representation of data).

Reduced redundancy and multicollinearity in data, discarding columns that cannot be used to predict other column values.

Identified, cleansed, explored columns that aid in filtering the population for study.

Identified, validated and filtered columns having potential information with respect to Myopia.

Compute, transform the data and generate interpretable encoded values/labels from data ready for modelling.
Challenges
Data formats are inconsistent within key columns; Duplicate and/or incomplete data due to unexpected field delimiters, symbols and characters; Data has low variance for some features; Data density is low for follow-up data.

Final counts are reduced to Rows (patient records): ~275,000 rows and Columns (features): ~80 columns.
Build AI Model(s) and Train 306:

In this step, the feature vectors are used to train AI models. Various machine learning techniques and algorithms are applied to build models that can analyze the data and identify patterns, make predictions, or classify information. This step involves selecting the appropriate algorithms, training the models on the data, and validating their performance to ensure they provide accurate and reliable results.

Myopia-Informed AI system for Eye care or Myopia-informed AI models identify the patients at risk in an early stage. Machine learning-based AI models were developed to identify and capture patterns in patient data and their refractive errors for both the left (OS) and right (OD) eyes. These AI models utilized a comprehensive set of inputs, including patients' ocular, medical, socioeconomic characteristics, and latent factors such as electronic device screen time management and time spent outdoors. The outputs of these models include scores for the likelihood of developing myopia, the magnitude of myopia, the likelihood of myopia progression, and the likelihood of myopia development. The machine learning techniques employed to identify these patterns include logistic regression, support vector machines (SVM), K-nearest neighbor, decision trees, and ensemble methods.

To achieve these outputs, various machine learning techniques were employed:

Logistic Regression: This model is ideal for binary classification problems, making it suitable for predicting the likelihood of developing myopia. By analyzing the relationship between multiple independent variables (e.g., ocular data, clinical data, screen time, outdoor activity, etc.) and the binary outcome (developing myopia or not), logistic regression can estimate the probability of myopia onset.

Support Vector Machines (SVM): SVMs are effective in high-dimensional spaces and are used for both classification and regression tasks. For myopia prediction, SVMs help classify patients into different risk categories based on their ocular and lifestyle data. By finding the optimal hyperplane that separates the data into different classes, SVMs can accurately predict the likelihood of myopia development and progression.

K-Nearest Neighbor (KNN): This algorithm classifies data points based on the closest training examples in the feature space. For myopia prediction, KNN classifies patients by comparing their data to the most similar historical cases. This method is particularly useful for identifying patterns in patients with similar characteristics and predicting their risk of myopia.

Decision Trees: Decision trees model decisions and their possible consequences, creating a tree-like structure of decisions. For myopia, decision trees map out potential outcomes based on various patient characteristics. Each node in the tree represents a feature (e.g., screen time, outdoor activity), each branch represents a decision rule, and each leaf represents an outcome (e.g., likelihood of myopia progression).

Ensemble Methods: Ensemble methods combine the predictions of multiple models to improve accuracy and robustness. Examples include Random Forests and Gradient Boosting Machines (GBM). By aggregating the predictions of several decision trees (as in Random Forests) or sequentially improving the model (as in GBM), ensemble methods enhance predictive performance and reduce the risk of overfitting. For myopia prediction, ensemble methods provide a more comprehensive assessment by leveraging the strengths of different models. In an embodiment, each method can provide various outputs and each method, and each output of the method, can be weighted before the results are ensembled into one single prediction result for each detection of myopia, prediction of myopia, and progress of myopia.

In an embodiment, various ensemble methods used include bagging, boosting, stacking, voting, and blending. Bagging, exemplified by Random Forest, involves training multiple instances of the same model on different subsets of the training data and combining their predictions. Boosting, used in algorithms like AdaBoost and XGBoost, sequentially builds models that correct the errors of their predecessors, with final predictions being a weighted combination of all models. Stacking performs training multiple base models, using their predictions as inputs to a higher-level meta-model for the final prediction. Voting combines predictions from multiple models by majority vote or averaging. Blending, similar to stacking but simpler, uses a holdout validation set for training the meta-model. These ensemble methods are powerful tools for reducing overfitting and variance, leading to better generalization on unseen data and improve predictive performance in both competitions and real-world applications. These models are integrated, and the AI system can provide assessments, enabling eye care professionals to implement targeted and personalized intervention strategies for myopia management.

In an embodiment, AI models are constructed by training the models with the data and are configured to take the data from a patient record and predict the likelihood of myopia, magnitude of myopia, and progression of myopia with scores and risk stratification.

In an embodiment, an outcome of the AI model provides insights on contributing risk factors for better management of condition across different cohorts along with risk level.

In an embodiment, it is an AI based approach for detecting and monitoring the progression of myopia in an individual, comprising the steps of: capturing ocular data from the individual, including but not limited to, refraction measurements, axial length measurements, and corneal curvature measurements; generating a myopia detection score based on the ocular data, wherein the myopia detection score is indicative of the presence and severity of myopia; and collecting additional data related to the individual, including but not limited to, age, gender, genetic information, and social economic factors.

Training AI/ML models: In an embodiment, a first machine learning model is trained using the ocular data and supplementary data to predict the likelihood of myopia; a second machine learning model is trained using the ocular data and supplementary data to predict the severity of myopia; and a third machine learning model is trained using the ocular data and supplementary data to predict the progression of myopia.

An AI based system/device that can predict the likelihood of having myopia, given minimal data characteristics of the patient, thereby enabling efficient clinical decision making in the screening for myopia, wherein the minimal data characteristics include ocular data as SPH (Spherical), CYL (cylindrical) and axis data An AI based system/device that can predict the magnitude of myopia, given minimal data characteristics of the patient, thereby enabling efficient clinical decision making in the diagnosis and treatment of myopia.

An AI based system/device that can predict the progression of myopia, given the potential risk factors of the patient, thereby enabling efficient clinical decision making in diagnosis and interventions to prevent further deterioration of vision. Potential risk factors include stratified ocular characteristics and risk predictions based on the stratified ocular characteristics.

In an embodiment, the system further provides comprehensive insights of a patient's key health indicators with respect to a diagnosis/treatment, wherein comprehensive insights comprise prediction of development of myopia, detection of myopia, severity of myopia, and/or progression of myopia. Further, the models provide a mapping of output to the inputs which explain the factors contributing to the risks.

In an embodiment, the system predicts Myopia using left eye characteristics and right eye characteristics using machine learning models. Nearsightedness, clinically known as myopia, is a common vision disorder that affects a significant portion of the global population. Accurate predictions of myopia development can assist healthcare professionals in early interventions and personalized treatment strategies. In an embodiment, machine learning models are developed and trained such that they are capable of predicting the likelihood of a user developing myopia based on the characteristics of their OS (Oculus Sinister), which refers to the left eye and OD (Oculus Dexter) which refers to the right eye and/or OU (Oculus Uterque) which refers to both eyes.

AI/ML Model Generation:

In an embodiment the system and/or the method comprises a dual module framework, to address various facets of ocular health and myopia management. Each module harnesses the power of advanced AI, employing machine learning techniques to conduct detailed analyses of ocular characteristics and patient data (clinical and medical). This system pinpoints key ocular features with greater accuracy, representing a significant leap beyond traditional analysis techniques and providing a deep, module-specific examination.

Patient data was extracted and anonymized from a database, which is used for building the AI models, analyzing approximately 300,000 patient records. This patient data comprises ocular characteristics, patient demographics, medical histories, and clinical outcomes. The data was cleaned and transformed, including standardization, normalization, and encoding for better representation. Potential columns (each representing a feature) were filtered for modeling by dropping those with high missing values, low variance, and multicollinearity.

Predictive framework with specialized pathways: In an embodiment, the system or method features two specialized AI-based predictive frameworks, each designed to explore different dimensions of myopia. These frameworks leverage the cleaned and processed patient data to provide precise and actionable insights into myopia management and treatment strategies.

Myopia-Informed AI System for Eye Care: A Dual Module Framework

Module 1 is focused on forecasting myopia progression and tailoring personalized management plans. These frameworks are designed for continuous learning, steadily improving their prediction accuracy over time (input data stream needs 10 features).

Module 2 is focused on evaluating presence and severity, providing a foundation for understanding an individual's myopia status (input data stream has 12 features).

This dual module approach not only enhances the precision of ocular health assessments but also paves the way for personalized and effective myopia management strategies.

Module 1 Trained with Data Stream I to Develop Model I

Conventional approaches to ocular health assessment and myopia prediction have traditionally suffered from a lack of specificity and adaptability, relying on static and siloed data sets without fully accounting for the dynamic interrelations among various ocular and systemic health indicators. This limitation has often resulted in less than optimal precision in early detection, risk assessment, and management of myopia, thereby impacting patient care and outcomes.

Model I for Myopia Monitoring for Development and Progression

Myopia-informed AI models are designed to identify patients at risk of developing myopia and those with existing myopia who are at risk of its progression. The outputs from these models include scores for the likelihood of myopia progression and the likelihood of myopia development. To identify patterns and generate these scores, machine learning models employed include logistic regression, SVM, K-nearest neighbor, decision trees, and various ensemble methods (including random forest, extra trees, and bagging).

FIG. 15 shows Data stream I used for training Model I according to an embodiment. The table illustrates Data Stream I which includes 10 features used to predict outcomes related to myopia. The features encompass gender, age, chief complaints, present history, tor VA unaided, fundus, BCVA, SPH (baseline), cyl (baseline), and tor fr corr axis. These variables are utilized to forecast two primary outcomes: the risk of progression towards myopia and the risk of developing myopia. This approach helps in identifying patients who are at risk of myopia and enables early intervention to manage or prevent the condition.

Figure 16:
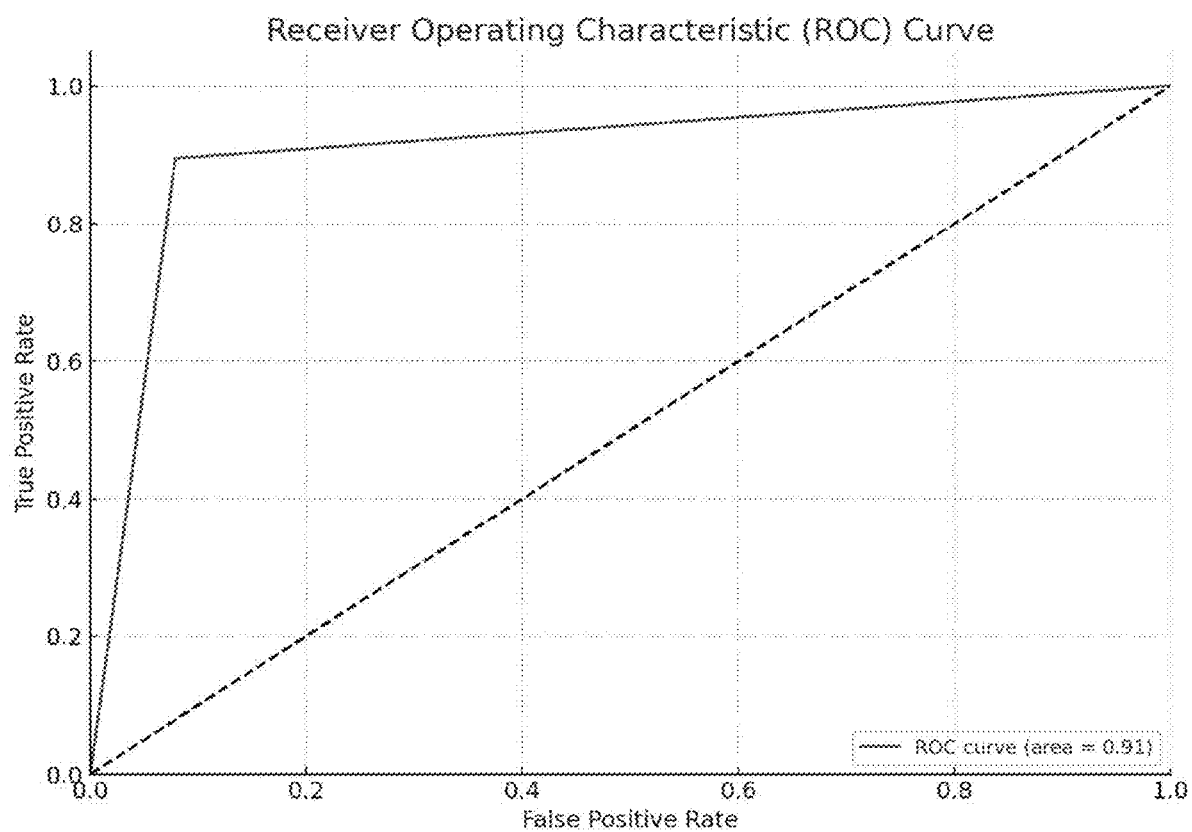
FIG. 16 shows Receiver Operating Characteristic (ROC) curve for Model I, Sub Model I according to an embodiment.

FIG. 16 shows Receiver Operating Characteristic (ROC) curve for Model I, Sub Model I according to an embodiment. The figure illustrates a Receiver Operating Characteristic (ROC) curve, a graphical representation used to evaluate the performance of a binary classification model. The curve is plotted with the True Positive Rate (TPR) on the vertical axis and the False Positive Rate (FPR) on the horizontal axis, highlighting the trade-offs between sensitivity and specificity across various threshold levels. The solid line, which represents the ROC curve for the model, starts from the origin (0,0), ascends sharply to a high TPR at a low FPR, and then gradually approaches the top-right corner (1,1). This trajectory indicates that the model is effective at distinguishing between the positive and negative classes, maintaining a high true positive rate with minimal false positives.

The dashed black line denotes the line of no-discrimination, where the performance would be equivalent to random guessing, with the TPR equaling the FPR at all points. The fact that the ROC curve stays well above this line demonstrates the model's superior discriminative ability. The area under the ROC curve (AUC) is 0.91, a metric that quantifies the overall performance of the model. An AUC of 1.0 would indicate perfect classification, while 0.5 would reflect a lack of discrimination. With an AUC of 0.91, the model exhibits excellent predictive accuracy, effectively distinguishing between the two classes across various thresholds. This figure succinctly captures the model's performance, showing it to be highly effective in classifying the instances correctly.

The Receiver Operating Characteristic (ROC) Curve and the Area Under the Curve (AUC) Score further assess the model's performance. ROC Curve illustrates the trade-off between the true positive rate (sensitivity) and the false positive rate (1—specificity) at various threshold settings. The curve closer to the top-left corner indicates a better performance. AUC Score, approximately 0.91, suggesting that the model has a high ability to distinguish between progression and non-progression cases. An AUC score of 1 indicates perfect prediction, while a score of 0.5 suggests no discriminative power (equivalent to random guessing). The ROC curve and AUC Score confirm that the updated model has strong discriminative power, capable of effectively separating the instances likely to develop near-sightedness from those that are not.

The model performance analysis involves ground truth determination with 11,199 entries in both the "Predict_Progression" and "Ground_truth" datasets. On average, about 25.4% of the entries are predicted to progress. Both the predictions and actual values have a similar spread, with standard deviations of 0.435 and 0.411, respectively. The distribution shows that "Predict_Progression" includes 8,353 non-progression (0) and 2,846 progression (1) predictions, while the "Ground_truth" dataset shows 8,793 non-progression (0) and 2,406 progression (1) actual instances.

The analysis of the model's performance highlights several key aspects regarding its ability to predict myopia progression. The dataset consists of 11,199 entries, where both predictions (Predict Progression) and ground truth have a similar spread with standard deviations of 0.435 and 0.411, respectively, with about 25.4% of the entries predicted to progress. In terms of distribution, the model predicts 8,353 instances of non-progression and 2,846 instances of progression, while the actual data shows 8,793 non-progression and 2,406 progression cases. The model has been clinically validated against patient records with one-year follow-up visits, demonstrating promising results in early detection of myopia. Furthermore, there is a high correlation (approximately 0.77) between the model's predictions and the actual outcomes, indicating that the predictions closely match the ground truth of myopia progression. This strong alignment suggests the model's effectiveness in identifying progression in myopia.

Clinical validation of the model 1: myopia informed AI models' effectiveness is validated against patients' records having 1-year follow up visits with ophthalmologists' assessment regarding myopia; and models have shown promising performance in early detection of myopia.

High Correlation Between Outcomes: There is a strong correlation (approximately 0.77) between Predict Progression and Ground truth, indicating that the predictions align closely with the actual progression status.

Figure 17:
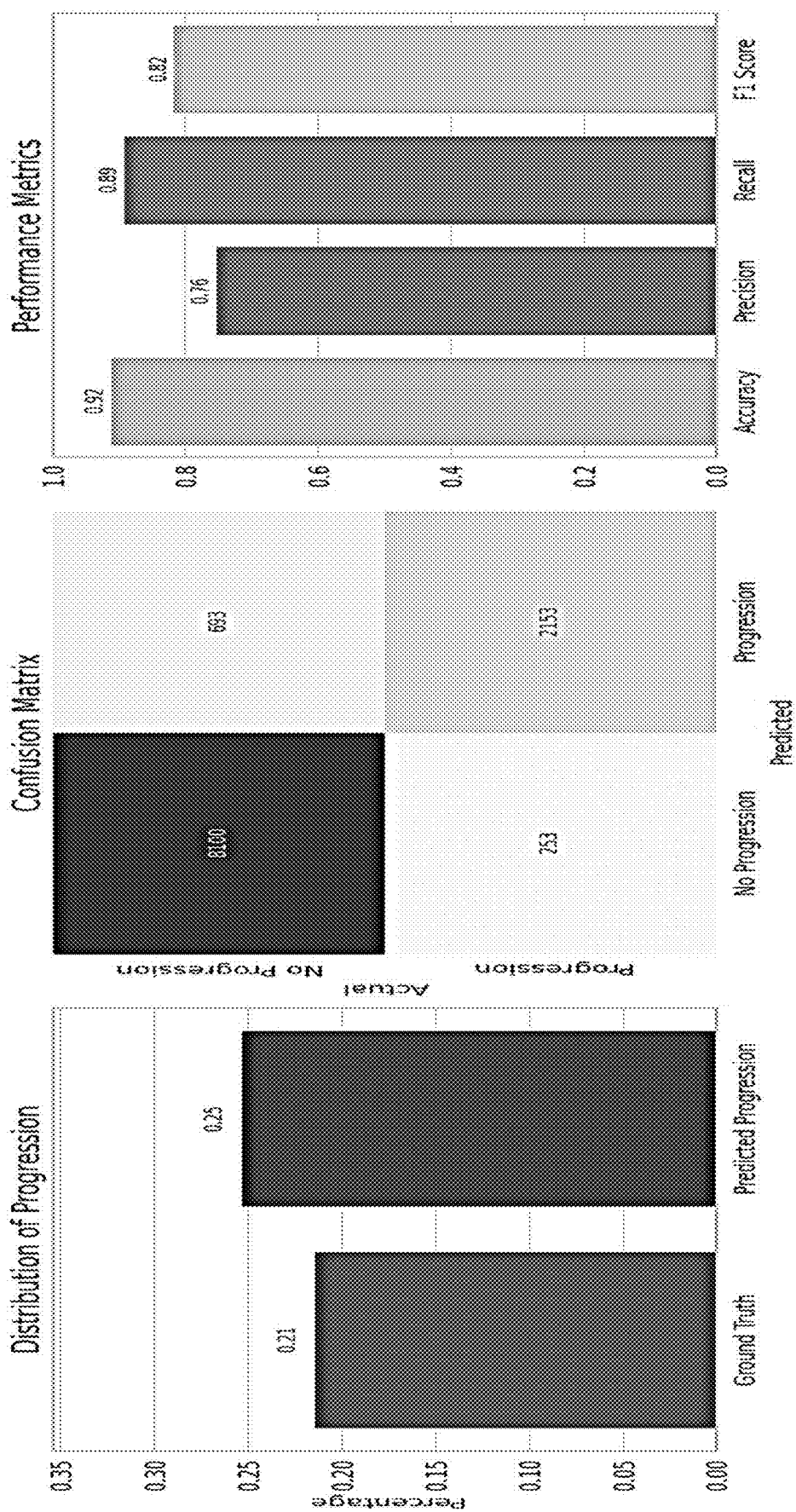
FIG. 17 shows Model I, Sub Model I performance analysis according to an embodiment.

FIG. 17 shows Model I, Sub Model I performance analysis according to an embodiment. FIG. 17 shows three bar charts, Distribution of Progression, Confusion Matrix, and Performance Metrics which are discussed below. Distribution of Progression: This bar chart illustrates the percentage of observed progression (Ground Truth) versus predicted progression. It shows that the predicted progression is slightly higher than the observed progression, reflecting the data's distribution. The first bar chart compares the proportion of progression instances in the ground truth data versus the predicted data. In the ground truth, approximately 21% of the entries are classified as ground truth, while in the predictions, about 25% are classified as progression.

Confusion Matrix: The heatmap visualizes the confusion matrix, detailing the true positives, true negatives, false positives, and false negatives. This gives a clear view of how predictions align with the actual progression cases, highlighting the model's performance in distinguishing between progression and no progression. The confusion matrix provides a visual representation of the model's performance in terms of true positives, true negatives, false positives, and false negatives. It shows that the model correctly identified 8,100 instances as non-progression and 2,153 instances as progression. However, there were 693 instances where the model predicted progression incorrectly (false positives) and 253 instances where progression was missed (false negatives).

Performance Metrics: This bar chart compares the accuracy, precision, recall, and F1 score. High accuracy and recall are noticeable, indicating a strong performance in correctly identifying progression where it exists. The precision and F1 score are also high, showing a balanced performance between the precision and recall. The performance metrics bar chart summarizes the accuracy, precision, recall, and F1 score of the model. The model achieved an accuracy of 0.92, a precision of 0.76, a recall of 0.89, and an F1 score of 0.82. These metrics provide a comprehensive view of the model's ability to correctly identify progression and non-progression instances.

The effectiveness and reliability of the model I in predicting the progression of the myopia condition shows a high level of accuracy and balanced performance metrics.

Figure 18:
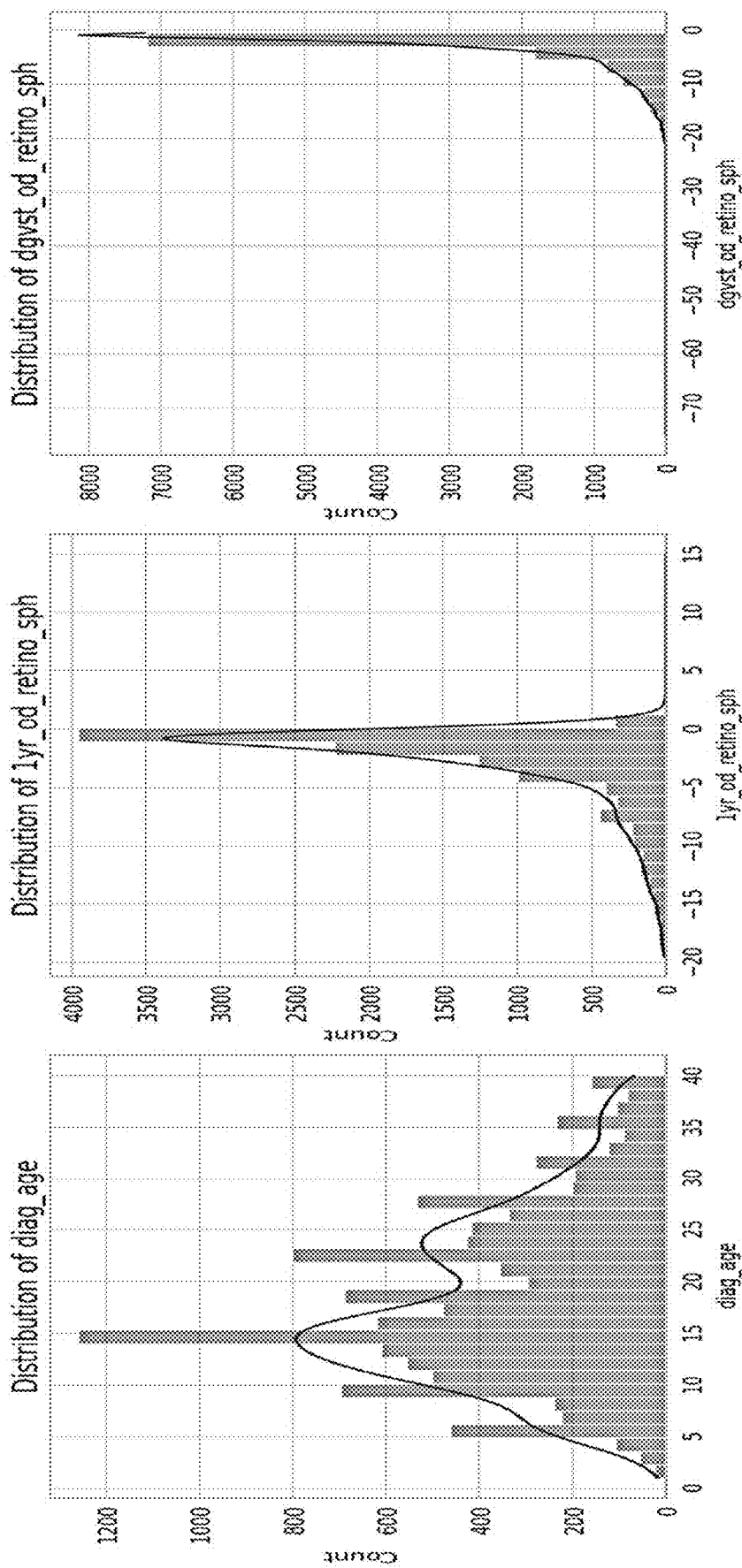
FIG. 18 shows data analysis for Model I, Sub Model I according to an embodiment.

FIG. 18 shows data analysis for Model I, Sub Model I according to an embodiment.

The figure presents three histograms each overlaid with Kernel Density Estimate (KDE) curves, illustrating the distributions of different ophthalmic variables. The first plot shows the distribution of diag_age, which likely represents the age at diagnosis. It reveals that most diagnoses occur around age 15, with a broad range from 5 to 35 years and fewer cases below age 5 and above 35. The second plot depicts the distribution of 1yr_od_retino_sph, potentially indicating the spherical equivalent in diopters of the right eye one year post-event. This distribution is skewed left, suggesting a predominance of myopia (nearsightedness), with most values clustering between −5 and 0 diopters. The third plot illustrates the distribution of dgvst_od_retino_sph, which likely represents changes in the spherical equivalent over time. This distribution is even more skewed to the left, showing a significant number of very negative values and indicating substantial progression or correction in the spherical equivalent. These visualizations together highlight common diagnostic ages and typical ranges of spherical equivalent values and changes in the dataset.

The histogram of Age shows a skew towards younger ages, with a peak in the early teens. This reflects the mean age (approximately 18.58 years) and indicates a concentration of younger individuals in the dataset.

Distribution of 1yr_od_retino_sph and dgvst_od_retino_sph: Both histograms show a distribution leaning towards negative values, indicating a prevalence of myopia (near-sightedness) in the dataset. The spread and skewness of these distributions are consistent with the descriptive statistics, highlighting the variability in the severity of myopia among patients.

Age-related Variability: There is noticeable variability in the average spherical values at different ages. Some age groups, particularly in the early to mid-teens, show more negative average spherical values, suggesting more severe myopia.

Figure 19:
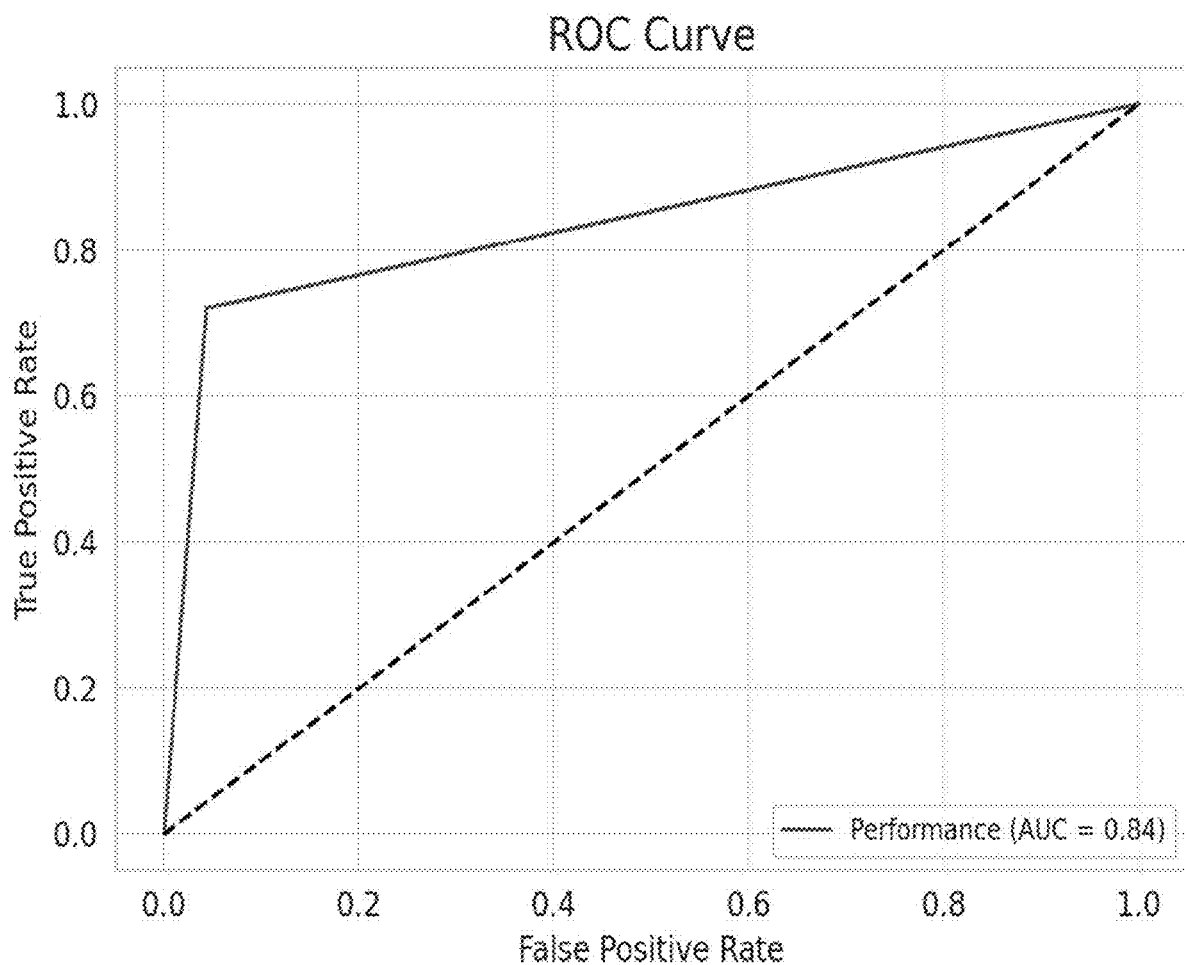
FIG. 19 shows Receiver Operating Characteristic (ROC) curve for Model I, Sub Model II performance analysis according to an embodiment.

FIG. 19 shows Model I, Sub Model II performance analysis according to an embodiment. The figure presents a Receiver Operating Characteristic (ROC) curve, which assesses the performance of a binary classification model. The curve plots the True Positive Rate (TPR) against the False Positive Rate (FPR) at various threshold settings. The solid line represents the ROC curve for the model, which illustrates the trade-off between the TPR and FPR as the decision threshold changes. The curve begins at the origin (0,0) and moves towards the top-right corner (1,1), indicating how well the model distinguishes between the positive and negative classes. The dashed black line represents the line of no-discrimination, which corresponds to the performance of a random classifier, where the TPR equals the FPR across all thresholds. The model's curve lying above this diagonal indicates its superior performance compared to random guessing.

The Area Under the Curve (AUC) is 0.84, a metric summarizing the model's overall ability to classify instances correctly. An AUC of 1.0 denotes perfect classification, while an AUC of 0.5 indicates no discriminative power. The AUC of 0.84 suggests that the model is quite effective at distinguishing between the two classes, achieving a high TPR while maintaining a relatively low FPR. This ROC curve, with its AUC value, provides a clear and concise visualization of the model's discriminative performance, allowing for easy comparison with other models or thresholds.

The Receiver Operating Characteristic (ROC) Curve for the model, along with the Area Under the Curve (AUC) score, provides a comprehensive assessment of the model's performance in predicting the development of near-sightedness. The AUC score is approximately 0.838, which quantifies the overall ability of the model to discriminate between the positive class (development of near-sightedness) and the negative class (no development). An AUC score closer to 1 indicates excellent model performance, whereas a score closer to 0.5 suggests a performance no better than random guessing. AUC of 0.84 indicates that the model has a strong predictive power, successfully distinguishing between the two classes.

These insights demonstrate that the model performs well in predicting progression, with high accuracy, precision, recall, and an excellent AUC score.

The analysis of the model's performance focuses on predicting the development of near-sightedness (myopia), specifically based on a spherical (SPH) value in the follow-up year being less than or equal to −0.50. The dataset includes 4,994 entries where both predicted and actual development statuses are recorded (Predict Progression and Ground truth). On average, 23.3% of these entries are predicted to develop near-sightedness. The spread of values for predictions and actual outcomes is similar, with standard deviations of 0.423 for the predictions and 0.444 for the actual ground truth. In terms of distribution, the model predicts no development (0) in 3,828 instances and development (1) in 1,166 instances. Conversely, the actual data indicates 3,641 cases of no development (0) and 1,353 cases where near-sightedness does develop (1). This comparison shows that while the model predicts near-sightedness development accurately, it tends to predict slightly fewer development cases than what is observed in reality.

Correlation Between Outcomes: The correlation coefficient is approximately 0.718. This value indicates a strong positive correlation, suggesting that as the predictions for the development of near-sightedness increase (moving towards predicting development), the actual instances of near-sightedness developed (as captured by "Ground truth") increase.

Figure 20:
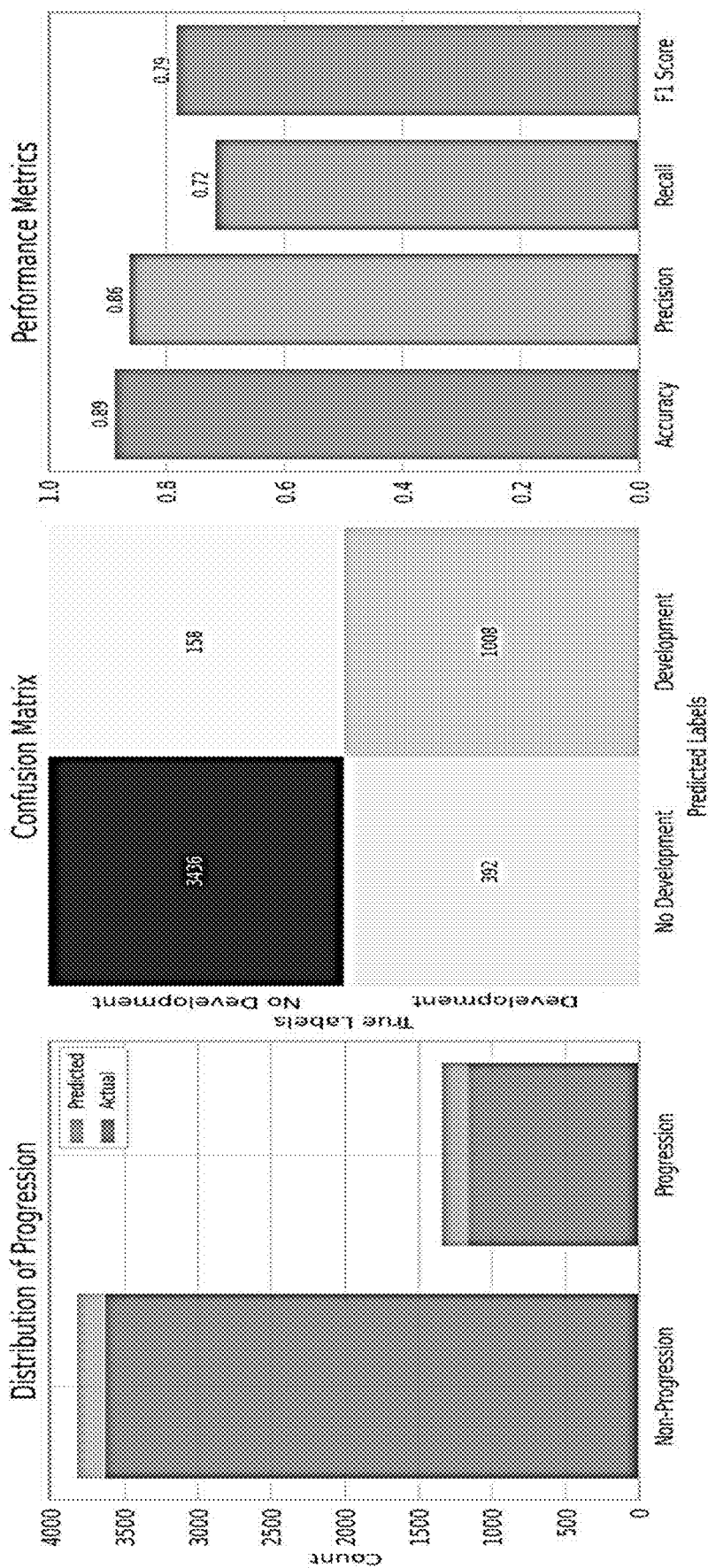
FIG. 20 shows Model I, Sub Model II performance analysis according to an embodiment.

FIG. 20 shows Model I, Sub Model II performance analysis according to an embodiment.

Distribution of Progression: The bar chart illustrates the distribution of predicted versus actual instances of progression (development of near-sightedness). It shows a close alignment between the predicted and actual counts, indicating the model's effectiveness in capturing the general trend of progression within the dataset.

Confusion Matrix: The heatmap of the confusion matrix provides a detailed view of the model's performance, highlighting the true positives (correctly predicted progression) and true negatives (correctly predicted non-progression).

Performance Metrics: The bar chart displaying accuracy, precision, recall, and F1 score offers a concise summary of the model's performance. High accuracy suggests that the model correctly predicts a large proportion of outcomes. Precision and recall values indicate the model's ability to identify true cases of progression with minimal false positives and its effectiveness in capturing most actual progression cases, respectively. The F1 score, a balance between precision and recall, further confirms the model's robust performance.

Figure 21:
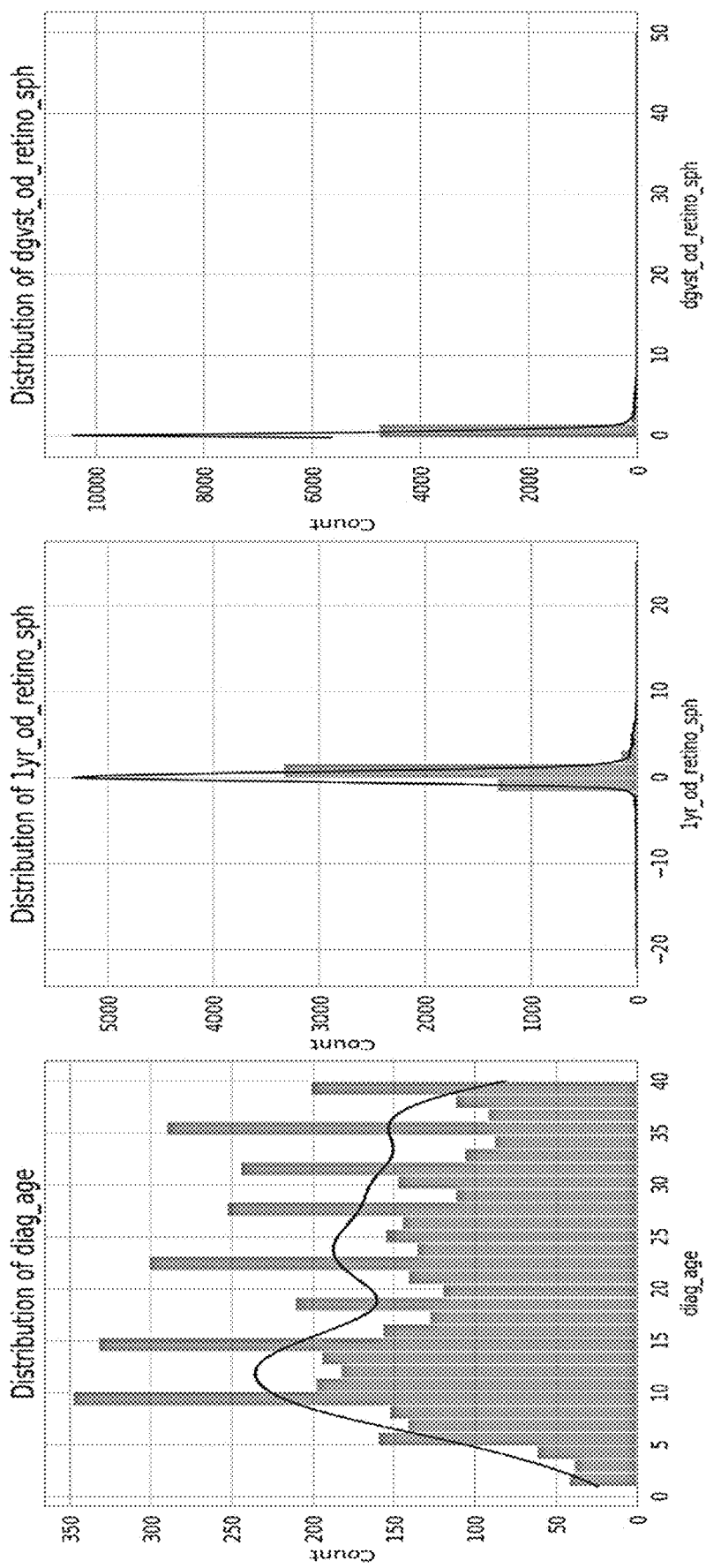
FIG. 21 shows data analysis for Model I, Sub Model II according to an embodiment.
Figure 22:
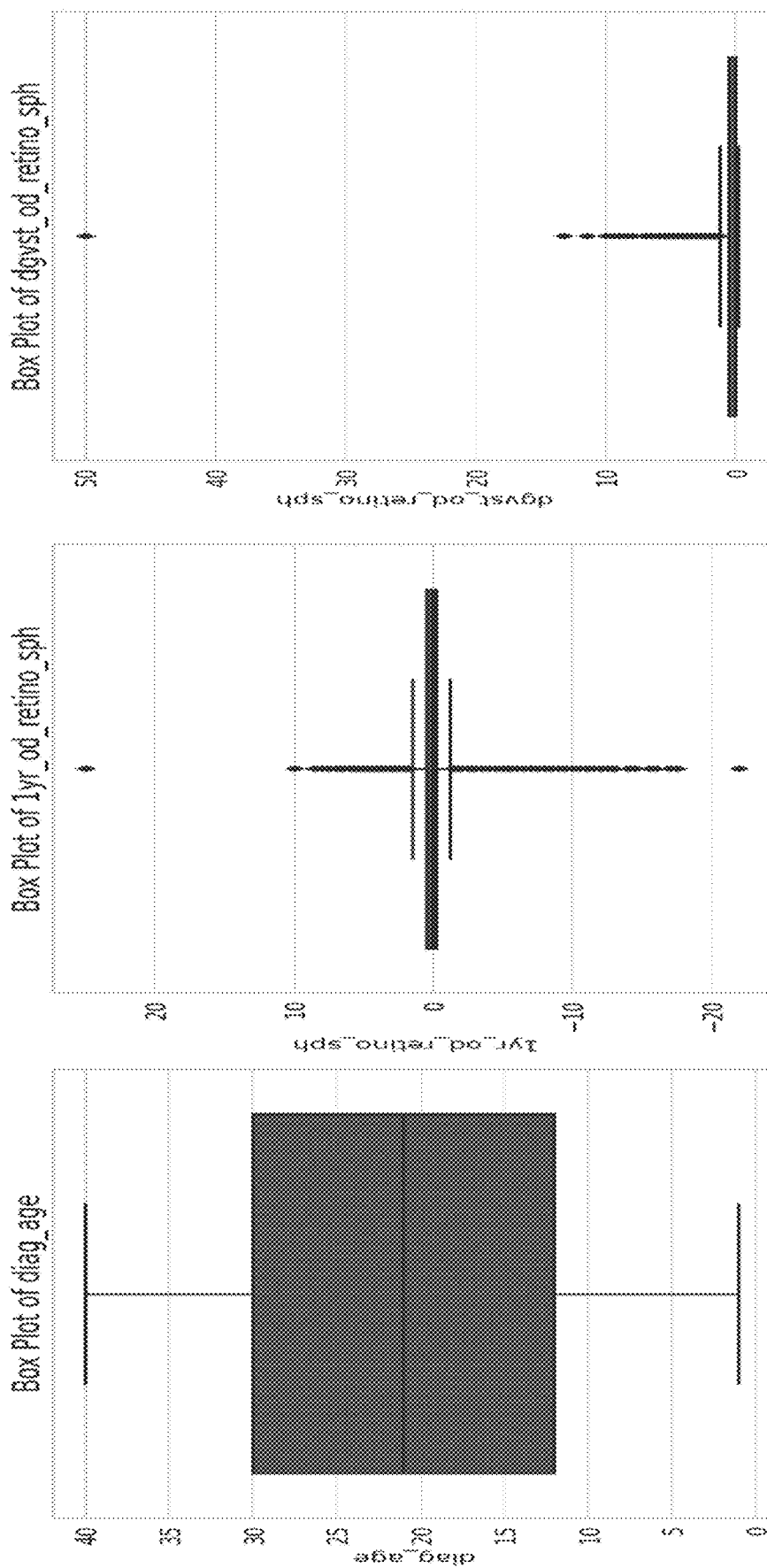
FIG. 22 shows Model I, Sub Model II performance analysis according to an embodiment.

FIG. 21 and FIG. 22 shows Model I, Sub Model II performance analysis according to an embodiment.

Histogram: Shows a broad distribution of ages at diagnosis, with a peak indicating a higher frequency of diagnoses in younger individuals. The presence of a skew towards younger ages suggests that near-sightedness may be more commonly diagnosed in younger populations.

The distribution of spherical values at the 1-year follow-up shows a concentration of values around less negative and zero values, indicating a range of near-sightedness severity among individuals. The spread includes both mild and severe near-sightedness, with a skew towards milder cases.

Spherical Values at Diagnosis and Follow-up: Both distributions suggest that near-sightedness severity varies widely among individuals, with a range from mild to severe cases. The consistency in the pattern of distribution from diagnosis to follow-up suggests that while there may be changes in severity, the overall profile of near-sightedness severity within the population remains broad.

Module 2 Trained with Data Stream II to Develop Model II

Early detection and management of myopia presents significant challenges in ophthalmology, especially when critical determinants such as spherical, cylindrical, and axis measurements are unavailable. Traditional approaches to predicting the onset and progression of myopia often rely heavily on these quantitative ocular measurements, leaving a gap in risk assessment for individuals lacking comprehensive eye examination data. This limitation is particularly acute in settings where access to advanced ophthalmic diagnostic tools is limited or in populations that have not undergone recent eye examinations.

FIG. 23 shows Data stream II for development of Model II according to an embodiment.

Myopia-informed AI models to identify the patients at risk of development of myopia without having information about key determinants of myopia sphere, cylinder, axis. AI models identify the patients at risk of progression of myopia. Model II is built and trained to detect presence, severity and progression of myopia.

In an embodiment, AI models are trained on ocular characteristics and patient characteristics comprising clinical data, medical data, and demographic data.

Clinical validation: Model II which is early detection and management of myopia model effectiveness is validated against patients records having one year follow up visits with ophthalmologists' assessment regarding myopia, and models have shown promising performance in early detection of myopia.

Model II comprises three Sub models, Sub Model I, Sub Model II, and Sub Model III.

Model II Sub Model I detects the presence of myopia
Model II Sub Model II predicts the severity of myopia
Model II Sub Model III estimates the progression of myopia Sub Model I for Detecting the Presence of Myopia and Predicting Likelihood of Myopia FIG. 24 and FIG. 25 show Model II, Sub-Model I performance analysis according to an embodiment. The outcome of the model is to detect Myopic or Non-Myopic. Developed and evaluated multiple machine learning models using the data to perform binary classification with two labels (Myopic/Non-Myopic) using 13 features. In an embodiment, the decision tree model is selected as it offers performance (accuracy of 87%), stability, and ability to handle heterogenous data with noise. The model is trained on the curated baseline dataset of 280,166 patient records and 13 features.

Sub Model II for Predicting Severity (Magnitude) of Myopia

FIG. 26 and FIG. 27 show Model II, Sub-Model II, performance analysis according to an embodiment. The outcome of the model is magnitude of myopia provided as Emmetropia, Simple, Moderate, or High Myopia. Developed and evaluated multiple machine learning models use the data to perform multi-class classification with four labels (Emmetropia, Simple Myopia, Moderate Myopia, or High Myopia) using 13 features.

Decision tree model is selected as it offers performance (accuracy of 91%), stability, and versatility in handling multiple labels, compatibility with data.

The model is trained on the curated baseline dataset of 2,20,000 patient records and 13 features.

Sub Model III Predicts Progression of Myopia

In an embodiment, the model is configured for predicting severity (magnitude) of myopia progression in 12 months.

FIG. 28 shows Model II, Sub-Model III, performance analysis according to an embodiment. Outcome of the model stratification of Myopia progression: Low/Medium/High Risk of Progression. Given the outcomes from the Model 1 (Myopia prediction) and Model 2 (Magnitude Prediction) risk stratification is computed and determined with respect to progression. This is evaluated using 1-year follow up visit data records of approx. ~12000 patients for testing the model's ability in estimation of progression. Filtered patient records are having progression towards myopia in the follow-up year with reference to baseline visit. Model offers reliable performance (accuracy of 83%) and 13 features.

In an embodiment, the AI/ML models chosen are Explanatory AI, also known as Explainable AI (XAI). It refers to AI systems designed to provide clear, interpretable, and understandable explanations of their decisions, predictions, and actions. This transparency is required for building trust, ensuring accountability, and facilitating the effective use of AI in critical applications. Explanatory AI aims to demystify the "black box" nature of many machine learning models, making their inner workings and decision-making processes accessible to humans. The XAI has subsystem within that uses natural language generation (NLG) to automatically generate explanatory notes or summaries that accompany each prediction, detailing the factors influencing the model's decision. The system uses AI-driven visualization tools that can dynamically generate graphical representations of patient data and model predictions, tailored to highlight the most relevant information based on the user's focus or queries.

For myopia prediction, an explanatory AI system may be used to help eye care professionals understand why certain patients are at risk of developing or progressing in myopia. For example, the AI model predicts that a particular patient has a high likelihood of myopia progression. An explanatory AI system could provide insights into the factors contributing to this prediction. For example, the system might generate a report highlighting that the patient's ocular measurements, such as a high cup-to-disc ratio, coupled with their medical history of prolonged device screen exposure and low outdoor activity levels, are significant contributors to the increased risk. It might also illustrate how each feature (e.g., age, genetic factors, screen time) influences the prediction through visual aids like feature importance scores or decision trees. An advanced module is equipped with Natural Language Generation (NLG) to automatically create detailed, understandable explanations of diagnostic predictions. This module contextualizes data insights and enhances decision-making processes by providing healthcare professionals with clear, actionable intelligence. By providing these explanations, the XAI system not only helps doctors understand the rationale behind the predictions but also supports them in making informed decisions about personalized treatment strategies and preventive measures for myopia. This transparency in prediction enhances the confidence of both the patients and the healthcare providers in the AI-driven recommendations, leading to better patient outcomes.

Figure 29A:
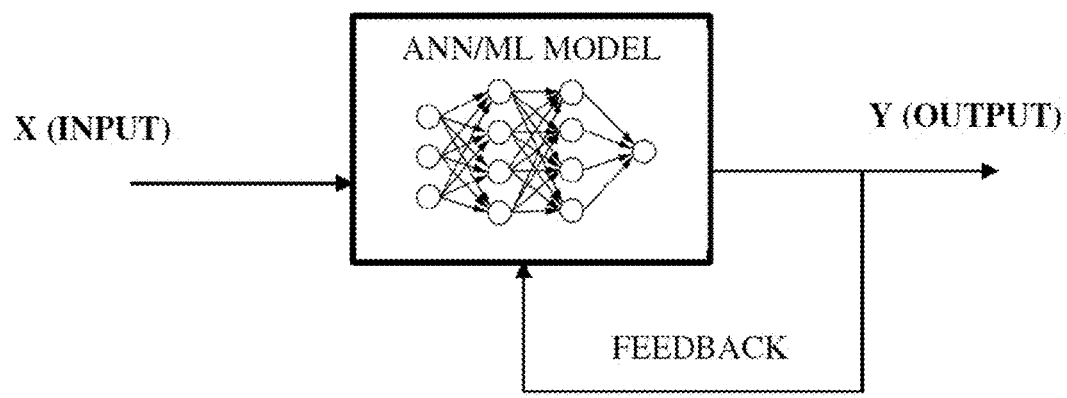
FIG. 29A shows a structure of the neural network/machine learning model with a feedback loop.

FIG. 29A shows a structure of the neural network/machine learning model with a feedback loop. Artificial neural networks (ANNs) model comprises an input layer, one or more hidden layers, and an output layer. Each node, or artificial neuron, connects to another and has an associated weight and threshold. If the output of any individual node is above the specified threshold value, that node is activated, sending data to the next layer of the network. Otherwise, no data is passed to the next layer of the network. A machine learning model or an ANN model may be trained on a set of data to take a request in the form of input data, make a prediction on that input data, and then provide a response. The model may learn from the data. Learning can be supervised learning and/or unsupervised learning and may be based on different scenarios and with different datasets. Supervised learning comprises logic using at least one of a decision tree, logistic regression, and support vector machines. Unsupervised learning comprises logic using at least one of a k-means clustering, a hierarchical clustering, a hidden Markov model, and an apriori algorithm. The output layer may predict or detect a health issue and the severity of the health issue based on the input data.

In an embodiment, ANNs may be a Deep-Neural Network (DNN), which is a multilayer tandem neural network comprising Artificial Neural Networks (ANN), Convolution Neural Networks (CNN) and Recurrent Neural Networks (RNN) that can recognize features from inputs, do an expert review, and perform actions that require predictions, creative thinking, and analytics. In an embodiment, ANNs may be Recurrent Neural Network (RNN), which is a type of Artificial Neural Networks (ANN), which uses sequential data or time series data. Deep learning algorithms are commonly used for ordinal or temporal problems, such as language translation, Natural Language Processing (NLP), speech recognition, and image recognition, etc. Like feedforward and convolutional neural networks (CNNs), recurrent neural networks utilize training data to learn. They are distinguished by their "memory" as they take information from prior input via a feedback loop to influence the current input and output. An output from the output layer in a neural network model is fed back to the model through the feedback. The variations of weights in the hidden layer(s) will be adjusted to fit the expected outputs better, while training the model. This will allow the model to provide results with far fewer mistakes.

The neural network is featured with the feedback loop to adjust the system output dynamically as it learns from the new data. In machine learning, backpropagation and feedback loops are used to train an AI model and continuously improve it upon usage. As the incoming data that the model receives increases, there are more opportunities for the model to learn from the data. The feedback loops, or backpropagation algorithms, identify inconsistencies and feed the corrected information back into the model as an input.

Even though the AI/ML model is trained well, with large sets of labelled data and concepts, after a while, the models' performance may decline while adding new, unlabelled input due to many reasons which include, but not limited to, concept drift, recall precision degradation due to drifting away from true positives, and data drift over time. A feedback loop to the model keeps the AI results accurate and ensures that the model maintains its performance and improvement, even when new unlabelled data is assimilated. A feedback loop refers to the process by which an AI model's predicted output is reused to train new versions of the model.

Initially, when the AI/ML model is trained, a few labelled samples comprising both positive and negative examples of the concepts (for e.g., myopia or no myopia) are used that are meant for the model to learn. Afterward, the model is tested using unlabelled data. By using, for example, deep learning and neural networks, the model can then make predictions on whether the desired concept/s (for e.g., myopia condition in future) are in unlabelled images. Each image is given a probability score where higher scores represent a higher level of confidence in the models' predictions. Where a model gives an image a high probability score, it is auto-labelled with the predicted concept. However, in the cases where the model returns a low probability score, this input may be sent to a controller (maybe a physician) which verifies and, as necessary, corrects the result. The human moderator may be used only in exception cases. The feedback loop feeds labelled data, auto-labelled or controller-verified data back to the model dynamically and is used as training data so that the system can improve its predictions in real-time and dynamically.

Figure 29B:
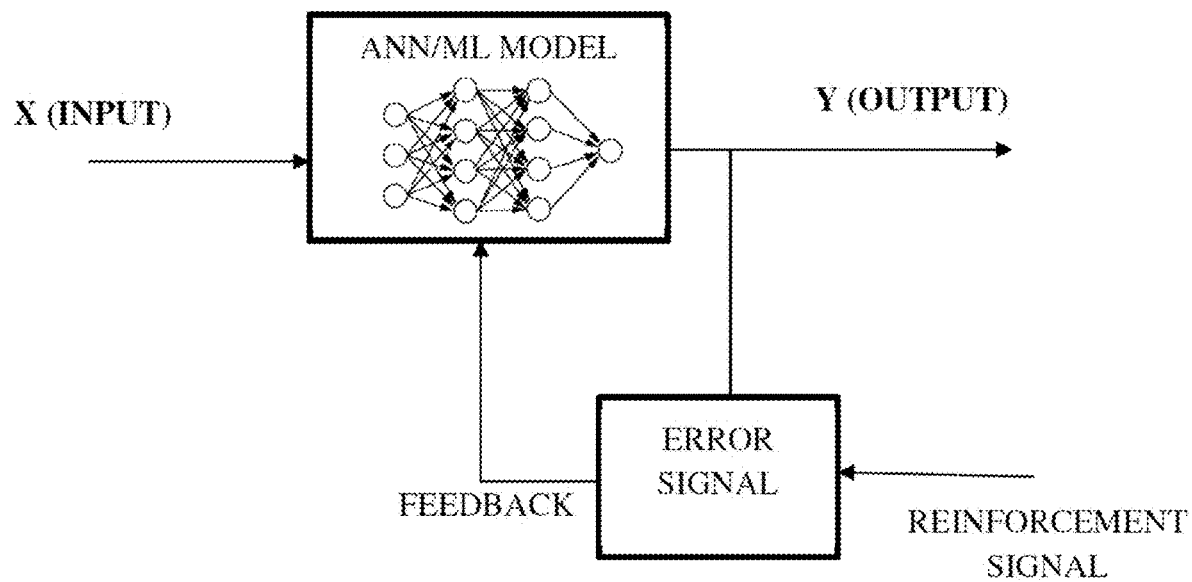
FIG. 29B shows a structure of the neural network/machine learning model with reinforcement learning.

FIG. 29B shows a structure of the neural network/machine learning model with reinforcement learning. The network receives feedback from authorized networked environments. Though the system is similar to supervised learning, the feedback obtained in this case is evaluative not instructive, which means there is no teacher as in supervised learning. After receiving the feedback, the network performs adjustments of the weights to get better predictions in the future. Machine learning techniques, like deep learning, allow models to take labeled training data and learn to recognize those concepts in subsequent data and images. The model may be fed with new data for testing, hence by feeding the model with data it has already predicted over, the training gets reinforced. If the machine learning model has a feedback loop, the learning is further reinforced with a reward for each true positive of the output of the system. Feedback loops ensure that AI results do not stagnate. By incorporating a feedback loop, the model output keeps improving dynamically and over usage/time.

All the ocular data, medical, clinical, historical, genetic data, external factor, SDOH and other data captured about the patient is considered as input X to the AI model and outcome of the AI model is denoted by Y which is one or more of identifying likelihood to have myopia, estimate severity and magnitude, predicting the risk of progression of the detected myopia, predicting the risk of developing myopia in the future, and predicting the risk of progression for future conditions of myopia. The output may further comprise treatment strategies, treatment options, appointment schedule generation.

In an embodiment, graphs on a graphical user interface (GUI) for the physicians are re-arranged based on a priority score of the content of the message. The processor tracks the risk scores and contributing factors for a given patient and generates them on the display based on their contribution. Further, for each risk, the contributing factors may be displayed in decreasing importance. In an embodiment, top five contributors may be shown. The system's user interface employs generative AI to create dynamic visualizations and narrative summaries, which elucidate the model's predictions in an accessible and intuitive way. These advancements are specifically tailored to assist clinicians by simplifying the interpretation of complex data sets and facilitating rapid and well-informed decision-making. This enhanced interface enables a more efficient diagnostic process, ensuring that healthcare professionals can easily grasp and act on the insights provided by the AI-driven analyses.

Use the AI Model(s):

The final step involves deploying the trained AI models for practical use. These models are applied to new, unseen data to make predictions, provide insights, or assist in decision-making processes. The models can be integrated into systems where they continuously process incoming data and generate outputs that support various applications, such as healthcare diagnostics, financial forecasting, or any other domain-specific tasks.

The figure represents a workflow for developing AI solutions. Starting with raw data acquisition, the process moves through feature extraction and model building, culminating in the practical application of AI models. Each step ensures the models are well-trained and capable of providing valuable outputs. This systematic approach ensures that the AI models are robust, accurate, and effective in addressing the specific problems they are designed to solve.

Predicting the output: Generate or output a myopia detection score using machine learning approaches; Generate or output a myopia progression score based on the predictions of the machine learning model; Generate or output the myopia detection score, myopia progression score, factors contributing to the myopia and progression of myopia for use in diagnosing and tracking its progression.

In an embodiment, the system predicts myopia onset and progression, incorporating environmental and behavioral data to adjust the health risk assessments dynamically.

Myopia-Informed AI System for Eye care involves,

Longitudinal data collection and model refinement. in which Data Infrastructure Development; Longitudinal Study Design; Preliminary Data Analysis are performed.

Data Enrichment and Model Refinement is performed to expand the dataset and refine predictive models with new inputs.

Environmental and Behavioral Data is integrated; model is configured for continuous Learning Mechanism;

Model is Validated and Optimized in a controlled setting and optimized for clinical application for Validation Study; Model Optimization; and Feedback Integration.

Models are deployed in clinical settings and healthcare professionals are trained in their use.

AI models are integrated into the system for Healthcare Professional Training and deployment.

Implement the AI system across multiple clinical settings and establish ongoing monitoring and improvement mechanisms for Continuous Performance Monitoring and Iterative Improvement.

Key Performance Indicators (KPIs): Accuracy and reliability of predictive models; user adoption rates and satisfaction among healthcare professionals; impact on patient outcomes, including early detection rates and effectiveness of personalized management plans; efficiency gains in clinical workflows and decision-making processes.

The development of the system involves foundational stages of data collection and model development to full-scale clinical deployment and continuous improvement, ensuring the delivery of significant benefits to ocular health management.

According to an embodiment, it is a method for extracting and analyzing ocular characteristics from digital images utilizing deep learning techniques, comprising preprocessing digital images to enhance ocular region visibility; employing a convolutional neural network (CNN) tailored for ocular region detection and feature extraction.

According to an embodiment, it is an integrated system for comprehensive ocular health assessment, comprising a multimodal data fusion module designed to synergistically combine ocular characteristics with external factors such as device screen exposure, outdoor activity metrics, and social determinants of health (SDOH), using a unique algorithm to generate a holistic health embedding and a dynamic embedding adjustment mechanism that updates embeddings based on real-time environmental and behavioral data inputs.

According to an embodiment, it is an AI-based predictive framework for the onset and progression of myopia, comprising a dual-pathway AI model employing separate but interconnected neural networks for predicting the onset and progression of myopia, respectively, based on non-spherical ocular embeddings, with one pathway dedicated to binary myopia onset prediction and a second pathway to continuous progression rate estimation; and a learning adaptation module that dynamically adjusts the predictive model based on longitudinal patient data, enhancing prediction accuracy over time.

According to an embodiment, it is a method for calibrating and selecting AI models for myopia assessment using genetic algorithms, comprising evaluating AI model candidates against a set of performance criteria including prediction accuracy, computational efficiency, and adaptability to diverse patient data; and employing a genetic algorithm for model selection and calibration, optimizing the population of models over generations to select the most effective configuration for myopia detection and severity classification.

According to an embodiment, the method further incorporates adaptive filtering techniques to compensate for variations in image quality due to lighting conditions, ensuring consistent ocular characteristic extraction.

According to an embodiment, the dynamic embedding adjustment mechanism is further capable of learning from healthcare professional feedback, integrating clinical adjustments into the health embedding algorithm.

According to an embodiment, the AI-based predictive framework further comprises an external-factors impact assessment module that quantifies the influence of individual external factors on the model's predictions, providing insights into the relative importance of screen time, outdoor activity, and SDOH on myopia risk.

According to an embodiment, the method further involves the use of patient outcome data to refine genetic algorithm parameters, ensuring the selected AI model remains responsive to evolving epidemiological trends and patient demographics.

According to an embodiment, a user Graphical User Interface (GUI)/User Interface (UI) is provided for healthcare providers to visualize AI predictions of myopia onset and progression alongside environmental and behavioral risk factors linked to the system, facilitating a holistic approach to patient counselling and management.

According to an embodiment, the system may continuously monitor and capture real-time data of latent characteristics influencing myopia using a wearable device, to capture such data as blink rate, gaze direction, and ambient light exposure for comprehensive ocular health monitoring.

How Technical Solution is a Technological Advancement

The AI models developed provide actionable insights by identifying patients at risk of developing and/or progressing in myopia, allowing for early and personalized intervention. The use of AI in this context transforms eye care by enhancing the precision of health assessments, enabling tailored treatment plans based on predictive risk scores, and improving the efficiency of eye care delivery through informed clinical decisions. This approach not only allows for early detection and prevention but also optimizes treatment strategies, ultimately leading to better patient outcomes and more efficient use of healthcare resources.

Predictive models allow for early identification of at-risk individuals, enabling proactive interventions that can slow or prevent the onset of myopia. Detection models ensure accurate diagnosis and ongoing monitoring of the condition. The dual framework approach not only enhances the precision and effectiveness of myopia management but also represents a notable advancement in the field of ophthalmology. The combined models enable personalized treatment plans that are tailored to both the immediate needs and future risks of patients. This results in more effective interventions and better patient outcomes.

When detection and prediction models for myopia are used individually, each addresses only a portion of the overall problem. Detection models focus on identifying the presence of myopia at the time of the test, providing valuable information for immediate intervention and management. However, detection models fall short in offering insights into the future risk of developing myopia or its progression, leading to reactive rather than proactive care. Prediction models, on the other hand, forecast the likelihood of developing or worsening myopia based on various risk factors, enabling preventive strategies and long-term planning. Yet, without current detection capabilities, these models might not accurately reflect the immediate needs of patients already experiencing myopia. Further, it is highly unlikely that a patient not having any symptoms will go to a predictive model, separately, to check for future risk.

When combined into a single system, detection and prediction models create a synergistic effect that offers a comprehensive approach to managing myopia. This integrated system can simultaneously identify current myopia cases and predict future risks, ensuring that patients receive both immediate treatment and preventive care. The combination allows for tailored treatment plans that address both present conditions and future threats, optimizing patient outcomes. By leveraging the strengths of both models, healthcare providers can implement a more effective and efficient care strategy, enhancing early interventions, continuous monitoring, and overall management of myopia. This holistic approach not only improves individual patient care but also advances the standard of eye health management through the use of advanced AI techniques.

Example 1: Early Myopia Detection and Monitoring

The Myopia Informed Artificial Intelligence System leverages advanced machine learning algorithms to analyze patient data, including genetic markers, lifestyle factors, and visual acuity tests. It outputs a Myopia Risk Score ranging from 0 to 1, indicating the likelihood of a patient developing myopia within the next year. The system categorizes the risk into low, medium, or high.

With the Myopia Risk Score and its categorization, optometrists can take preemptive measures to mitigate the onset of myopia in high-risk patients. Interventions might include prescribing low-dose atropine eye drops, recommending increased time spent outdoors to reduce near-work activities, and advising the use of specially designed myopia control contact lenses or glasses.

For patients at medium or low risk, regular monitoring and routine eye examinations are sufficient. This targeted approach ensures that resources are efficiently allocated towards patients most likely to benefit from early intervention, potentially slowing or preventing the progression of myopia and reducing the need for more intensive treatments in the future including a new/stronger prescription of eyeglasses.

Example 2: Myopia Progression Prediction and Management

The Myopia Progression Analyzer (MPA) of Myopia Informed Artificial Intelligence System processes input data from previous eye examinations, family history, and lifestyle factors to generate a Myopia Progression Score, a value between 0 and 1, predicting the rate at which a child's myopia is likely to progress over the next year. The system further categorizes the progression risk into low, medium, or high.

Using the Myopia Progression Score, eye care professionals can develop personalized management plans for patients. For children with a high progression risk, proactive steps such as increasing the frequency of eye exams, implementing myopia control therapies like orthokeratology (overnight reshaping lenses), and recommending time limits on screen use are advisable.

For those with a moderate or low risk, regular monitoring and educational advice to maintain good visual habits may suffice. This predictive approach allows for early intervention in high-risk cases, potentially reducing the severity of myopia progression and improving long-term visual outcomes.

Example 3: Post-Treatment Myopia Stability Assessment

The Myopia Stability Assessment Tool evaluates data from patients who have undergone myopia treatment, such as Laser-Assisted In Situ Keratomileusis (LASIK®) surgery or orthokeratology, to predict the likelihood of stable vision or regression. The tool outputs a Stability Score from 0 to 1 and classifies the stability as high, medium, or low.

With the Stability Score, clinicians can determine the need for follow-up care and adjustments to the treatment plan. Patients with a low stability score might require more frequent check-ups and potential additional treatments to maintain their corrected vision.

For patients with high stability scores, routine monitoring may be sufficient, indicating that the current treatment is effectively maintaining vision correction. This assessment helps optimize post-treatment care, ensuring that resources are focused on those needing further intervention, while minimizing unnecessary appointments for those with stable vision.

Example 4: Preventive Myopia Care in Children

The Myopia Prevention System integrates input data from various sources, including genetic predisposition, environmental factors, and eye health records, to compute a Preventive Myopia Care Score. This score, ranging from 0 to 1, indicates the probability of a child developing myopia based on current lifestyle and environmental conditions, categorized into low, medium, or high risk.

With this score, pediatric eye care specialists can advise parents on preventive strategies tailored to the child's risk level. For high-risk children, interventions could include promoting outdoor activities, implementing regular eye breaks during near work, and providing guidance on reducing screen time.

For children at moderate or low risk, general advice on maintaining a balanced visual environment and periodic eye check-ups may be recommended. This proactive approach allows for the customization of preventive care, potentially delaying or averting the onset of myopia, and supports long-term ocular health.

Example 5: Myopia-Related Retinal Health Monitoring

The Myopia Informed Artificial Intelligence System utilizes data from detailed retinal imaging and historical health records to predict the risk of myopia-related retinal complications, such as retinal detachment or macular degeneration. The system generates a Retinal Risk Score between 0 and 1 and classifies it into low, medium, or high risk.

With the Retinal Risk Score, ophthalmologists can identify patients at high risk for developing serious retinal conditions. High-risk patients might benefit from more frequent retinal examinations, advanced imaging techniques, and potential preventative treatments or surgical interventions to mitigate the risk of retinal damage.

For patients with a lower risk score, regular eye health monitoring and routine examinations are sufficient. This focused monitoring ensures that those most at risk receive the necessary attention to prevent severe complications.

According to an embodiment, disclosed is a system comprising a processor storing instructions in non-transitory memory that, when executed, cause the processor to receive, via an input module, an input data, wherein the input data comprises an image of an ocular region of a user, clinical data of the user, and external factors; extract, using an image processing module comprising adaptive filtering techniques, ocular characteristics, wherein the ocular characteristics comprise one or more of Optic Disc Size, Cup Disc Ratio, Optic Disc, Fundus, IOP, Ocular Alignment, Tor CA unaided, BCVA, SPH, Cyl, Tor fr corr axis; combine, using a multimodal fusion module, the input data to determine a holistic health embedding; detect, based on a machine learning model and the holistic health embedding, a first output, wherein the first output comprises likelihood of myopia, and severity of myopia; predict, based on the machine learning model and the holistic health embedding, a second output, wherein the second output comprises an onset of myopia and a progression of myopia in the user; stratify, risk category of myopia of the user; display, on a user interface, one or more of the first output and the second output; receive, a first feedback of the first output and the second output from the machine learning model, to dynamically adjust an accuracy of the first output and the second output from the machine learning model; receive, a second feedback from a physician, to dynamically adjust the accuracy of the first output and the second output from the machine learning model; and wherein the machine learning model is a pre-trained model with a data set comprising the input data from plurality of patients to recognize one or more patterns using the holistic health embedding.

According to an embodiment of the system, the system is further configured to extract and analyze the ocular characteristics from digital images utilizing deep learning techniques, comprising preprocessing the digital images to enhance ocular region visibility; and employing a convolutional neural network (CNN) tailored for ocular region detection and feature extraction.

According to an embodiment of the system, the system is configured for comprehensive ocular health assessment.

According to an embodiment of the system, the system further comprises a multimodal data fusion module designed to combine the ocular characteristics with the external factors using the machine learning model to generate the holistic health embedding.

According to an embodiment of the system, the system has generative artificial intelligence module to preprocess and enhance the quality of multimodal data inputs for the detection and prognosis of myopia.

According to an embodiment of the system, a dynamic embedding adjustment mechanism is configured to update the holistic health embedding based on real-time environmental and behavioral data inputs of the user, wherein the dynamic embedding adjustment is continuous and adaptive, modifying vector representations of data, in response to new information or changes in underlying data distribution.

According to an embodiment of the system, the dynamic embedding adjustment mechanism is further capable of learning from the second feedback of the physician and integrating clinical adjustments into the machine learning model.

According to an embodiment of the system, the machine learning model comprises an AI based predictive framework for the onset and progression of myopia, wherein the AI based predictive framework comprises a dual-pathway AI model employing separate, but interconnected, neural networks for predicting the onset and progression of myopia, based on non-spherical ocular embeddings, with one pathway dedicated to binary myopia onset prediction and a second pathway dedicated to a continuous progression rate estimation.

According to an embodiment of the system, the system further comprises a learning adaptation module that dynamically adjusts the AI based predictive framework based on longitudinal patient data and/or a longitudinal patient record, configured to enhance prediction accuracy over time, wherein the longitudinal data is a data that is collected over a period of time from the user.

According to an embodiment of the system, the system further includes an external factors impact assessment module that quantifies the influence of individual external factors on the first output and the second output.

According to an embodiment of the system, the external factors comprise one or more of device screen exposure time, outdoor activity metrics, and social determinants of health on myopia risk.

According to an embodiment of the system, the pre-trained model is calibrated and selected from one or more AI models for myopia assessment using genetic algorithms by evaluating AI model candidates against a set of performance criteria.

According to an embodiment of the system, the set of performance criteria comprise prediction accuracy, computational efficiency, and adaptability to diverse patient data.

According to an embodiment of the system, the system is further configured to use patient outcome data to refine parameters of the genetic algorithm.

According to an embodiment of the system, the adaptive filtering techniques are performed to compensate for variations in image quality due to lighting conditions.

According to an embodiment of the system, the user interface is configured for healthcare providers to visualize the first output and the second output alongside the input that is contributing to the first output and the second output, facilitating a holistic approach to patient counselling and treatment management.

According to an embodiment of the system, the system is further configured to collect data from a wearable device for real-time data capture of latent characteristics influencing myopia comprising blink rate, gaze direction, and ambient light exposure.

According to an embodiment of the system, the machine learning model comprises one or more of logistic regressions, support vector machines (SVM), K-nearest neighbors, decision trees, and ensemble models.

According to an embodiment of the system, the ensemble model comprises one or more of random forests, extra trees, and bagging.

According to an embodiment of the system, the clinical data comprises one or more of clinical observations made by healthcare, diagnostic test results, and treatment information, health monitoring data, behavioral and lifestyle information, and patient-reported outcomes.

According to an embodiment of the system, the clinical data further comprises patient reported outcomes.

According to an embodiment of the system, the first output further comprises a prediction of progress rate.

According to an embodiment of the system, the holistic health embedding is a multidimensional representation of a health profile of the user.

According to an embodiment of the system, the system may further provide a third output comprising one or more of treatment strategies, treatment options, appointment schedule generation.

According to an embodiment of the system, the machine learning model is configured to learn using labelled data using a supervised learning, wherein the supervised learning comprises logic using at least one of a decision tree, a logistic regression, a support vector machine, a k-nearest neighbors, a Naïve Bayes, a random forest, a linear regression, and a polynomial regression.

According to an embodiment of the system, the system further comprises artificial intelligence driven models for generating explanatory narratives and dynamic visual representations based on the first output and the second output.

According to an embodiment of the system, the machine learning model is configured to learn from real-time data using an unsupervised learning, wherein the unsupervised learning comprises logic using at least one of a k-means clustering, a hierarchical clustering, a hidden Markov model, and an apriori algorithm.

According to an embodiment of the system, the machine learning model has a feedback loop, wherein the first output and the second output from a previous step is fed back to the model in real-time to improve performance and accuracy of the output of a next step.

According to an embodiment of the system, the machine learning model comprises a recurrent neural network model.

According to an embodiment of the system, the machine learning model has a feedback loop, wherein learning is further reinforced with a reward for each true positive of the output of the system.

According to an embodiment, disclosed is a method comprising, receiving, via an input module, an input data, wherein the input data comprises an image of an ocular region of a user, clinical data of the user, and external factors; extracting, using an image processing module comprising adaptive filtering techniques, ocular characteristics, wherein the ocular characteristics comprise one or more of Optic Disc Size, Cup Disc Ratio, Optic Disc, Fundus, IOP, Ocular Alignment, Tor CA unaided, BCVA, SPH, Cyl, Tor fr corr axis; combining, using a multimodal fusion module, the input data to determine a holistic health embedding; detecting, based on a machine learning model and the holistic health embedding, a first output, wherein the first output comprises likelihood of myopia, and severity of myopia; predicting, based on the machine learning model and the holistic health embedding, a second output, wherein the second output comprises an onset of myopia and a progression of myopia in the user; stratifying, risk category of myopia of the user; displaying, on a user interface, one or more of the first output and the second output; receiving, a first feedback of the first output and the second output from the machine learning model, to dynamically adjust an accuracy of the first output and the second output from the machine learning model; receiving, a second feedback from a physician, to dynamically adjust the accuracy of the first output and the second output from the machine learning model; and wherein the machine learning model is a pre-trained model with a data set comprising the input data from plurality of patients to recognize one or more patterns using the holistic health embedding.

According to an embodiment of the method, the external factors comprise one or more of device screen exposure time, outdoor activity metrics, and social determinants of health.

According to an embodiment of the method, the user interface is configured for healthcare providers to visualize the first output and the second output alongside the input that is contributing to the first output and the second output, facilitating a holistic approach to patient counselling and treatment management.

According to an embodiment of the method, the machine learning model comprises one or more of logistic regressions, support vector machines (SVM), K-nearest neighbors, decision trees, and ensemble models.

According to an embodiment of the method, the ensemble model comprises one or more of random forests, extra trees, and bagging.

According to an embodiment, disclosed is a non-transitory computer-readable medium having stored thereon instructions executable by a computer system to perform operations comprising receiving, via an input module, an input data, wherein the input data comprises an image of an ocular region of a user, clinical data of the user, and external factors, wherein the external factors comprise one or more of device screen exposure time, outdoor activity metrics, and social determinants of health; extracting, using an image processing module comprising adaptive filtering techniques, ocular characteristics, wherein the ocular characteristics comprise one or more of Optic Disc Size, Cup Disc Ratio, Optic Disc, Fundus, IOP, Ocular Alignment, Tor CA unaided, BCVA, SPH, Cyl, Tor fr corr axis; combining, using a multimodal fusion module, the input data to determine a holistic health embedding; detecting, based on a machine learning model and the holistic health embedding, a first output, wherein the first output comprises likelihood of myopia, and severity of myopia; predicting, based on the machine learning model and the holistic health embedding, a second output, wherein the second output comprises an onset of myopia and a progression of myopia in the user; stratifying, risk category of myopia of the user; displaying, on a user interface, one or more of the first output and the second output; receiving, a first feedback of the first output and the second output from the machine learning model, to dynamically adjust an accuracy of the first output and the second output from the machine learning model; receiving, a second feedback from a physician, to dynamically adjust the accuracy of the first output and the second output from the machine learning model; and wherein the machine learning model is a pre-trained model with a data set comprising the input data from plurality of patients to recognize one or more patterns using the holistic health embedding.

According to an embodiment of the non-transitory computer-readable medium, the external factors comprise one or more of device screen exposure time, outdoor activity metrics, and social determinants of health.

Figure 30:
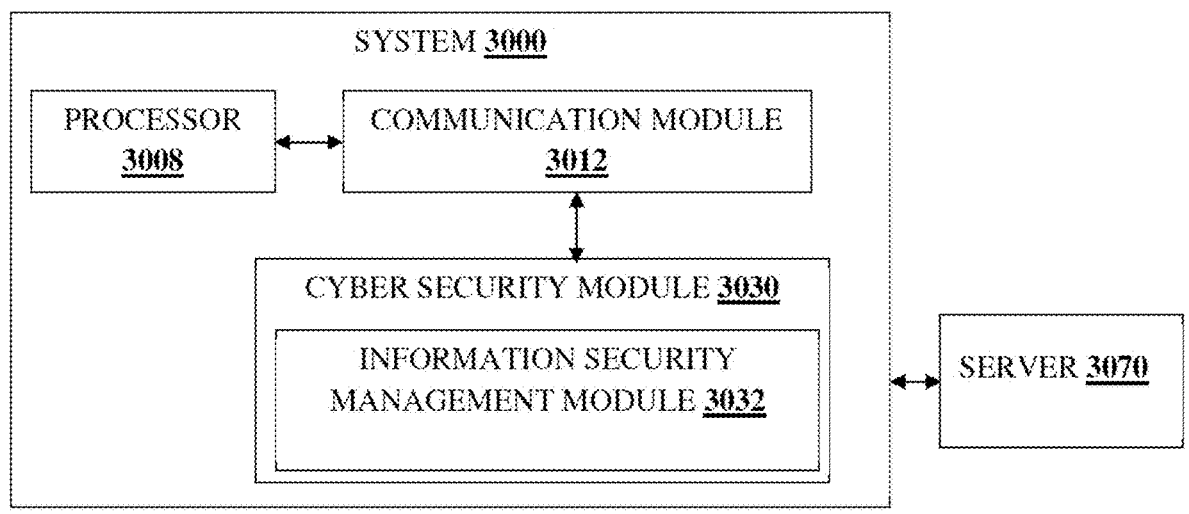
FIG. 30 shows a block diagram of the cyber security module in view of the system and server.

According to an embodiment, the data that is accessed/received via various sources and the data that is transmitted to cloud or via network is secured using a cybersecurity module. FIG. 30 shows the block diagram of the system 3000 comprising a cyber security module 3030 and a processor 3008 according to an embodiment. The communication of data between the system 3000 and the server 3070 through the communication module 3012 is first verified by the information security management module 3032 before being transmitted from the system to the server or from the server to the system. The information security management module is operable to analyze the data for potential cyber security threats, to encrypt the data when no cyber security threat is detected, and to receive or transmit the data encrypted to the system or the server.

In an embodiment, the system may comprise a cyber security module. In one aspect, a secure communication management (SCM) computer device for providing secure data connections is provided. The SCM computer device includes a processor in communication with memory. The processor is programmed to receive, from a first device, a first data message. The first data message is in a standardized data format. The processor is also programmed to analyze the first data message for potential cyber security threats. If the determination is that the first data message does not contain a cyber security threat, the processor is further programmed to convert the first data message into a first data format associated with the vehicle environment and transmit the converted first data message to the vehicle system using a first communication protocol associated with the vehicle system.

FIG. 31 shows a block diagram of the method implemented by the Myopia Informed Artificial Intelligence System according to an embodiment. According to an embodiment, disclosed is a method 3100 comprising, receiving, via an input module, an input data, wherein the input data comprises an image of an ocular region of a user, clinical data of the user, and external factors at step 3102; extracting, using an image processing module comprising adaptive filtering techniques, ocular characteristics, wherein the ocular characteristics comprise one or more of Optic Disc Size, Cup Disc Ratio, Optic Disc, Fundus, IOP, Ocular Alignment, Tor CA unaided, BCVA, SPH, Cyl, Tor fr corr axis at step 3104; combining, using a multimodal fusion module, the input data to determine a holistic health embedding at step 3106; detecting, based on a machine learning model and the holistic health embedding, a first output, wherein the first output comprises likelihood of myopia, and severity of myopia at step 3108; predicting, based on the machine learning model and the holistic health embedding, a second output, wherein the second output comprises an onset of myopia and a progression of myopia in the user at step 3110; stratifying, risk category of myopia of the user at step 3112; displaying, on a user interface, one or more of the first output and the second output at step 3114; receiving, a first feedback of the first output and the second output from the machine learning model, to dynamically adjust an accuracy of the first output and the second output from the machine learning model at step 3116; receiving, a second feedback from a physician, to dynamically adjust the accuracy of the first output and the second output from the machine learning model at step 3118; and wherein the machine learning model is a pre-trained model with a data set comprising the input data from plurality of patients to recognize one or more patterns using the holistic health embedding.

Figure 32:
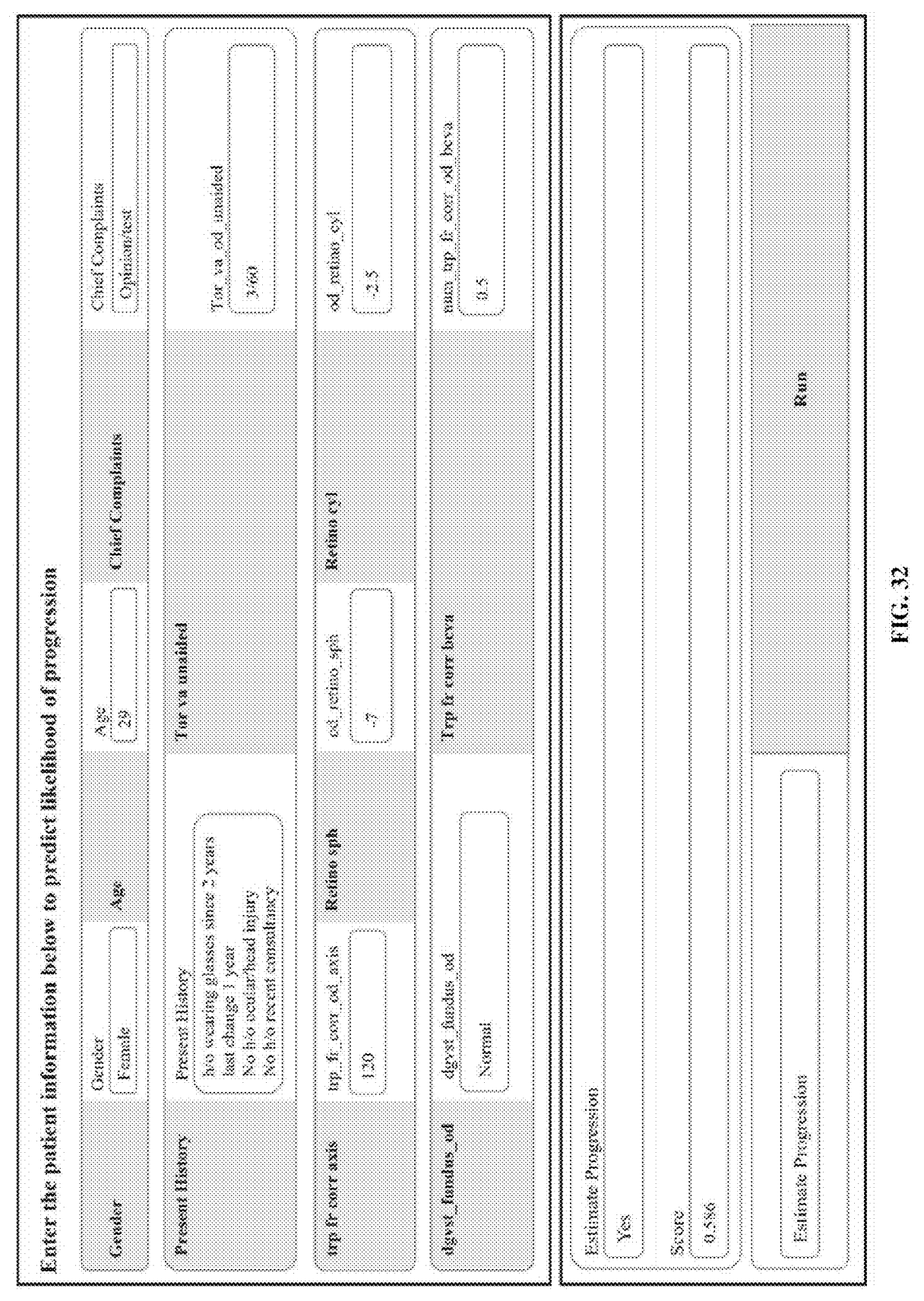

FIG. 32 shows a graphical user interphase (GUI) for myopia progression models of Myopia Informed Artificial Intelligence System. Module 1 trained with Data stream I to develop Model I is used to predict the myopia monitoring for development and progression by considering the input from the GUI as provided in FIG. 32.

Figure 33:
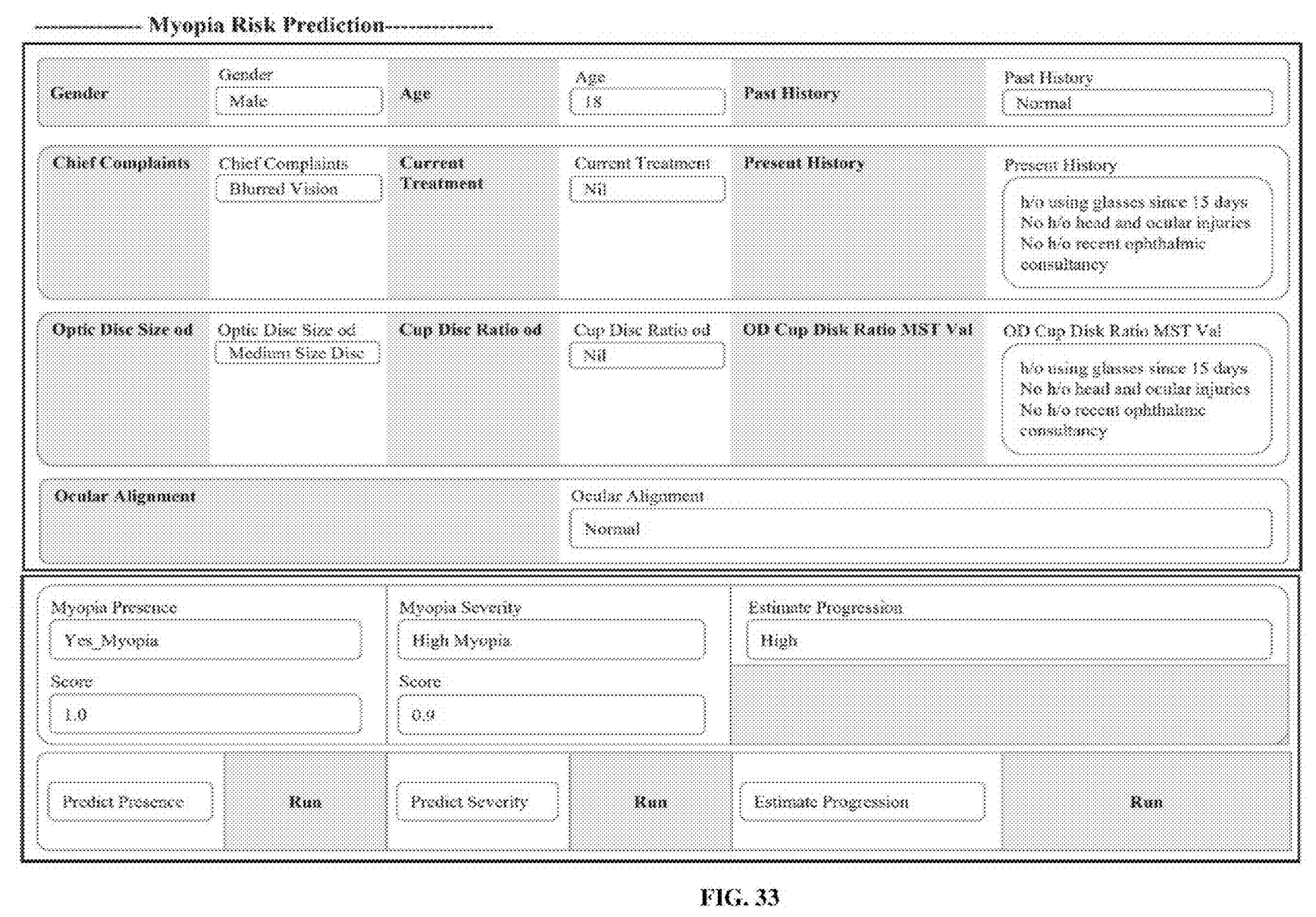

FIG. 33 shows a graphical user interphase for myopia risk prediction models of Myopia Informed Artificial Intelligence System. Module 2 trained with Data stream II to develop Model II is used for detecting the presence of myopia and predicting likelihood of Myopia, predicting severity (magnitude) of Myopia, and predicting the progression of myopia by considering the input from the GUI as provided in FIG. 33. In an embodiment, the user may also provide unique input elements from each model and the output is predicted from each of these modules is determined and presented to the user without the user having to operate two different GUI's. Single input stream considering all the elements from the GUIs is considered and all the relevant outputs are provided to the user from the dual-module framework.

According to an embodiment, disclosed is a method comprising, receiving, via an input module, an input data, wherein the input data comprises an image of an ocular region of a user, clinical data of the user, and external factors; extracting, using an image processing module comprising adaptive filtering techniques, ocular characteristics, wherein the ocular characteristics comprise one or more of Optic Disc Size, Cup Disc Ratio, Optic Disc, Fundus, IOP, Ocular Alignment, Tor CA unaided, BCVA, SPH, Cyl, Tor fr corr axis; combining, using a multimodal fusion module, the input data to determine a holistic health embedding; detecting, based on a machine learning model and the holistic health embedding, a first output, wherein the first output comprises likelihood of myopia, and severity of myopia;

predicting, based on the machine learning model and the holistic health embedding, a second output, wherein the second output comprises an onset of myopia and a progression of myopia in the user; stratifying, risk category of myopia of the user; displaying, on a user interface, one or more of the first output and the second output; interfacing, the user interface with generative artificial intelligence to produce dynamic visualizations and narrative summaries that explain model predictions in an intuitive manner configured to aid clinicians in interpreting complex data sets for making informed decisions; receiving, a first feedback of the first output and the second output from the machine learning model, to dynamically adjust an accuracy of the first output and the second output from the machine learning model; and receiving, a second feedback from a physician, to dynamically adjust the accuracy of the first output and the second output from the machine learning model; and wherein the machine learning model is a pre-trained model with a data set comprising the input data from plurality of patients to recognize one or more patterns using the holistic health embedding; and wherein the system is configured for myopia prognosis powered by multimodal data.

According to an embodiment of the system, the system comprises of refined algorithms powered by Generative AI modules to process multimodal data for utilized to preprocess and synthesize the input data captured in different formats and data types. This is essential for data enhancements of both images, structured and unstructured Electronic Health Records (EHRs). For preparing more robust dataset, which is crucial for training accurate predictive models.

The system's user interface leverages generative AI to generate dynamic visualizations and narrative summaries, simplifying the interpretation of complex data for clinicians and enabling quicker, more informed decision-making; receiving.

To advance the system's capability in processing and analyzing multimodal data, generative AI technologies are integrated to optimize data synthesis and preprocessing. Generative Adversarial Networks (GANs) are utilized to enhance the resolution and detail of ocular images and to generate synthetic instances of rare eye conditions not prevalent in the existing datasets, thereby expanding the diversity and robustness of data for training more comprehensive predictive models. Furthermore, transformers and autoencoders are deployed to extract and analyze features from unstructured clinical notes effectively. These models excel in understanding the context and relevant information embedded in textual data, transforming it into structured formats that are highly informative for predictive analytics. This implementation not only enriches the data quality but also enhances the system's predictive accuracy by providing a more nuanced understanding of complex eye health conditions.

Integrating generative AI with graphical user interfaces (GUIs) in predictive models of myopia can significantly enhance the user experience by providing personalized insights and interactive visualizations. The process begins with the collection and preparation of data relevant to myopia prediction, including patient demographics, genetic factors, lifestyle habits, and historical eye examination results. This data is then cleaned and preprocessed to ensure its suitability for model training, which involves normalization, handling missing values, and feature engineering.

The next step involves the development of both predictive and generative models. The predictive model is created using machine learning techniques such as decision trees, support vector machines, or neural networks, trained on the prepared dataset to predict the likelihood of myopia progression. Concurrently, a generative AI model is developed using techniques like Generative Adversarial Networks (GANs) or Variational Autoencoders (VAEs). This model simulates possible future scenarios or outcomes based on different intervention strategies, offering a dynamic tool for understanding the potential impacts of various treatment options.

These models are then integrated with the GUI. The GUI is designed to be user-friendly and intuitive, enabling users to easily interact with the predictive and generative models. Users can input data through the interface, which is then processed and analyzed by the models. The results, including predictions of myopia progression and simulated future scenarios, are presented in an accessible and visually appealing manner. This can include interactive charts, graphs, and other visual elements that allow users to explore different outcomes and understand the factors influencing myopia progression. Incorporating generative AI into the GUI also allows for real-time feedback and personalization. For example, the system can generate personalized reports and recommendations based on the user's specific data and predicted outcomes. This integration not only enhances the user's understanding of their condition but also supports more informed decision-making regarding treatment and lifestyle adjustments. In an embodiment, the system comprises a combination of generative AI and advanced GUIs in predictive models of myopia for personalized healthcare and patient engagement.

Generative AI enhances the understanding of input fields for clinicians and doctors by generating clear, context-specific explanations and translating them into local languages or dialects. This capability is particularly valuable in improving the accuracy of data entry, facilitating better communication, and ensuring that medical staff comprehensively understand the information they are working with. In a multi-national healthcare organization, doctors and clinicians are required to input patient data which include complex fields such as medical history, symptoms, diagnostic results, and treatment plans. Accurate understanding of these input fields is crucial, and the variability across regions adds an additional layer of complexity, especially when clinicians speak different languages or dialects. For instance, a generative AI system integrated into the system software can assist by providing detailed descriptions of the information required in each field. When a clinician hovers over an input field labeled "Patient's Chief Complaint," the AI might generate an explanation such as, "Please enter a brief description of the primary reason the patient is seeking medical attention, including key symptoms and duration." This explanation can then be translated into the clinician's local language. The generative AI system, equipped with advanced natural language processing (NLP) capabilities, interprets and translates medical terminology accurately, understanding regional nuances and medical jargon. These translations help clinicians enter data accurately and consistently, reducing language barriers and enhancing communication among medical staff from different regions. The generative AI integration and interface with the system offers numerous benefits, including improved data accuracy, enhanced communication, increased efficiency, and personalized assistance based on clinicians' language preferences and regional dialects.

The descriptions of the one or more embodiments are for purposes of illustration but are not exhaustive or limiting to the embodiments described herein. Many modifications and variations will be apparent to those of ordinary skill in the art without departing from the scope and spirit of the described embodiments. The terminology used herein best explains the principles of the embodiments, the practical application and/or technical improvement over technologies found in the marketplace, and/or to enable others of ordinary skill in the art to understand the embodiments described herein.

INCORPORATION BY REFERENCE

All references, including granted patents and patent application publications, referred herein are incorporated herein by reference in their entirety.

US Patent Publication Number U.S. Pat. No. 10,722, 180B2 titled, "Deep learning-based diagnosis and referral of ophthalmic diseases and disorders"

US Patent Publication Number U.S. Pat. No. 10,667, 680B2 titled, "Forecasting eye condition progression for eye patients"

US Patent Application Publication Number US20220165418A1 titled, "Image-based detection of ophthalmic and systemic diseases"

US Patent Application Publication Number US20210375460A1 titled, "Accurate prediction and treatment of myopic progression by artificial intelligence"

WIPO (PCT) Publication Number WO2023195919A3 titled, "Method for predicting risk of developing myopia"

WIPO (PCT) Publication Number WO2023079019A1 titled, "A method and system for determining a risk of an onset or progression of myopia"

WIPO (PCT) Publication Number WO2023079062A1 titled, "Devices and methods for determining data related to a progression of refractive values of a person"

What is claimed is:

1. A system comprising:
   a processor storing instructions in non-transitory memory that, when executed, cause the processor to:
   receive, via an input module, an input data, wherein the input data comprises an image of an ocular region of a user, clinical data of the user, and external factors;
   extract, using an image processing module comprising adaptive filtering techniques, ocular characteristics, wherein the ocular characteristics comprise one or more of Optic Disc Size, Cup Disc Ratio, Optic Disc, Fundus, IOP, Ocular Alignment, Tor CA unaided, BCVA, SPH, Cyl, Tor fr corr axis;
   combine, using a multimodal fusion module, the input data to determine a holistic health embedding;
   detect, based on a machine learning model and the holistic health embedding, a first output, wherein the first output comprises likelihood of myopia, and severity of myopia;
   predict, based on the machine learning model and the holistic health embedding, a second output, wherein the second output comprises an onset of myopia and a progression of myopia in the user;
   stratify, risk category of myopia of the user;
   display, on a user interface, one or more of the first output and the second output;
   receive, a first feedback of the first output and the second output from the machine learning model, to dynamically adjust an accuracy of the first output and the second output from the machine learning model; and
   receive, a second feedback from a physician, to dynamically adjust the accuracy of the first output and the second output from the machine learning model; and
   wherein the machine learning model is a pre-trained model with a data set comprising the input data from plurality of patients to recognize one or more patterns using the holistic health embedding; and
   wherein the system is configured for myopia prognosis powered by multimodal data.

2. The system of claim 1, wherein the system is further configured to extract and analyze the ocular characteristics from digital images utilizing deep learning techniques, comprising preprocessing the digital images to enhance ocular region visibility; and employing a convolutional neural network (CNN) tailored for ocular region detection and feature extraction.

3. The system of claim 1, wherein the multimodal fusion module is designed to combine the ocular characteristics with the external factors using the machine learning model to generate the holistic health embedding; and wherein the holistic health embedding is a multidimensional representation of a health profile of the user.

4. The system of claim 1, wherein the dynamic embedding adjustment mechanism is further capable of learning from the second feedback of the physician and integrating clinical adjustments into the machine learning model.

5. The system of claim 1, wherein the machine learning model comprises an artificial intelligence based predictive framework for the onset and progression of myopia, wherein the artificial intelligence based predictive framework comprises a dual-pathway employing separate but interconnected neural network models for predicting the onset and progression of myopia, based on non-spherical ocular embeddings, with one pathway dedicated to binary myopia onset prediction and a second pathway to continuous progression rate estimation.

6. The system of claim 5, wherein the system further comprises a learning adaptation module that dynamically adjusts the artificial intelligence based predictive framework based on a longitudinal patient data and configured to enhance prediction accuracy over time; and wherein the longitudinal patient data is a data that is collected over a period of time from the user.

7. The system of claim 1, wherein the system further includes an external factors impact assessment module that quantifies an influence of the external factors on the first output and the second output; and wherein the external factors comprise one or more of device screen exposure time, outdoor activity metrics, and social determinants of health on myopia risk.

8. The system of claim 1, wherein the adaptive filtering techniques are performed to compensate for variations in image quality due to lighting conditions.

9. The system of claim 1, wherein the user interface is configured for healthcare providers to visualize the first output and the second output alongside the input that is contributing to the first output and the second output, facilitating a holistic approach to patient counselling and treatment management.

10. The system of claim 1, wherein the machine learning model comprises one or more of logistic regressions, support vector machines (SVM), K-nearest neighbors, decision trees, and ensemble models; and wherein the ensemble model comprises one or more of random forests, extra trees, and bagging.

11. The system of claim 1, wherein the clinical data comprises one or more of clinical observations made by healthcare, diagnostic test results, and treatment information, health monitoring data, behavioral and lifestyle information, and patient-reported outcomes.

12. The system of claim 1, wherein the first output further comprises a prediction of progress rate.

13. The system of claim 1, wherein the system may further provide a third output comprising one or more of treatment strategies, treatment options, and appointment schedule generation.

14. The system of claim 1, wherein the machine learning model is configured to learn using labelled data using a supervised learning, wherein the supervised learning comprises logic using at least one of a decision tree, a logistic regression, a support vector machine, a k-nearest neighbors, a Naïve Bayes, a random forest, a linear regression, and a polynomial regression.

15. The system of claim 1, wherein the machine learning model is configured to learn from real-time data using an unsupervised learning, wherein the unsupervised learning comprises logic using at least one of a k-means clustering, a hierarchical clustering, a hidden Markov model, and an apriori algorithm.

16. A method comprising,
receiving, via an input module, an input data, wherein the input data comprises an image of an ocular region of a user, clinical data of the user, and external factors;
extracting, using an image processing module comprising adaptive filtering techniques, ocular characteristics, wherein the ocular characteristics comprise one or more of Optic Disc Size, Cup Disc Ratio, Optic Disc, Fundus, IOP, Ocular Alignment, Tor CA unaided, BCVA, SPH, Cyl, Tor fr corr axis;
combining, using a multimodal fusion module, the input data to determine a holistic health embedding;
detecting, based on a machine learning model and the holistic health embedding, a first output, wherein the first output comprises likelihood of myopia, and severity of myopia;
predicting, based on the machine learning model and the holistic health embedding, a second output, wherein the second output comprises an onset of myopia and a progression of myopia in the user;
stratifying, risk category of myopia of the user;
displaying, on a user interface, one or more of the first output and the second output;
receiving, a first feedback of the first output and the second output from the machine learning model, to dynamically adjust an accuracy of the first output and the second output from the machine learning model; and
receiving, a second feedback from a physician, to dynamically adjust the accuracy of the first output and the second output from the machine learning model; and
wherein the machine learning model is a pre-trained model with a data set comprising the input data from plurality of patients to recognize one or more patterns using the holistic health embedding; and
wherein the method is configured for myopia prognosis powered by multimodal data.

17. The method of claim 16, wherein the external factors comprise one or more of device screen exposure time, outdoor activity metrics, and social determinants of health.

18. The method of claim 16, wherein the user interface is configured for healthcare providers to visualize the first output and the second output alongside the input that is contributing to the first output and the second output, facilitating a holistic approach to patient counselling and treatment management.

19. A non-transitory computer-readable medium having stored thereon instructions executable by a computer system to perform operations comprising:
receiving, via an input module, an input data, wherein the input data comprises an image of an ocular region of a user, clinical data of the user, and external factors, wherein the external factors comprise one or more of device screen exposure time, outdoor activity metrics, and social determinants of health;
extracting, using an image processing module comprising adaptive filtering techniques, ocular characteristics, wherein the ocular characteristics comprise one or more of Optic Disc Size, Cup Disc Ratio, Optic Disc, Fundus, IOP, Ocular Alignment, Tor CA unaided, BCVA, SPH, Cyl, Tor fr corr axis;
combining, using a multimodal fusion module, the input data to determine a holistic health embedding;
detecting, based on a machine learning model and the holistic health embedding, a first output, wherein the first output comprises likelihood of myopia, and severity of myopia;
predicting, based on the machine learning model and the holistic health embedding, a second output, wherein the second output comprises an onset of myopia and a progression of myopia in the user;
stratifying, risk category of myopia of the user;
displaying, on a user interface, one or more of the first output and the second output;
receiving, a first feedback of the first output and the second output from the machine learning model, to dynamically adjust an accuracy of the first output and the second output from the machine learning model; and
receiving, a second feedback from a physician, to dynamically adjust the accuracy of the first output and the second output from the machine learning model; and
wherein the machine learning model is a pre-trained model with a data set comprising the input data from plurality of patients to recognize one or more patterns using the holistic health embedding; and
wherein the instructions is configured for myopia prognosis powered by multimodal data.

20. The non-transitory computer-readable medium of claim 19, wherein the external factors comprise one or more of the device screen exposure time, the outdoor activity metrics, and the social determinants of health.

* * * * *